(12) United States Patent
Davis et al.

(10) Patent No.: US 11,883,146 B1
(45) Date of Patent: Jan. 30, 2024

(54) METHODS AND DEVICES FOR SELECTING MINIATURIZED IMPEDANCE ELECTRODES OF MINIATURIZED IMPEDANCE SENSORS

(71) Applicant: Brigham Young University, Provo, UT (US)

(72) Inventors: Robert Davis, Provo, UT (US); Nick Morrill, Provo, UT (US); David Miller, Morgan, UT (US)

(73) Assignee: Brigham Young University, Provo, UT (US)

( * ) Notice: Subject to any disclaimer, the term of this patent is extended or adjusted under 35 U.S.C. 154(b) by 661 days.

(21) Appl. No.: 16/669,412

(22) Filed: Oct. 30, 2019

(51) Int. Cl.
*A61B 5/0531* (2021.01)
*A61B 5/021* (2006.01)
*A61B 5/00* (2006.01)

(52) U.S. Cl.
CPC ........ *A61B 5/0531* (2013.01); *A61B 5/02116* (2013.01); *A61B 5/681* (2013.01); *A61B 5/0006* (2013.01)

(58) Field of Classification Search
CPC ......... A61B 5/053–0532; A61B 5/0535–0537; A61B 5/0295; A61B 5/061; A61B 5/063; A61B 5/0809; A61B 5/068; A61B 5/085; A61B 5/14532; A61B 2017/00026–0003; A61B 2018/00875; A61B 5/6824; A61B 5/02116; A61B 5/681; A61B 5/0006
See application file for complete search history.

(56) References Cited

U.S. PATENT DOCUMENTS 6,528,020 B1 3/2003 Dai et al.
6,560,480 B1 * 5/2003 Nachaliel ............ A61B 5/6848
600/547

(Continued)

FOREIGN PATENT DOCUMENTS

JP 3766682 B2 4/2006
WO WO-2010085969 A1 * 8/2010 .......... A61B 5/0531
WO WO-2019169192 A1 * 9/2019 .......... A61B 5/1468

OTHER PUBLICATIONS

Pupo et al. Analytical and numerical solutions of the potential and electric field generated by different electrode arrays in a tumor tissue under electrotherapy, Sep. 2011, BioMed Eng Online 10: 85, pp. 5, 7, 10 (Year: 2011).*

*Primary Examiner* — Matthew Kremer
*Assistant Examiner* — Om Patel
(74) *Attorney, Agent, or Firm* — Miller IP Law, LLC

(57) ABSTRACT

A method, system, apparatus, and/or device to select a depth within a body part to measure an impedance. The method, system, apparatus, and/or device may include: a band configured to extend at least partially around a body part of a user; a user interface coupled to the band; a miniaturized impedance sensor embedded in the band and positioned in the band to be pressed against the body part when the user wears the band, the miniaturized impedance sensor including an array of miniaturized electrodes, where the array of miniaturized electrodes is configured to measure an impedance at a depth within the body part and the depth corresponds to a subdermal feature within the body part; a processing device coupled to the band, where the processing device is configured to select the depth within the body part to measure an impedance; and an electrical circuit embedded in the band.

20 Claims, 37 Drawing Sheets

(56) References Cited

U.S. PATENT DOCUMENTS

| | | | |
|---|---|---|---|
| 6,809,462 B2 | 10/2004 | Pelrine et al. | |
| 7,596,415 B2 | 9/2009 | Brabec et al. | |
| 8,348,841 B2 | 1/2013 | Varadan | |
| 8,746,075 B2 | 6/2014 | Eichhorn | |
| 8,764,651 B2 * | 7/2014 | Tran .................... | A61B 5/0205 |
| | | | 600/300 |
| 8,945,017 B2 | 2/2015 | Venkatraman et al. | |
| 8,946,683 B2 | 2/2015 | Rogers et al. | |
| 9,320,885 B2 | 4/2016 | Vasapollo | |
| 10,441,185 B2 * | 10/2019 | Rogers ................. | A61B 5/4875 |
| 2015/0366504 A1 | 12/2015 | Connor | |
| 2015/0367122 A1 | 12/2015 | Morshed et al. | |
| 2016/0066852 A1 * | 3/2016 | Cheng .................. | A61B 5/6831 |
| | | | 600/390 |
| 2019/0021616 A1 | 1/2019 | Day et al. | |

* cited by examiner

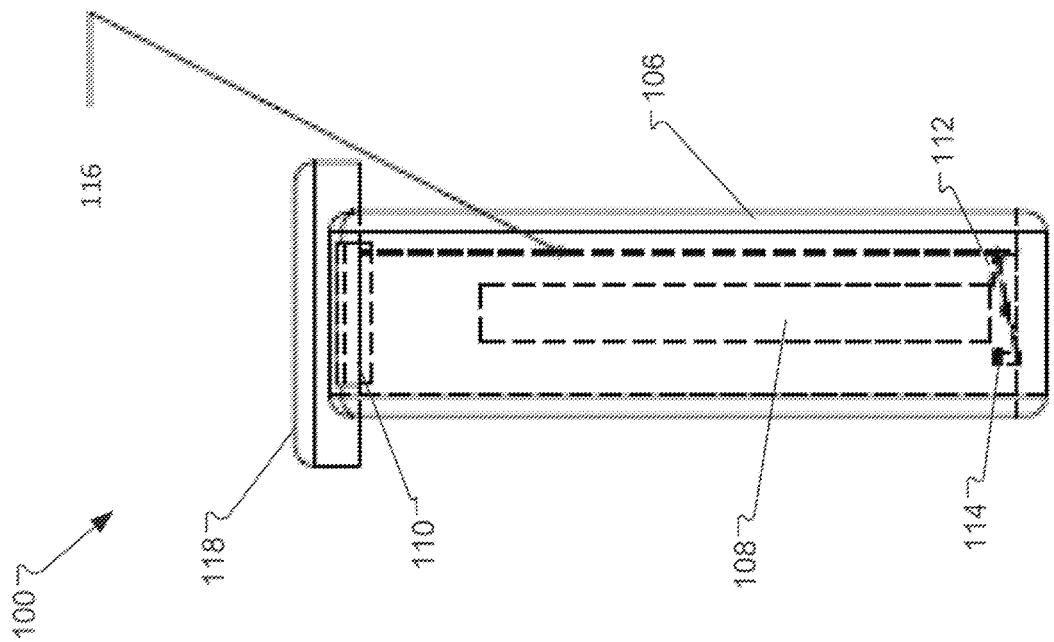
FIG. 2C
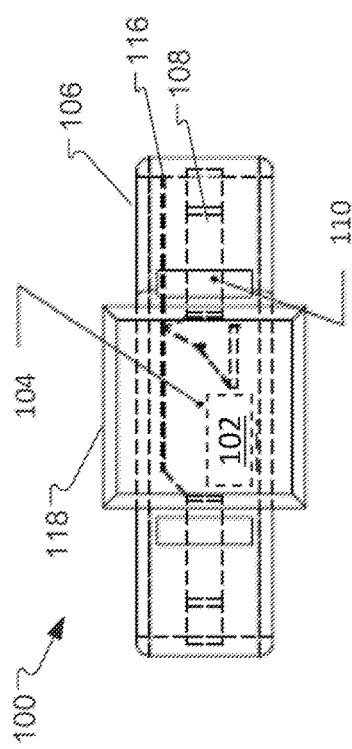
FIG. 2A
FIG. 2B

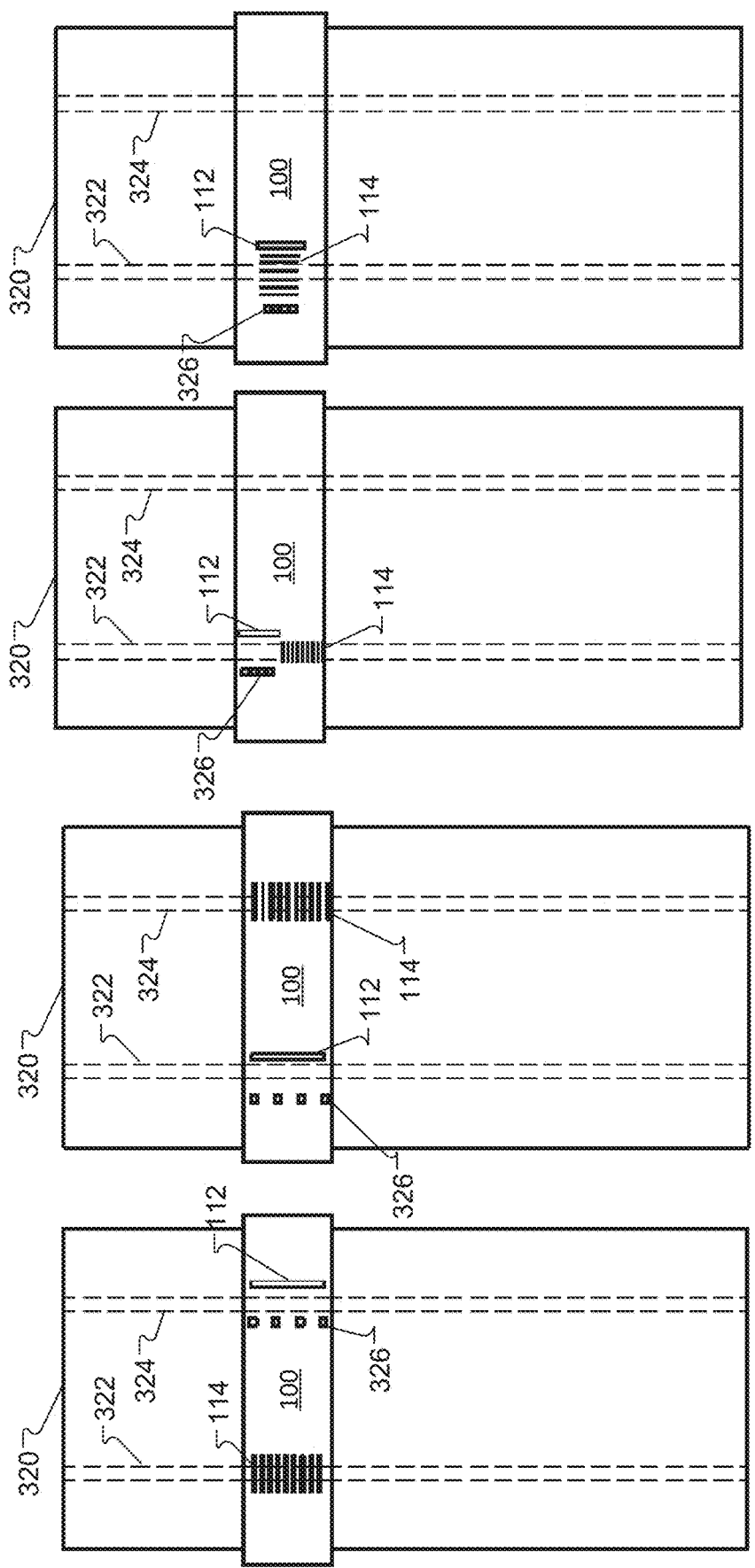

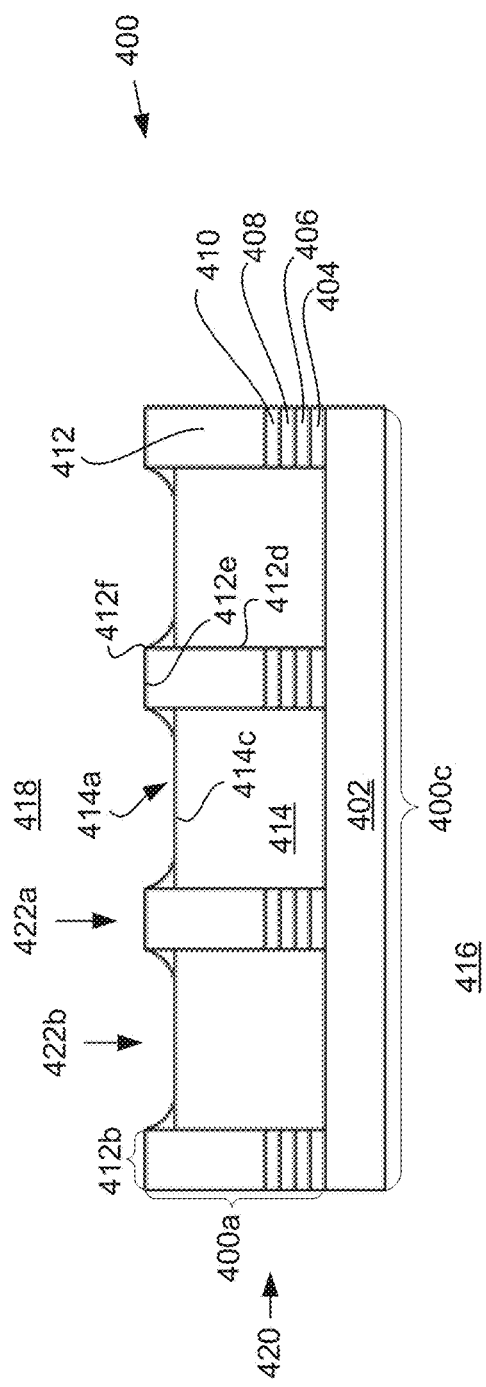
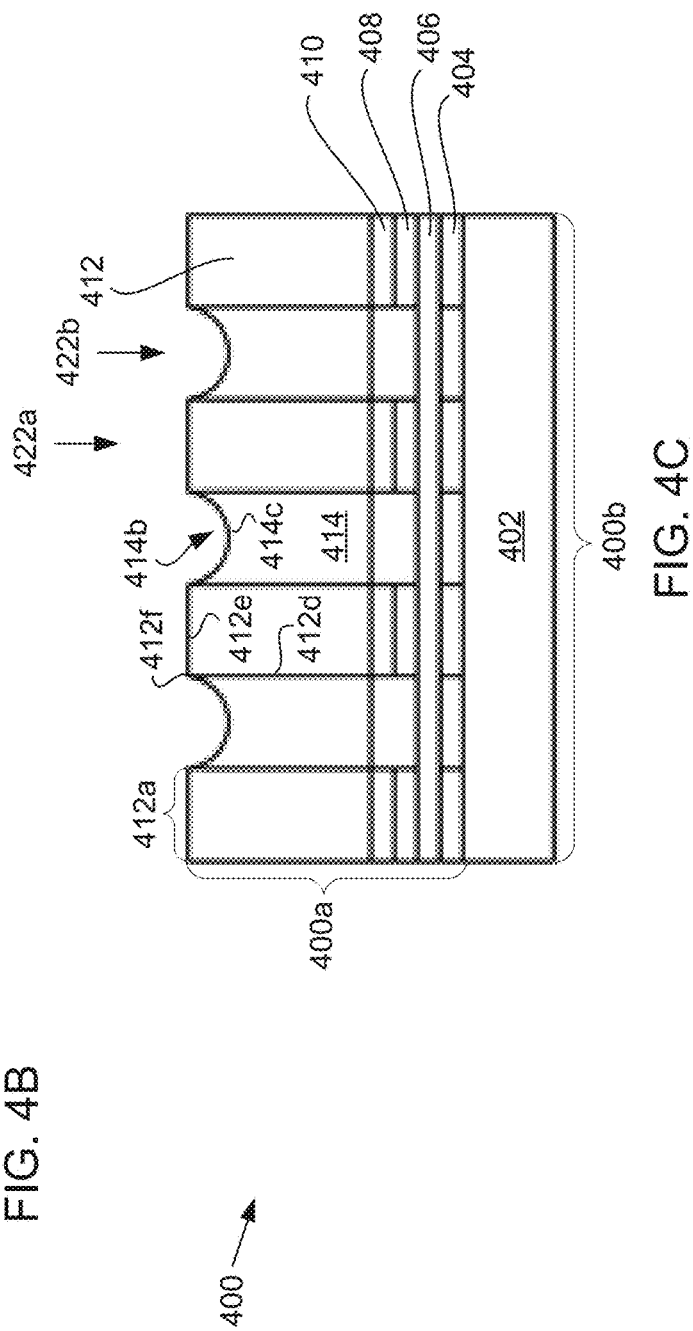

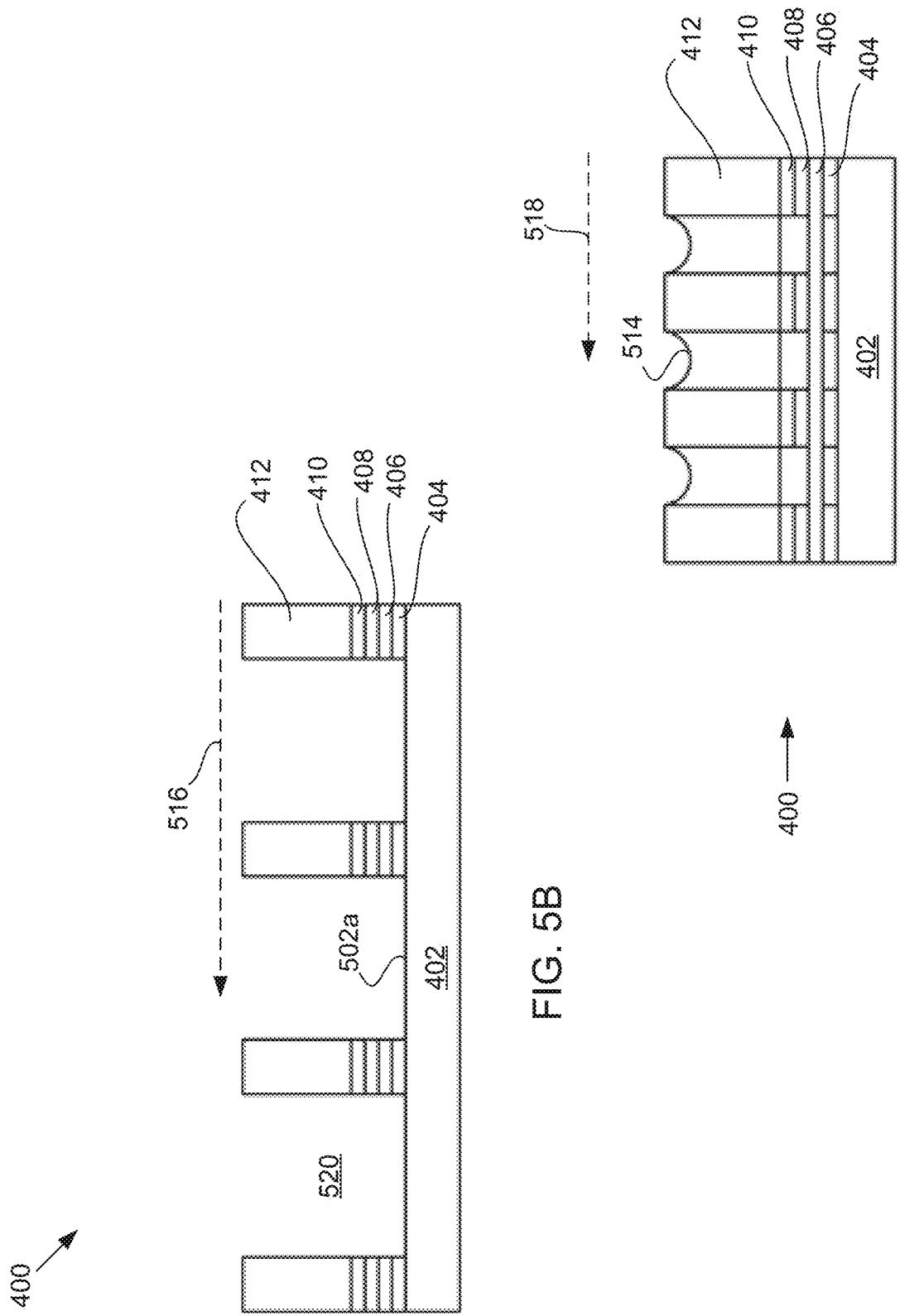

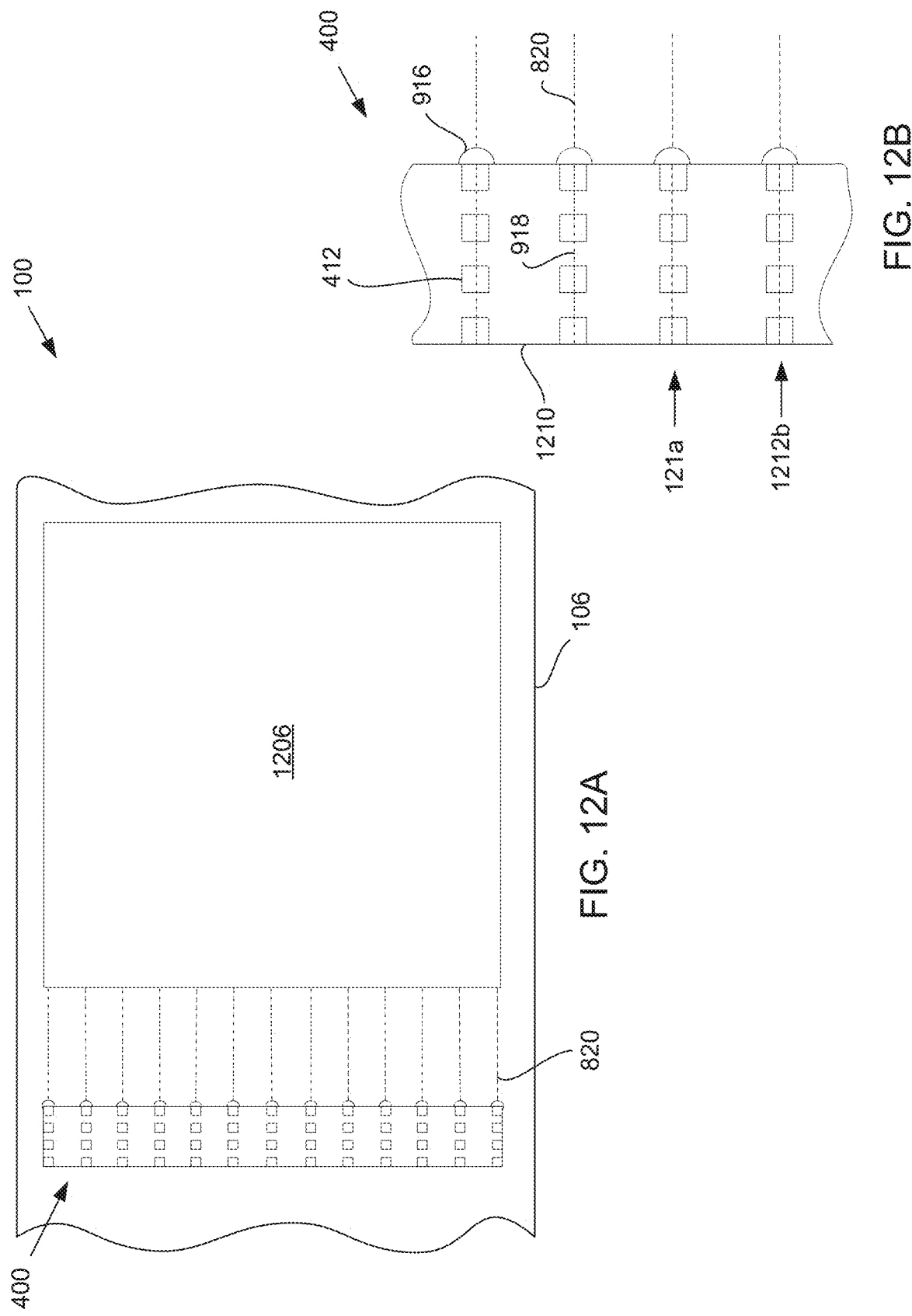

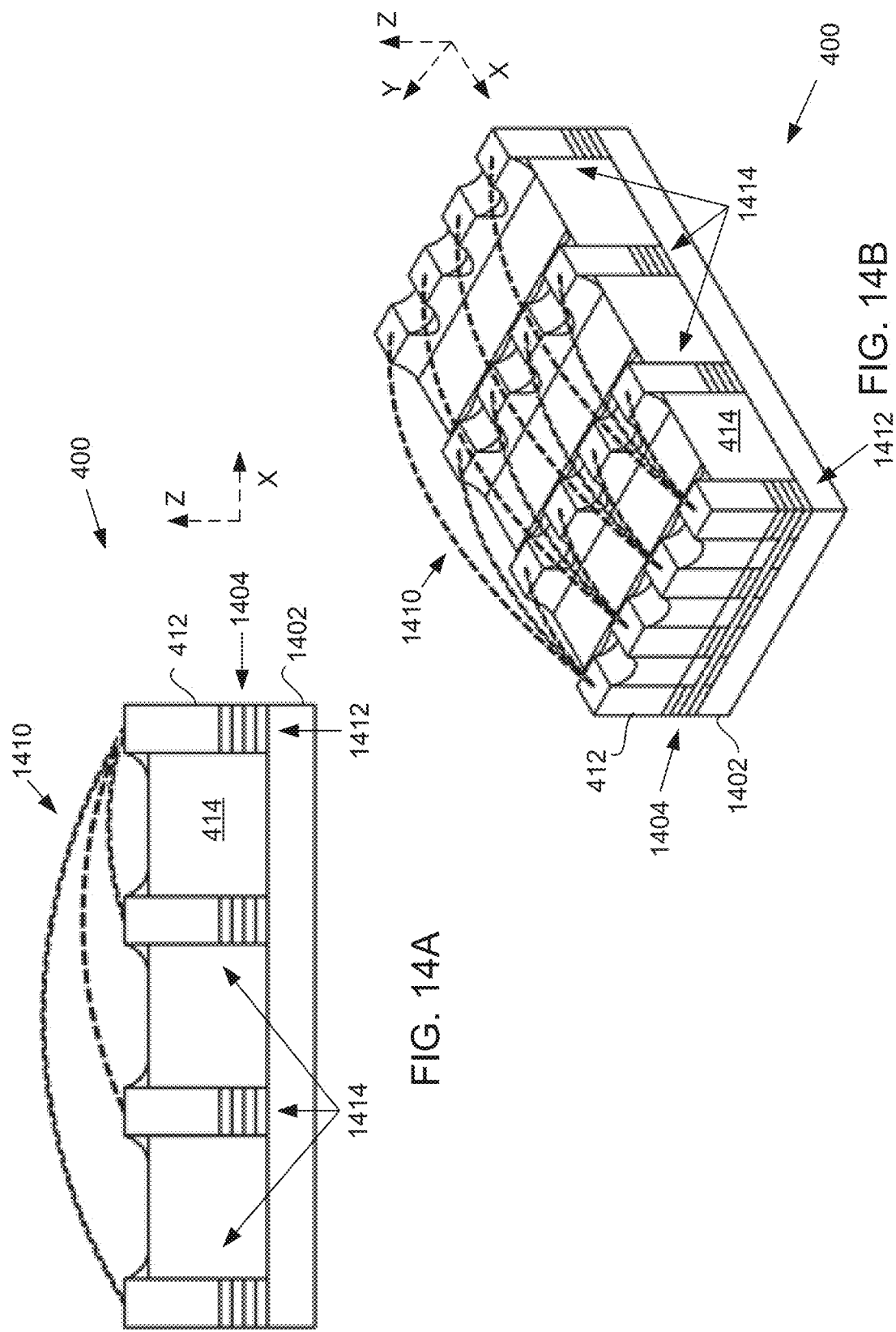

2200

2204
Pattern polymeric pillars onto substrate with patterned electrodes

2206
Deposit conductive film over polymeric pillars

2208
Etch film to electrically isolate pillars.

2210
Coat with interstitial filler

2304
Mix CNTs into resin

2306
Print CNT resin onto flexible substrate

2308
Insulate sidewalls

FIG. 23

METHODS AND DEVICES FOR SELECTING MINIATURIZED IMPEDANCE ELECTRODES OF MINIATURIZED IMPEDANCE SENSORS

BACKGROUND

Electronic technologies may take advantage of micro- and nanoscale physical properties and interactions to perform functions of electronic devices. Nanoelectronics specifically take advantage of the molecular composition of materials and the structural properties of materials at the nanoscale. Such structures may include thin films and/or nanotubes. Thin films generally comprise materials layered in single- to multi-atom-thick sheets. Thin films may be used in optical applications, electrical applications, and/or may be used as a protective layer. Nanotubes may generally include materials formed into tubes with single- to multi-atom-thick walls. Nanotubes may be used in electrical applications as conductors, and/or may be used to provide nanoscale structural support.

BRIEF DESCRIPTION OF THE DRAWINGS

The present description will be understood more fully from the detailed description given below and from the accompanying drawings of various embodiments of the present embodiment, which description is not to be taken to limit the present embodiment to the specific embodiments but are for explanation and understanding. Throughout the description the drawings may be referred to as drawings, figures, and/or FIGs.

FIG. 2A illustrates a top exposed view of the wearable device in FIG. 1, according to an embodiment.

FIG. 2B illustrates a profile view of the wearable device, according to an embodiment.

FIG. 2C illustrates a side view of the wearable device, according to an embodiment.

FIG. 3B illustrates the wearable device with the second sensor being located approximate the first muscular-walled tube and the light source and the first sensor being located approximate the second muscular-walled tube, according to an embodiment.

FIG. 3C illustrates the wearable device with the second sensor being located approximate the second muscular-walled tube and the light source and the first sensor being located approximate the first muscular-walled tube, according to an embodiment.

FIG. 3D illustrates the wearable device with the light source, the first sensor, and the second sensor being located longitudinally and approximate the first muscular-walled tube, according to an embodiment.

FIG. 3E illustrates the wearable device with the light source, the first sensor, and the second sensor being located laterally and approximate the first muscular-walled tube, according to an embodiment.

FIG. 4B illustrates a head-on view of a first side of the miniaturized impedance sensor illustrated in FIG. 4A, according to an embodiment.

FIG. 4C illustrates a head-on view of a second side of the miniaturized impedance sensor illustrated in FIG. 4A, according to an embodiment.

FIG. 5B illustrates a head-on view of a first side of the miniaturized impedance sensor illustrated in FIG. 5A, according to an embodiment.

FIG. 5C illustrates a head-on view of a second side of the miniaturized impedance sensor illustrated in FIG. 5A, according to an embodiment.

FIG. 12A illustrates a schematic view of a section of the wearable device with an integrated sensor, according to an embodiment.

FIG. 12B illustrates a zoomed in view of the integrated sensor illustrated in FIG. 12A, according to an embodiment.

FIG. 14A illustrates impedance paths for the miniaturized impedance sensor from a side view of the miniaturized impedance sensor, according to an embodiment.

FIG. 14B illustrates the impedance paths for the miniaturized impedance sensor of FIG. 14A from a perspective view of the miniaturized impedance sensor, according to an embodiment.

FIG. 22 illustrates a method for preparing the miniaturized impedance sensor with polymeric nano structures, according to an embodiment.

FIG. 23 illustrates a method for three-dimensional printing of the miniaturized impedance sensor, according to an embodiment.

DETAILED DESCRIPTION

Figure 1:
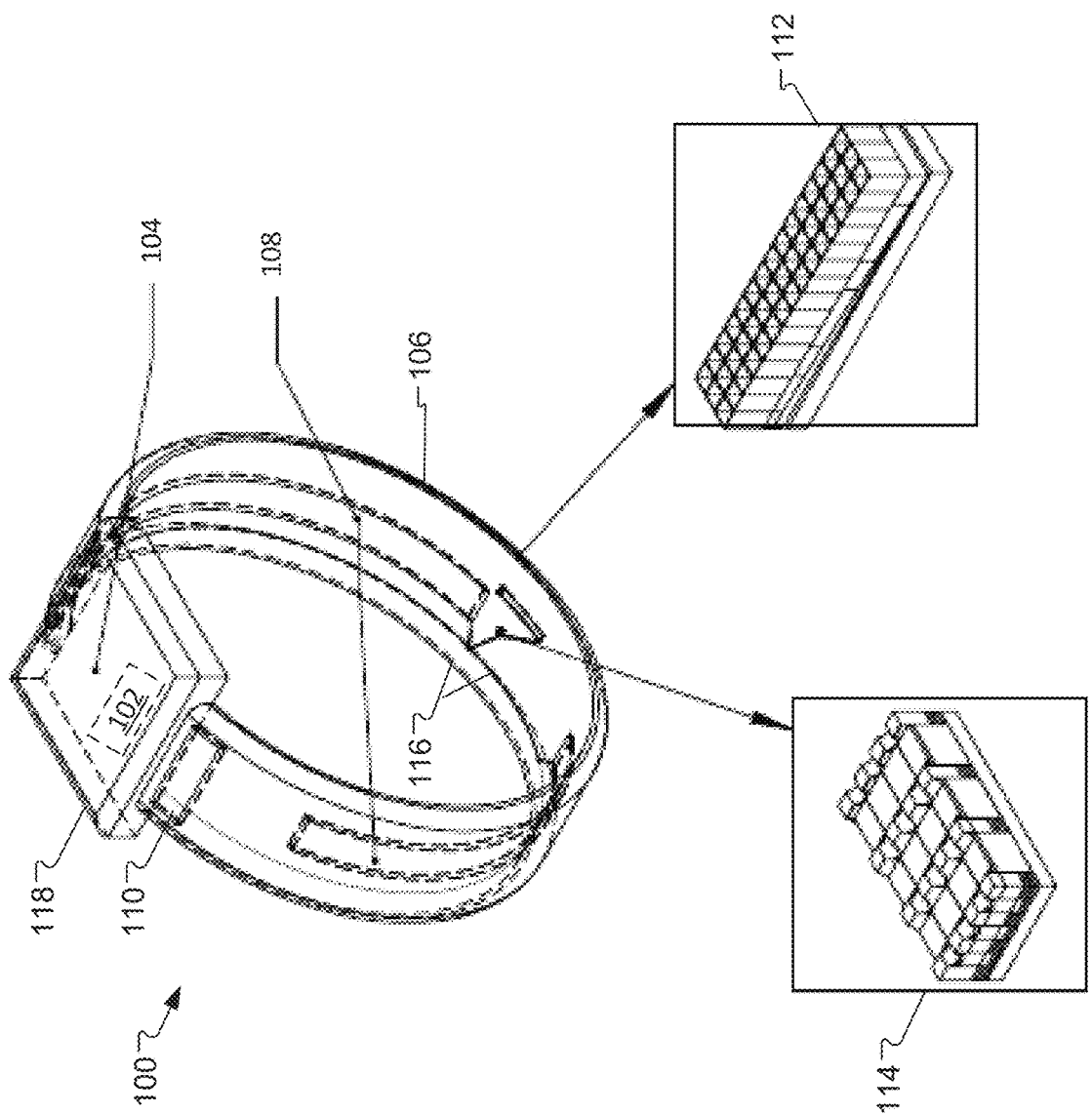
FIG. 1 illustrates a perspective view of a wearable device, according to an embodiment.

Miniaturized impedance sensors as disclosed herein will become better understood through a review of the following detailed description in conjunction with the figures. The detailed description and figures provide merely examples of the various embodiments described herein. Those skilled in the art will understand that the disclosed examples may be varied, modified, and altered and not depart from the scope of the embodiments described herein. Many variations are contemplated for different applications and design considerations; however, for the sake of brevity, the contemplated variations may not be individually described in the following detailed description.

Throughout the following detailed description, example embodiments of various miniaturized impedance sensors are provided. Related elements in the example embodiments may be identical, similar, or dissimilar in different examples. For the sake of brevity, related elements may not be redundantly explained in multiple examples. Instead, the use of a same, similar, and/or related element names and/or reference characters may cue the reader that an element with a given name and/or associated reference character may be similar to another related element with the same, similar, and/or related element name and/or reference character in an example embodiment explained elsewhere herein. Elements specific to a given example may be described regarding that particular example embodiment. A person having ordinary skill in the art will understand that a given element need not be the same and/or similar to the specific portrayal of a related element in any given figure or example embodiment in order to share features of the related element.

As used herein "may" should be interpreted in the permissive sense and should not be interpreted in the indefinite senses. Use of "is" regarding embodiments, elements, and/or features should be interpreted to be definite only regarding a specific embodiment and should not be interpreted as definite regarding the invention as a whole. References to "the disclosure" and/or "this disclosure" refer to the entirety of the writings of this document and the entirety of the accompanying illustrations, which extends to all the writings of each subsection of this document, including the Title, Background, Brief description of the Drawings, Detailed Description, Claims, and Abstract. Terms such as "configured to," "operable to," "designed to," "positioned to," "aligned to," and so forth indicate a purposeful design feature as opposed to a happenstance structural capability.

Where multiples of a particular element are shown in a FIG., and where it is clear that the element is duplicated throughout the FIG., only one label may be provided for the element, despite multiple instances of the element being present in the FIG. Accordingly, other instances in the FIG. of the element having identical or similar structure and/or function may not have been redundantly labeled. A person having ordinary skill in the art will recognize based on the disclosure herein redundant and/or duplicated elements of the same FIG. Despite this, redundant labeling may be included where helpful in clarifying the structure of the depicted example embodiments.

A conventional wearable device may include a means of attaching the device to a user and one or more measurement devices. Such conventional devices may include devices such as a step counter, a smart watch, a Fitbit™, an Apple™ watch, a Samsung™ watch, and so forth. Currently, the amount and type of data collected from an individual wearing a wearable device may be limited by the space available in a wearable for sensors, communications chips, processors, power sources, the accuracy of sensors capable of being integrated into a wearable device, the size of the sensors, and/or the materials used for the sensors. Previous sensors have been too large to fit on a user comfortably in a wearable and/or have not been accurate enough to provide meaningful data. A specific example regards conventional bioimpedance sensors. A conventional bioimpedance sensor may include two impedance pads. A particular physiological condition that may be measured by a conventional bioimpedance sensor may depend on the size of each impedance pad relative to the current delivered from one impedance pad to the other and/or the separation distance between the impedance pads. Accordingly, the practicality of implementing a conventional bioimpedance sensor on a wearable device may be limited by the minimum size of the impedance pads and the ways in which wearing such device may be tolerable to a user.

A further limiting factor of conventional bioimpedance sensors may be the amount and time of contact the impedance pads have with skin of a user. The presence of water, such as sweat, on the skin may affect the measurement, as may the surface area of the impedance pad contacting the skin at the time the measurement is taken. In order to maximize the accuracy of a measurement taken, the amount of surface area contact between the skin of a user and the impedance pads may be optimized. The present inventors have discovered that there may be an "acclimation period" over which the skin against which a bioimpedance sensor may be placed tends to conform to the bioimpedance sensor shape. If the wearable is jostled or moved on the user, this may restart the acclimation period. Thus, in addition to minimizing the movability of the wearable on the user, minimizing the acclimation may improve measurement accuracy.

Implementations of embodiments described and/or illustrated throughout this disclosure may address the above-mentioned deficiencies by providing methods, systems, devices, and/or apparatuses that may incorporate miniaturized impedance sensors. In one embodiment, a miniaturized impedance sensor may include a miniaturized impedance sensor. The miniaturized impedance sensor may include miniaturized electrodes on a flexible substrate. The miniaturized impedance sensor may be integrated into a flexible and/or durable wearable device. An advantage of the miniaturized impedance sensor may be improved contact between the sensor and a user wearing the wearable device. Another advantage of the miniaturized impedance sensor is that a large number of electrodes may be incorporated into the sensor over a relatively small area, allowing for a variety of measurement depths using a single sensor. Yet another advantage of the miniaturized impedance sensor may be durability against traumas such as strikes, bending, drops, and so forth. Yet another advantage of the miniaturized impedance sensor may be drastic reduction and/or elimination of the acclimation period.

FIG. 1 illustrates a wearable device 100 with integrated sensors 112 and/or 114, according to an embodiment. The elements and/or features described regarding FIG. 1 may be the same as and/or similar to other similarly named elements and/or features described and/or illustrated throughout this disclosure. In one embodiment, the wearable device 100 may be configured to take physiological measurements of a user. The wearable device 100 may include a housing 118 and an attachment mechanism 106, such as a band, that are configured or shaped to attach to a body of the user. In one embodiment, the wearable device 100 may be a wrist worn device that may be configured to attach to a wrist or arm of the user. In one example, the integrated sensors 112 and/or 114 may be positioned against an inside region of the wrist when the user wears the wearable device 100. The inside region of the wrist may face towards the user in a natural resting position. In another example, when the integrated sensors 112 and/or 114 may be positioned against an inside region of the body part, such as the wrist, the integrated sensors 112 and/or 114 may be positioned adjacent to, approximate to, or directly over a muscular-walled tube that is closest to an outer surface of the body part. In another embodiment, the wearable device 100 may be attached to a head of the user using a headband, to a chest of the user using a chest band, to an ankle of the user using an ankle band, or otherwise attached to a body of the user using a sweatband, bandage, band, watch, bracelet, ring, adherent, or other attachments and connections.

In various embodiments, the housing 118 may be moveably coupled to the band 106. In one example, the band 106 may be a flexible band designed to flex into a curvilinear shape. The flexible band with a shape, size, and/or flexibility designed for attaching the band 106 to a wrist of a user. The wrist may include a dermal layer along an underside of the wrist and a muscular-walled tube within the wrist adjacent to the dermal layer along the underside of the wrist. The housing 118 may be configured with external electrical contacts. The band 106 may be configured with multiple contact points or a continuous contact strip. The housing 118 may be coupled to the band 106 such that the external electrical contacts of the housing 118 form electrical contact with the one or more of the multiple contact points or the continuous contact strip of the band 106. The housing 118 may be moved on the band 106 to a different position and still maintain electrical communication with electrical components embedded in the band 106 such as the electrical trace or circuit 116, the first sensor 112, or the second sensor 114.

The wearable device 100 may include a processing device 102, a user interface or display device 104, the band 106, a power source 108, a processing unit 110, the first sensor 112, and/or the second sensor 114. In one embodiment, the processing device 102, the user interface or display device 104, the power source 108, the processing unit 110, the first sensor 112, and/or the second sensor 114 may be electronically coupled and/or communicatively coupled. In another embodiment, the processing device 102 and the display device 104 may be integrated into the housing 118 of the wearable device 100. In another embodiment, the power source 108, the processing unit 110, the first sensor 112, and/or the second sensor 114 may be integrated into the band 106 of the wearable device 100. In one embodiment, the first sensor 112 and/or the second sensor 114 may be integrated or positioned along an inside surface or interior surface of the band 106, such that the first sensor 112 and/or the second sensor 114 may be flush with the surface of the band 106 to contact a body part of a user when worn or protrude from a surface of the band 106 to extend toward a surface of the body part of the user when worn. In another embodiment, the band 106 may include a cavity that the power source 108, the processing unit 110, the first sensor 112, and/or the second sensor 114 may be stored in. In another embodiment, the band 106 may be formed or molded over the power source 108, the processing unit 110, the first sensor 112, and/or the second sensor 114. In another embodiment, the power source 108, the first sensor 112, and/or the second sensor 114 may be connected to the processing unit 110 and/or the processing device 102 by one or more electrical trace(s) or circuit(s) 116 (such as flexible circuit boards).

In one embodiment, the first sensor 112 may be a miniaturized spectrometer. The miniaturized spectrometer may include a carbon-nanotube structure forming a collimator, an optical filter, and a photodetector stacked together and embedded in the band 106. The photodetector may be positioned in the band 106 to face the user's body part 320 when the user wears the band 106. In another embodiment, the second sensor 114 may be a miniaturized impedance sensor. In another embodiment, the first sensor 112 and/or the second sensor may be a temperature sensor, a viscosity sensor, an ultrasonic sensor, a humidity sensor, a heart rate sensor, a dietary intake sensor, an electrocardiogram (EKG) sensor, an ECG sensor, a galvanic skin response sensor, a pulse oximeter, an optical sensor, and so forth. In another embodiment, the wearable device 100 may include other sensors integrated or attached to the band 106 or the housing 118. In another embodiment, the wearable device 100 may be communicatively coupled to the wearable device 100, such as sensors of other devices or third-party devices.

The first sensor 112 and/or the second sensor 114 may be coupled to the processing unit 110. The processing unit 110 may be configured to manage or control the first sensor 112, the second sensor 114, and/or the power source 108. In one embodiment, the processing unit 110 may control a frequency or rate over time that the first sensor 112 and/or the second sensor 114 take measurements, a wavelength or optical frequency at which the first sensor 112 and/or the second sensor 114 take measurements, a power consumption level of the first sensor 112 and/or the second sensor 114, a sleep mode of the first sensor 112 and/or the second sensor 114 and so forth. In another embodiment, the processing unit 110 may control or adjust measurements taken by the first sensor 112 and/or the second sensor 114 take measurements to remove noise, increase a signal to noise ratio, dynamically adjust the amount of measurements taken over time, and so forth.

In another embodiment, the power source 108 may be coupled to the processing unit 110. The power source 108 may be a battery, a solar panel, a kinetic energy device, a heat converter power device, a wireless power receiver, and so forth. The processing unit 110 may be configured to transfer power from the power source 108 to the processing device 102, the display device 104, the first sensor 112, the second sensor 114, and/or other devices or units of the wearable device 100. In one embodiment, the processing unit 110 may be configured to regulate an amount of power provided from the power source 108 to the processing device 102, the display device 104, the first sensor 112, the second sensor 114, and/or other devices or units of the wearable device 100. In another embodiment, the wearable device 100 may include a power receiver to receive power to recharge the power source 108. For example, the power receiver may be a wireless power coil, a universal serial bus (USB) connector, a thunderbolt connector, a mini USB connector, a micro USB connector, a USB-C connector, and so forth. The power receiver may be coupled to the processing unit 110, the processing device 102, the power source 108, and so forth. In one embodiment, the processing unit 110 may be configured to regulate an amount of power provided from the power receiver to the power source 108. In another embodiment, the processing unit 110 may be a power management unit configured to control battery management, voltage regulation, charging functions, direct current (DC) to DC conversion, voltage scaling, power conversion, dynamic frequency scaling, pulse-frequency modulation (PFM), pulse-width modulation (PWM), amplification, and so forth. In another embodiment, the processing unit 110 may include a communication device configured to send and/or receive data via a cellular communication channel, a wireless communication channel, a Bluetooth® communication channel, a radio communication channel, a WiFi® communication channel, and so forth.

The processing device 102 may include a processor, a data storage device, a communication device, a graphics processor, and so forth. In one embodiment, the processing device 102 may be coupled to the processing unit 110, the power source 108, the first sensor 112, and/or the second sensor 114. In one embodiment, the processing device 102 may be configured to receive measurement data from the processing unit 110, the first sensor 112, and/or the second sensor 114. In one embodiment, the processing device 102 may be configured to process the measurement data and display information associated with the measurement data at the display device 104. In another embodiment, the processing device 102 may be configured to communicate the measurement data to another device. In one embodiment, the other device may process the measurement data and provide information associated with the measurement data to the user or another individual. In another embodiment, the other device may process the measurement data and provide results, analytic information, instructions, and/or notifications to the processing device 102 to provide to the user. The wearable device 100 may communicate information associated with the measurement data or information related to the measurement data to a user via the display device 104, a buzzer, a vibrator, a speaker, a microphone, and so forth. In one example, the display device 104 may include an input device, such as a button, a touch screen, a touch display, an so forth that may receive an input form the user.

In another embodiment, the wearable device 100 may be part of a system connected to other devices. For example, the wearable device 100 may be configured to send and/or receive data with another device. In one embodiment, the wearable device 100 may be configured to receive data from another measurement device, aggregate the received data with measurement data from the first sensor 112 and/or the second sensor 114, analyze the aggregated data, and provide information or notifications associated with the analyzed data.

FIGS. 2A-C illustrate side and top views of a wearable device 100, according to an embodiment. FIG. 2A illustrates a top exposed view of the wearable device 100 in FIG. 1, according to an embodiment. Some of the features in FIG. 2A are the same as or similar to some of the features in FIG. 1 as noted by same and/or similar reference characters, unless expressly described otherwise. Furthermore, the elements and/or features described regarding FIG. 2A may be the same as and/or similar to other similarly named elements and/or features described and/or illustrated throughout this disclosure. As discussed above, the wearable device 100 may be a wrist-worn device that may be configured to attach to a wrist of a user. As further discussed above, the processing device 102 and the display device 104 may be integrated into the housing 118 of the wearable device 100 and the power source 108, the processing unit 110, the first sensor 112, and/or the second sensor 114 may be integrated into the band 106 of the wearable device 100. In one embodiment, the band 106 may include a cavity that the power source 108, the processing unit 110, the first sensor 112, and/or the second sensor 114 may be stored in. In another embodiment, the band 106 may be formed or molded over the power source 108, the processing unit 110, the first sensor 112, and/or the second sensor 114. In various embodiments, the band 106 may be formed of silicone and/or canvas material.

FIG. 2B illustrates a profile view of the wearable device 100, according to an embodiment. Some of the features in FIG. 2B are the same as or similar to some of the features in FIG. 1 and FIG. 2A as noted by same and/or similar reference characters, unless expressly described otherwise. Furthermore, the elements and/or features described regarding FIG. 2B may be the same as and/or similar to other similarly named elements and/or features described and/or illustrated throughout this disclosure. In one embodiment, the housing 118 with the processing device 102 and the display device 104 (as shown in FIGS. 1 and 2A) may be located at a top of the wearable device 100 such that the housing 118 may be located at a top surface of a wrist of a user when the user wears the wearable device 100 on their wrist. In another embodiment, the first sensor 112 and/or the second sensor 114 (as shown in FIGS. 1 and 2A) may be located at a bottom of the wearable device 100 such that the first sensor 112 and/or the second sensor 114 may be located at a bottom surface of a wrist of a user when the user wears the wearable device 100 on their wrist. In another embodiment, the power source 108 and/or the processing unit 110 (as shown in FIGS. 1 and 2A) may be located along a side of the wearable device 100 such that the power source 108 and/or the processing unit 110 may be located at a side surface of a wrist of a user when the user wears the wearable device 100 on their wrist.

FIG. 2C illustrates a side view of the wearable device 100, according to an embodiment. Some of the features in FIG. 2C are the same or similar to some of the features in FIGS. 1-2B as noted by same reference characters, unless expressly described otherwise. As discussed above, the wearable device 100 may include the power source 108, the processing unit 110, the first sensor 112, and/or the second sensor 114. In another embodiment, the power source 108, the first sensor 112, and/or the second sensor 114 may be connected to the processing unit 110 and/or the processing device 102 by one or more electrical trace(s) or circuit(s) 116. In one embodiment, the electrical trace 116 may extend at least partially along a circumference of the band 106. In one embodiment, the power source 108 may be located on one or both sides of the band 106, the first sensor 112 and/or the second sensor 114 may be located at a bottom of the band, and the processing unit 110 may be located at a side or a top of the band 106 (such as approximate the housing 118). In one embodiment, the electrical trace(s) 116 may extend along a circumference of the band 106 along a side or middle circumference of the band 106. The electrical trace(s) 116 may transfer data and/or power between the power source 108, the first sensor 112, the second sensor 114, the processing unit 110, the processing device 102 (as shown in FIG. 1), and/or the display device 104 (as shown in FIG. 1).

Figure 3A:
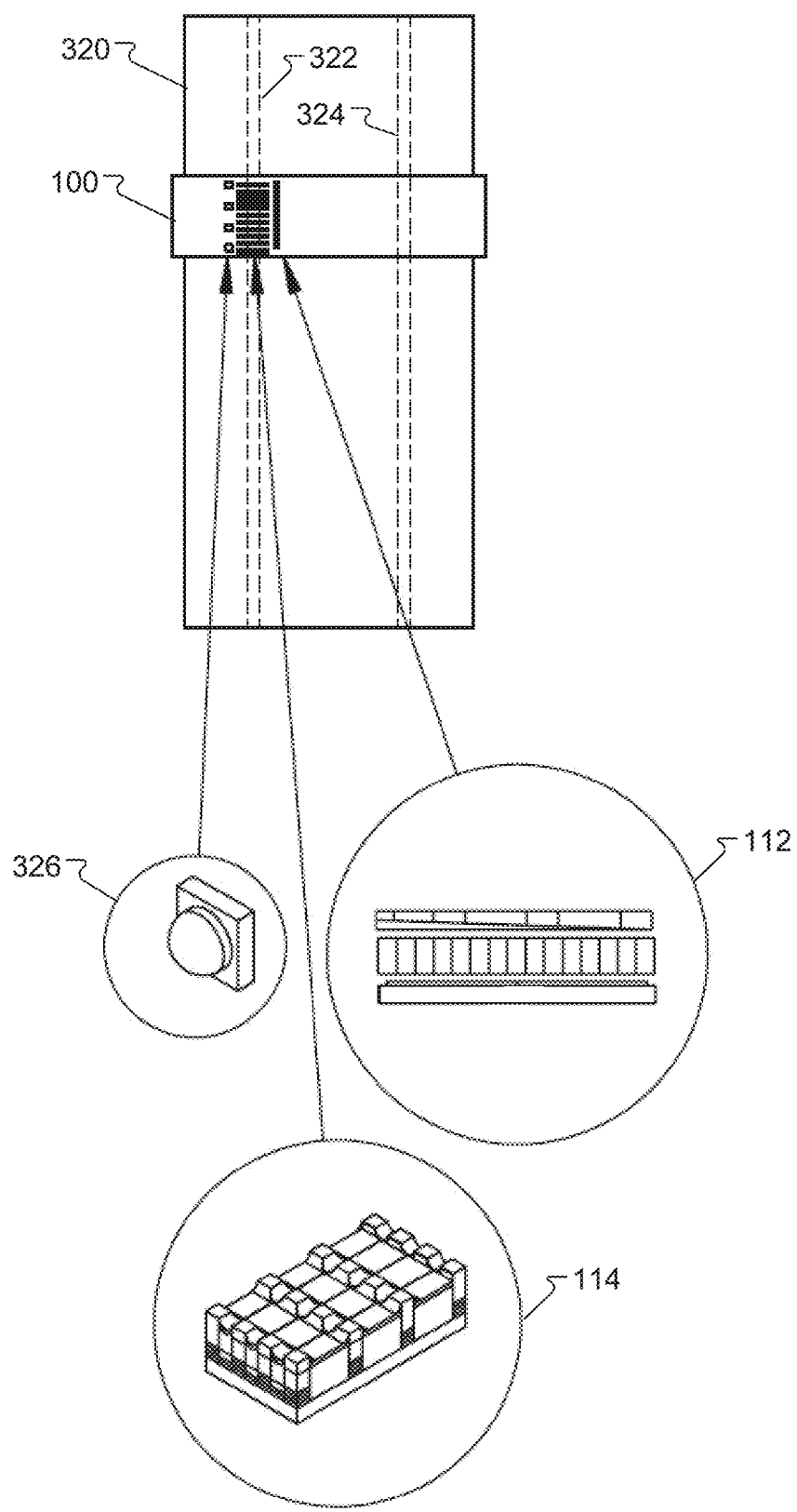
FIG. 3A illustrates the wearable device attached to a part of a body of an individual, according to an embodiment.

FIGS. 3A-H illustrate various embodiments of the wearable device 100 positioned on a user relative to veins and/or arteries of the user, according to various embodiments. FIG. 3A illustrates the wearable device 100 attached to a part of a body 320 of an individual, according to an embodiment. Some of the features in FIG. 3A are the same as or similar to some of the features in FIGS. 1-2B as noted by same and/or similar reference characters, unless expressly described otherwise. Furthermore, the elements and/or features described regarding FIG. 3A may be the same as and/or similar to other similarly named elements and/or features described and/or illustrated throughout this disclosure. In one embodiment, the wearable device 100 may be attached to the part of the body 320 of the individual. The part of the body 320 may be an arm, a leg, a hand, a wrist, a head, an appendage, and so forth of the body 320 of the individual. For example, the wearable device 100 may be attached to a wrist or arm of the body 320 of the individual. As discussed above, the wearable device 100 may include the first sensor 112 and/or the second sensor 114. In another embodiment, the first sensor 112 and or the second sensor 114 may be attached to a band of the wearable device 100 such that the first sensor 112 and/or the second sensor 114 may be aligned over a muscular-walled tube 322 and/or 324 of the body 320 of the individual. The muscular-walled tube 322 and/or 324 may be a vein, an artery, or other tubes or channels to circulate fluids in the body 320, such as blood, water, oxygen, and so forth. For example, the first muscular-walled tube 322 may be an ulnar artery or vein and the second muscular-walled tube 324 may be a radial artery or vein.

In one embodiment, the wearable device 100 may include one or more light sources 326 integrated into the band of the wearable device 100 such that the light sources 326 are offset to a first side of the first muscular-walled tube 322 and extend horizontally along surface of the skin offset to the muscular-walled tube 322. The light source(s) 326 may be light emitting diodes (LEDs), incandescent bulbs, tungsten bulbs, lasers, and so forth. In one embodiment, the wearable device 100 may include the first sensor 112 integrated into the band of the wearable device 100 such that the first sensor 112 may be offset to a second side of the muscular-walled tube 322 and extend horizontally along surface of the skin offset to the muscular-walled tube 322. In one embodiment, the light sources 326 may be located at a first side of the muscular-walled tube 322 and the first sensor 112 may be located opposite to the light sources 326 on the other side of the muscular-walled tube 322. In another embodiment, the second sensor 114 may be a miniaturized impedance sensor that may be positioned over top of the muscular-walled tube 322. The muscular-walled tube may include a blood vessel such as a vein or artery in an arm or wrist of a body 320 of the user, such as a human body. In one embodiment, the second sensor 114 may be integrated into the band of the wearable device 100 such that the second sensor 114 may run parallel to and extend horizontally along surface of the skin above the muscular-walled tube 322.

The first sensor 112 and the second sensor 114 may be compactly arranged in the wearable device 100. The close proximity of the first sensor 112, the second sensor 114, and/or the light source 326 may reduce an amount of wiring disbursed throughout the wearable device 100. The first sensor 112, the second sensor 114, and/or the light source 326 may be integrated into and/or on a single substrate. The substrate may be flexible and/or rigid. Compact arrangement of the sensors may allow for use of a rigid substrate, which may increase the durability of the sensors and/or the wearable device 100 overall. Compact arrangement of the sensor may also allow for consistency of measurement. In various embodiments, such as embodiments discussed regarding FIG. 26, measurements of multiple sensors may be correlated and/or aggregated. Compact arrangement may allow for measurement by multiple sensors of the same muscular-walled tube 322 at the same or roughly the same location on the muscular-walled tube. This may increase the precision of correlations and/or aggregations.

FIG. 3B illustrates the wearable device 100 with the second sensor 114 being located approximate the first muscular-walled tube 322 and the light source 326 and the first sensor 112 being located approximate the second muscular-walled tube 324, according to an embodiment. Some of the features in FIG. 3B are the same as or similar to some of the features in FIGS. 1-3A as noted by same and/or similar reference characters, unless expressly described otherwise. Furthermore, the elements and/or features described regarding FIG. 3B may be the same as and/or similar to other similarly named elements and/or features described and/or illustrated throughout this disclosure. In one embodiment, the second sensor 114 may be located over the first muscular-walled tube 322. In one embodiment, the second sensor 114 may include a miniaturized impedance sensor. In one embodiment, the first muscular-walled tube 322 may extend along a Y-axis of a first plane and the miniaturized impedance sensor may extend perpendicularly relative to the first muscular-walled tube 322 along an X-axis of a second plane, such that the miniaturized impedance sensor extends from a first side of the first muscular-walled tube 322 to a second side of the first muscular-walled tube 322. In another embodiment, the first sensor 112 may be located at a first side of the second muscular-walled tube 324 and the light source(s) 326 may be located on a second side of the second muscular-walled tube 324, such that the first sensor 112 and the light source(s) 326 straddle each side of second muscular-walled tube 324.

FIG. 3C illustrates the wearable device 100 with the second sensor 114 being located approximate the second muscular-walled tube 324 and the light source 326 and the first sensor 112 being located approximate the first muscular-walled tube 322, according to an embodiment. Some of the features in FIG. 3C are the same as or similar to some of the features in FIGS. 1-3B as noted by same and/or similar reference characters, unless expressly described otherwise. Furthermore, the elements and/or features described regarding FIG. 3C may be the same as and/or similar to other similarly named elements and/or features described and/or illustrated throughout this disclosure. In one embodiment, the second sensor 114 may be located over the second muscular-walled tube 324. In one embodiment, the second sensor 114 may include a miniaturized impedance sensor. In one embodiment, the second muscular-walled tube 324 may extend along a Y-axis of a first plane and the miniaturized impedance sensor may extend perpendicularly relative to the second muscular-walled tube 324 along an X-axis of a second plane, such that the miniaturized impedance sensor may extend from a first side of the second muscular-walled tube 324 to a second side of the second muscular-walled tube 324. In another embodiment, the first sensor 112 may be located at a first side of the first muscular-walled tube 322 and the light source(s) 326 may be located on a second side of the first muscular-walled tube 322, such that the first sensor 112 and the light source(s) 326 straddle each side of first muscular-walled tube 322.

The embodiments illustrated in FIGS. 3B-C generally illustrate embodiments where the first sensor 112 is placed to take measurements near and/or from one muscular-walled tube, and the second sensor 114 is placed to take measurements near and/or from another muscular-walled tube. The two muscular-walled tubes may have different features corresponding to different physiological conditions, physiological parameters, and/or physiological constituents. The two muscular-walled tubes may have different features corresponding to a change in a physiological condition, physiological parameter, and/or physiological constituent. For example, one of the muscular-walled tubes may be a vein, and the other muscular-walled tube may be an artery. In general, arteries may carry oxygenated blood, and veins may carry deoxygenated blood. In the embodiments illustrated in FIGS. 3B-C, the arrangements of the sensor may allow for correlation of oxygenated blood to deoxygenated blood. This in turn may inform a determination of a physiological condition, physiological parameter, and/or physiological constituent of a user of the wearable device 100. For example, the wearable device 100 may include the processing unit 110, which may correlate measurements taken by the first sensor 112 and the second sensor 114 placed over the first muscular-walled tube 322 and the second muscular-walled tube 324, respectively, to determine that the blood is not being sufficiently oxygenated.

FIG. 3D illustrates the wearable device 100 with the light source 326, the first sensor 112, and the second sensor 114 being located longitudinally and approximate the first muscular-walled tube 322, according to an embodiment. Some of the features in FIG. 3D are the same as or similar to some of the features in FIGS. 1-3C as noted by same and/or similar reference characters, unless expressly described otherwise. Furthermore, the elements and/or features described regarding FIG. 3D may be the same as and/or similar to other similarly named elements and/or features described and/or illustrated throughout this disclosure. In one embodiment, the first sensor 112 may be located at a first side of a first location along the first muscular-walled tube 322 and the light source(s) 326 may be located on a second side of the first location along the first muscular-walled tube 322, such that the first sensor 112 and the light source(s) 326 straddle each side of the first location along the first muscular-walled tube 322. In another embodiment, the second sensor 114 may be located over a second location along the first muscular-walled tube 322. In another embodiment, the second sensor 114 may include a miniaturized impedance sensor. In one embodiment, the first muscular-walled tube 322 may extend along a Y-axis of a first plane and the miniaturized impedance sensor may extend perpendicularly relative to the first muscular-walled tube 322 along an X-axis of a second plane, such that the miniaturized impedance sensor may extend from a first side of the first muscular-walled tube 322 to a second side of the first muscular-walled tube 322. In one embodiment, the first location along the first muscular walled tube 322 may be located above or ahead of the second location along the first muscular walled tube 322 along the Y-axis. In another embodiment, the first location along the first muscular walled tube 322 may be located below or behind of the second location along the first muscular walled tube 322 along the Y-axis.

FIGS. 3A-D generally show the second sensor 114 aligned with its length parallel to the length of the muscular-walled tubes. Parallel alignment of the second sensor 114 to the muscular-walled tubes may allow for measurements and/or characterization of features running parallel to the length of the muscular-walled tubes. For example, in embodiments where the second sensor 114 includes the miniaturized impedance sensor, the current passed into the user by the miniaturized impedance sensor may run parallel or roughly parallel to the length of the muscular-walled tube to which the miniaturized impedance sensor corresponds. In an embodiment where the muscular-walled tube includes a vein or artery, parallel alignment of the miniaturized impedance sensor may allow for measurement and/or characterization of the blood in the vein or artery along a path of the blood in the vein or artery. Similarly, parallel alignment of the miniaturized impedance sensor may allow for measurement and/or characterization of the muscular-walled tube along the length of the muscular-walled tube.

FIG. 3E illustrates the wearable device 100 with the light source 326, the first sensor 112, and the second sensor 114 being located laterally and approximate the first muscular-walled tube 322, according to an embodiment. Some of the features in FIG. 3E are the same as or similar to some of the features in FIGS. 1-3D as noted by same and/or similar reference characters, unless expressly described otherwise. Furthermore, the elements and/or features described regarding FIG. 3E may be the same as and/or similar to other similarly named elements and/or features described and/or illustrated throughout this disclosure. In one embodiment, the first sensor 112 may be located at a first side of a location along the first muscular-walled tube 322 and the light source(s) 326 may be located on a second side of the location along the first muscular-walled tube 322, such that the first sensor 112 and the light source(s) 326 may straddle each side of the first location along the first muscular-walled tube 322. In another embodiment, the second sensor 114 may be located over the same location along the first muscular-walled tube 322. In another embodiment, the second sensor 114 may include a miniaturized impedance sensor. In one embodiment, the light source 326, the first sensor 112, and the second sensor 114 may extend laterally along the X-axis and perpendicularly to the muscular-walled tube 322. In one embodiment, the second sensor 114 may be located between the light source 326 and the first sensor 112. In another embodiment, the second sensor 114 may be located at an exterior side of the light source 326 or the first sensor 112. In another embodiment, a first portion of the second sensor 114 may be located at an exterior side of the light source 326 and a second portion of the second sensor 114 may be located at an exterior side of the first sensor 112.

Perpendicular alignment of the second sensor 114 to the muscular-walled tubes may allow for measurements and/or characterization of features running perpendicular to the length of the muscular-walled tubes. For example, in embodiments where the second sensor 114 includes the miniaturized impedance sensor, the current passed into the user by the miniaturized impedance sensor may run perpendicular or roughly perpendicular to the length of the muscular-walled tube to which the miniaturized impedance sensor corresponds. In an embodiment where the muscular-walled tube includes a vein or artery, perpendicular alignment of the miniaturized impedance sensor may allow for measurement and/or characterization of a cross-sectional area of the blood in the vein or artery. Similarly, perpendicular alignment of the miniaturized impedance sensor may allow for measurement and/or characterization of the muscular-walled tube along the circumference and/or diameter of the muscular-walled tube.

Figure 3H:
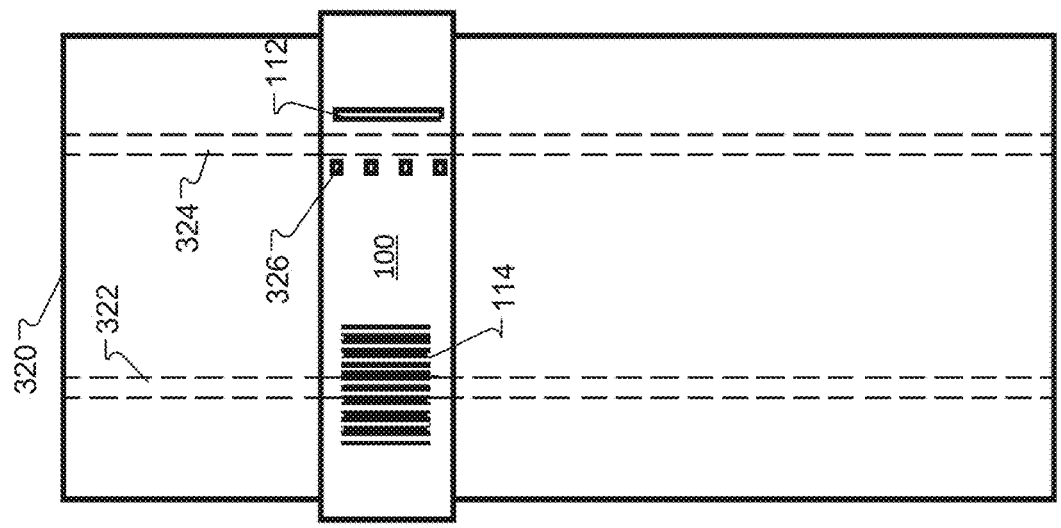
FIG. 3H illustrates the wearable device with the light source and the first sensor being located approximate the second muscular-walled tube and the second sensor being located approximate the first muscular-walled tube, according to an embodiment.
Figure 3G:
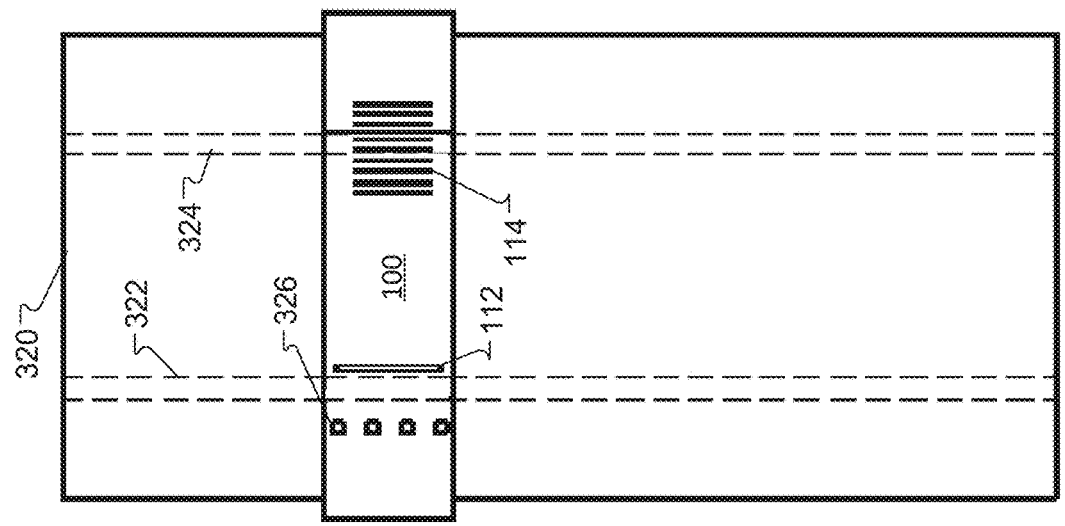
FIG. 3G illustrates the wearable device with the light source and the first sensor being located approximate the first muscular-walled tube and the second sensor being located approximate the second muscular-walled tube, according to an embodiment.
Figure 3F:
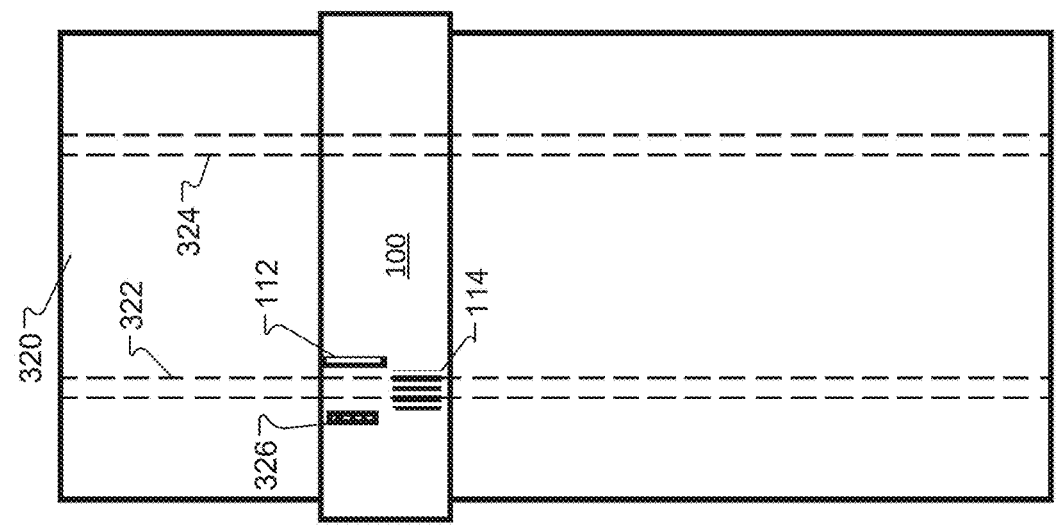
FIG. 3F illustrates the wearable device with the light source, the first sensor, and the second sensor being located in parallel and approximate the first muscular-walled tube, according to an embodiment.

FIG. 3F illustrates the wearable device 100 with the light source 326, the first sensor 112, and the second sensor 114 being located in parallel and approximate the first muscular-walled tube 322, according to an embodiment. Some of the features in FIG. 3F are the same as or similar to some of the features in FIGS. 1-3E as noted by same and/or similar reference characters, unless expressly described otherwise. Furthermore, the elements and/or features described regarding FIG. 3F may be the same as and/or similar to other similarly named elements and/or features described and/or illustrated throughout this disclosure. In one embodiment, the first sensor 112 may be located at a first side of a first location along the first muscular-walled tube 322 and the light source(s) 326 may be located on a second side of the first location along the first muscular-walled tube 322, such that the first sensor 112 and the light source(s) 326 may straddle each side of the first location along the first muscular-walled tube 322. In another embodiment, the second sensor 114 may be located over a second location along the first muscular-walled tube 322. In another embodiment, the second sensor 114 may include a miniaturized impedance sensor. In one embodiment, the first muscular-walled tube 322 may extend along a Y-axis of a first plane and the impedance pad(s) may extend parallel to the first muscular-walled tube 322 along a Y-axis of a second plane, such that the impedance pad(s) extend along a portion of the first muscular-walled tube 322. In one embodiment, the first location along the first muscular walled tube 322 may be located above or ahead of the second location along the first muscular walled tube 322 along the Y-axis. In another embodiment, the first location along the first muscular walled tube 322 may be located below or behind of the second location along the first muscular walled tube 322 along the Y-axis.

FIG. 3G illustrates the wearable device 100 with the light source 326 and the first sensor 112 being located approximate the first muscular-walled tube 322 and the second sensor 114 being located approximate the second muscular-walled tube 324, according to an embodiment. Some of the features in FIG. 3G are the same as or similar to some of the features in FIGS. 1-3F as noted by same and/or similar reference characters, unless expressly described otherwise. Furthermore, the elements and/or features described regarding FIG. 3G may be the same as and/or similar to other similarly named elements and/or features described and/or illustrated throughout this disclosure. In one embodiment, the second sensor 114 may be located over the second muscular-walled tube 324. In one embodiment, the second sensor 114 may include a miniaturized impedance sensor. In one embodiment, the second muscular-walled tube 324 may extend along a Y-axis of a first plane and the miniaturized impedance sensor may extend parallel relative to the second muscular-walled tube 324 along a Y-axis of a second plane, such that the miniaturized impedance sensor may extend along a portion of the second muscular-walled tube 324. In another embodiment, the first sensor 112 may be located at a first side of the first muscular-walled tube 322 and the light source(s) 326 may be located on a second side of the first muscular-walled tube 322, such that the first sensor 112 and the light source(s) 326 may straddle each side of first muscular-walled tube 322.

FIG. 3H illustrates the wearable device 100 with the light source 326 and the first sensor 112 being located approximate the second muscular-walled tube 324 and the second sensor 114 being located approximate the first muscular-walled tube 322, according to an embodiment. Some of the features in FIG. 3H are the same as or similar to some of the features in FIGS. 1-3G as noted by same and/or similar reference characters, unless expressly described otherwise. Furthermore, the elements and/or features described regarding FIG. 3H may be the same as and/or similar to other similarly named elements and/or features described and/or illustrated throughout this disclosure. In one embodiment, the second sensor 114 may be located over the first muscular-walled tube 322. In one embodiment, the second sensor 114 may include a miniaturized impedance sensor. In one embodiment, the second muscular-walled tube 324 may extend along a Y-axis of a first plane and the miniaturized impedance sensor may extend parallel relative to the first muscular-walled tube 322 along a Y-axis of a second plane, such that the miniaturized impedance sensor may extend along a portion of the second muscular-walled tube 324. In another embodiment, the first sensor 112 may be located at a first side of the second muscular-walled tube 324 and the light source(s) 326 may be located on a second side of the second muscular-walled tube 324, such that the first sensor 112 and the light source(s) 326 may straddle each side of second muscular-walled tube 324.

Figure 3I:
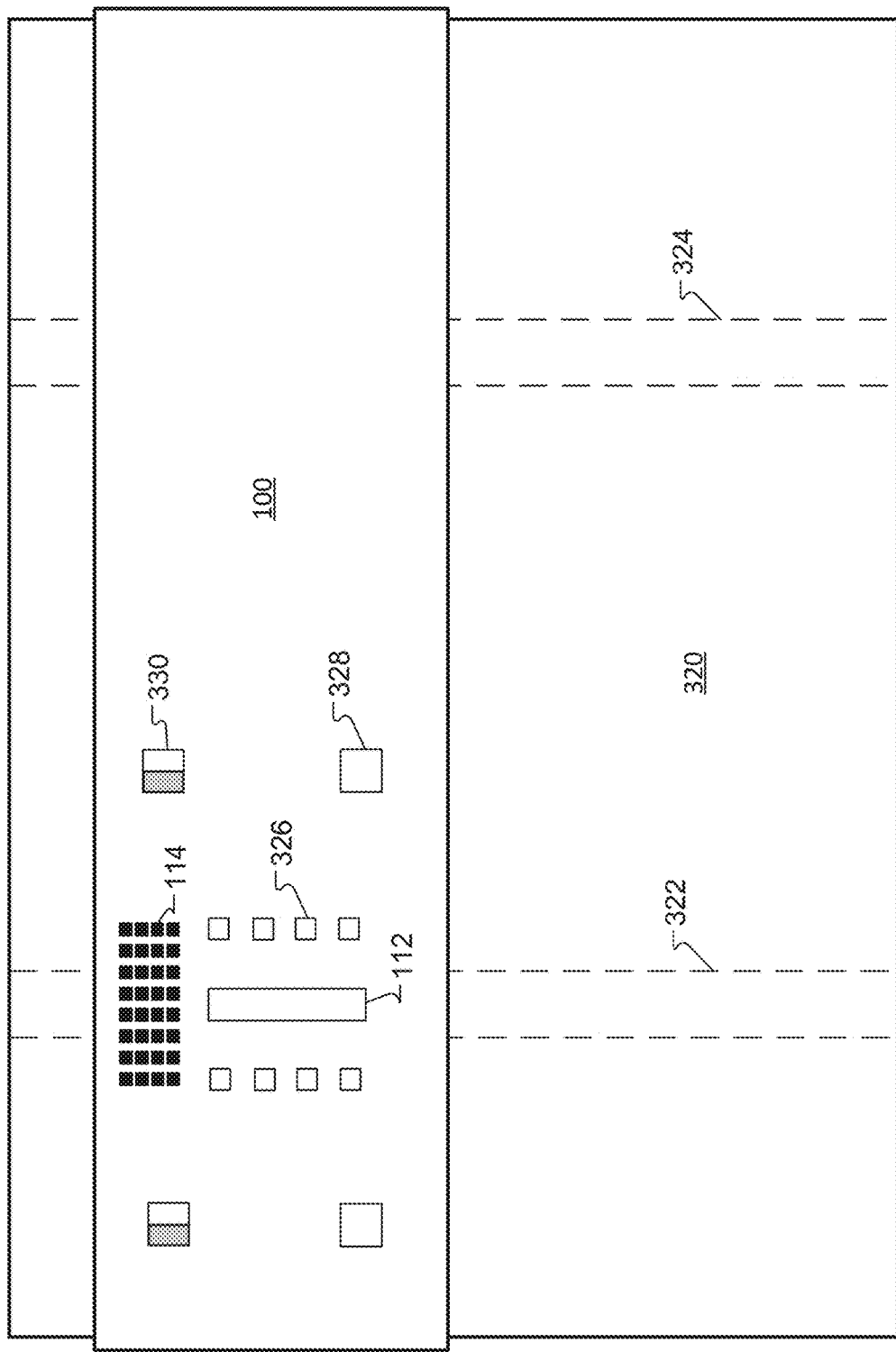
FIG. 3I illustrates a sensor array for aligning the first sensor, the light source, and/or the second sensor with the muscular-walled tube, according to an embodiment.

FIG. 3I illustrates a sensor array for aligning the first sensor 112, the light source 326, and/or the second sensor 114 with the muscular-walled tube, according to an embodiment. Some of the features in 3I are the same as or similar to some of the features in FIGS. 1-3H as noted by same reference characters, unless expressly described otherwise. The sensor array may include a a photosensor or a light sensor 328 and a light emitter 330. The light sensor 328 and the light emitter 330 may form an alignment device which may be configured to enable a user to align the first sensor 112 or the second sensor 114 with the muscular-walled tube 322 or 324. In an embodiment, the light sensor 328 may include a photodiode. In an embodiment, the light emitter 330 may include a dual band light emitter. In an embodiment, the light emitter 330 may include two LEDs emitting different wavelengths of light from each other. For example, a first of the LEDs may emit red light with a wavelength of approximately 660 nm, and a second of the LEDs may emit infrared light with a wavelength of approximately 940 nm. The sensor array may be coupled to the processing device 102 of the wearable device 100. The sensor array may straddle the first sensor 112, the light source 326, and/or the second sensor 114. For example, the two light sensors 328 may be disposed on opposite sides of the first sensor 112, the light source 326, and/or the second sensor 114 from each other. Similarly, the two light emitters 330 may be disposed on opposite sides of the first sensor 112, the light source 326, and/or the second sensor 114 from each other. In an embodiment, the sensor array may straddle the muscular-walled tube 322.

The processing device 102 may include instructions for taking oxygen saturation levels using the sensor array. Light emitted by the light emitter 330 may be detected by the light sensor 328. The light detected by the light sensor 328 may correspond to an amount of oxygenated hemoglobin in the tissue adjacent to the light emitter 330 and the light sensor 328. A greater amount of oxygenated hemoglobin detected by the light sensor 328 may indicate the light sensor 328 and the light emitter 330 are more closely positioned to the muscular-walled tube 322. In an embodiment, the sensor array may include a set of two light sensors 328 and a set of two light emitters 330. A combined signal from the set of two light sensors 328 may indicate an alignment with the muscular-walled tube 322. For example, the processing device 102 may store instructions to compare signals from the two light sensors 328. When the signal from one of the two light sensors 328 is equal to the signal from another of the two light sensors 328, the processing device 102 may provide an indication to a user, such as via the display device 104, that the wearable device 100 is properly aligned on the part of the body 320.

In one example, the alignment device may be embedded in a band of the wearable device around the first sensor 112, the light source 326, and/or the second sensor 114. The alignment device may include a first dual-band light emitter 330 positioned in the band at a first corner about the first sensor 112, the light source 326, and/or the second sensor 114; a second dual-band light emitter 330 positioned in the band at a second corner about the first sensor 112, the light source 326, and/or the second sensor 114; a first photosensor 328 positioned in the band at a third corner about the first sensor 112, the light source 326, and/or the second sensor 114; and a second photosensor 328 positioned in the band at a fourth corner about the first sensor 112, the light source 326, and/or the second sensor 114.

In another example, the first dual-band light emitter 330 may be positioned in the band to be situated along a first side of the muscular-walled tube as the user wears the band; the second dual-band light emitter 330 may be positioned in the band to be situated along a second side of the muscular-walled tube as the user wears the band; the first photosensor 328 may be positioned in the band to be situated along the first side of the muscular-walled tube as the user wears the band; and the second photosensor 328 may be positioned in the band to be situated along the first side of the muscular-walled tube as the user wears the band. In another example, the first dual-band light emitter 330 and the second dual-band light emitter 330 may be positioned in the band to be situated along the first side of the muscular-walled tube as the user wears the band; and the first photosensor 328 and the second photosensor 328 may be positioned in the band to be situated along the second side of the muscular-walled tube as the user wears the band.

As shown in FIGS. 3A-H, the second sensor 114 may include miniaturized electrode strips. As shown in FIG. 3I, the second sensor 114 may include electrode dots. The electrode dots may allow for more precise tuning of a signal to noise ratio of measurements taken by the second sensor 114. Accordingly, in some embodiments where variability of the signal to noise ratio may be large, it may be advantageous to manufacture the second sensor 114 with electrode dots. Software of a processor coupled to the second sensor 114 may analyze signal quality of a variety of combinations of dots and select the pairs of dots with the highest signal quality. The electrode strips may be simple to manufacture and/or may require less manufacturing time and/or precision. The electrode dots may include a dot surface that may contact the body part. A surface of the dot may be approximately equal in length and width dimensions.

Accordingly, in some embodiments where manufacturing considerations weigh heavy, it may be advantageous to manufacture the second sensor 114 with electrode strips. In one example, the electrode strip may have a strip surface that contacts the body part. In another example, the strip surface may include a length dimension that is greater than a width dimension of the strip surface.

In one embodiment, a strip of the electrode strips may have a length longer than a width or a thickness of the strip. In one example, a contact surface of the single strip for contacting a body part may be formed by the length and the width. In another example, a thickness of the strip may be situated in the band to extend from the band towards the wrist as the user wears the wearable device.

Figure 4A:
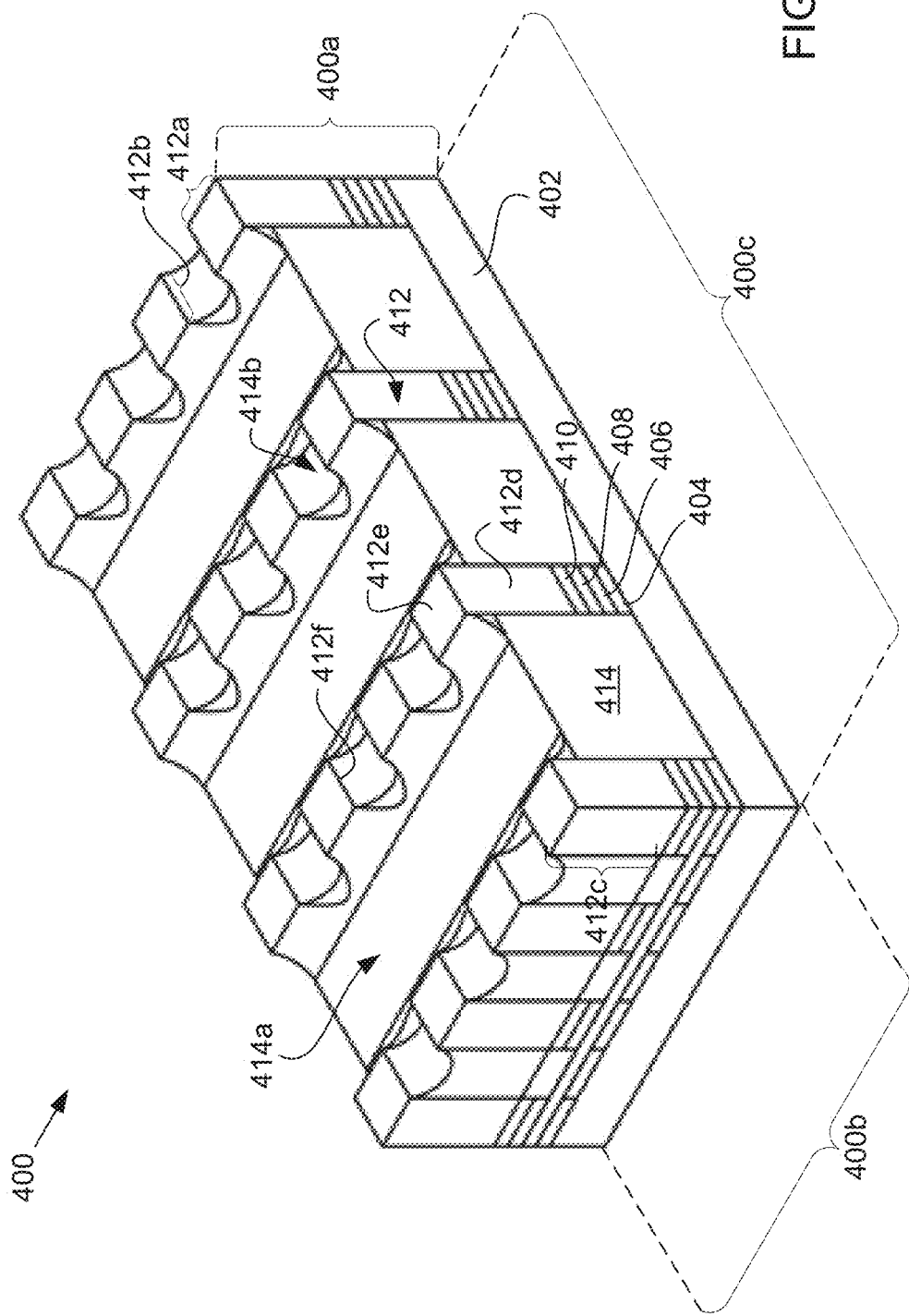
FIG. 4A illustrates a perspective view of a miniaturized impedance sensor with an interstitial filler distributed between miniaturized electrodes, according to an embodiment.

FIG. 4A illustrates a perspective view of a miniaturized impedance sensor 400 with an interstitial filler 414 distributed between miniaturized electrodes 412, according to an embodiment. Some of the features in FIG. 4A are the same as or similar to some of the features in FIGS. 1-3I as noted by same and/or similar reference characters, unless expressly described otherwise. The miniaturized impedance sensor 400 may include a growth substrate 402, a first insulating layer 404, a conductive layer 406, a second insulating layer 408, a catalyst layer 410, the miniaturized electrode 412, and/or the interstitial filler 414, which elements may be the same as and/or similar to other similarly-named elements described and/or illustrated throughout this disclosure. In an embodiment, the miniaturized impedance sensor 400 may include one or more of the growth substrate 402, the first insulating layer 404, the conductive layer 406, the second insulating layer 408, the catalyst layer 410, the miniaturized electrode 412, and/or the interstitial filler 414.

For example, the miniaturized impedance sensor 400 may include a plurality of miniaturized electrodes 412.

The miniaturized impedance sensor 400 may be incorporated into an electronic device. In various other embodiments, the miniaturized impedance sensor 400 may be incorporated into a wearable such as a wristband, an armband, a brace such as a knee brace, an ankle brace, an elbow brace, a neck brace, a wrist brace, and/or a back brace, a shirt, a pair of shorts, a pair of pants, a sleeve, a hat, a hardhat, an undergarment, a belt, a pack such as a backpack and/or a fanny pack, headphones, and so forth. In an embodiment, the miniaturized impedance sensor 400 may be incorporated into a wearable device similar to the wearable device 100 described regarding FIG. 1. For example, the second sensor 114 of the wearable device 100 may include the miniaturized impedance sensor 400. In various embodiments, the miniaturized impedance sensor 400 may be incorporated into a health monitoring device. The health monitoring device may be positioned against a user of the health monitoring device to take one or more biometric measurements of the user. In an embodiment, the health monitoring device may be attached to the user, such as by an adhesive tape, a therapeutic kinesiology tape, an adhesive bandage, an elastic bandage, a liquid bandage, a gauze bandage, a compression bandage, a cravat bandage, a tube bandage, and so forth. The health monitoring device may include a variety of sensors, such as an optical sensor and a bio impedance sensor. In an embodiment, the health monitoring device may include the miniaturized impedance sensor 400 held against the user by an adhesive tape and electrically coupled to a computing device. The computing device may include logic, a processor, memory, and/or a user interface for communicating measurements by the miniaturized impedance sensor to a person such as a healthcare professional, and which may allow the person to control the miniaturized impedance sensor 400.

In various embodiments, the miniaturized impedance sensor 400 may be implemented in other than wearable-device implementations. For example, in an embodiment, the miniaturized impedance sensor 400 may coupled to a hydraulic system. The miniaturized impedance sensor may be attached to a surface that encloses hydraulic fluid to measure a quality and/or integrity of the hydraulic fluid within the enclosure. In an embodiment, the miniaturized impedance sensor 400 may be incorporated into a device for inspecting welds and/or other fabricated materials and/or surfaces. In general, the miniaturized impedance sensor 400 may be used for determining a static and/or dynamic quality of a surface and/or volume of material in a non-invasive way.

The miniaturized impedance sensor 400 may be formed in a layered and/or roughly layered format. As used throughout this disclosure, "layered" may refer to a structure that includes layers of material stacked one on top of the other in an order. Accordingly, "roughly" layered may refer to a structure having layers of material stacked one on top of the other, but the layers may include discontinuities, alternating of the order, and/or mixing of layers. Though layers of the miniaturized impedance sensor 400 may be described in a certain order and/or format, such description is not intended to be limiting. For example, the first insulating layer 404 may be disposed between the growth substrate 402 and the conductive layer 406 in one embodiment. In another embodiment the first insulating layer 404 may be integrated with the growth substrate 402 to be indistinguishable from the growth substrate 402, and the conductive layer 406 may be layered on the integrated growth substrate 402/first insulating layer 404. In another embodiment, the first insulating layer 404 may be disposed between the catalyst layer 410 and the miniaturized electrode 412. In an embodiment, the miniaturized impedance sensor 400 may include the growth substrate 402 layered underneath the first insulating layer 404. The conductive layer 406 may be patterned on the first insulating layer 404. The second insulating layer 408 may be deposited over the conductive layer 406. The catalyst layer 410 may be patterned on the second insulating layer 408. The miniaturized electrode 412 may be grown on the catalyst layer 410. The interstitial filler 414 may be deposited on the second insulating layer 408 surrounding the miniaturized electrode 412.

In one embodiment, the conductive layer 406 may be patterned, where the conductive layer pattern includes regions of conductive material adjacent to regions of non-conductive material. The regions of conductive material may be spaced from each other to prevent capacitive coupling and arcing between the regions of conductive material. In one example, the interstitial filler 414 may include a top side and a bottom side. The substrate 402 or the patterned conductive layer 406 may be disposed at the bottom side of the interstitial filler 414. In another example, a patterned array of miniaturized electrodes 412 may extend through a volume from the bottom side to the top side of the interstitial filler 414.

In various embodiments, elements of the miniaturized impedance sensor 400 shown in FIGS. 4A-C may be omitted. For example, the growth substrate 402 and/or the first insulating layer 404 may be omitted in an embodiment. In an embodiment where the growth substrate 402 and/or the first insulating layer 404 may be omitted, the miniaturized impedance sensor 400 may include the conductive layer 406, the second insulating layer 408, the catalyst layer 410, the miniaturized electrode 412, and/or the interstitial filler 414. These elements may be integrated with another substrate such as a PCB and/or a flexible substrate with electrical traces. In one embodiment, the miniaturized impedance sensor 400 may include the growth substrate 402, the conductive layer 406, the second insulating layer 408, the catalyst layer 410, the miniaturized electrode 412, and/or the interstitial filler 414, and may omit the first insulating layer 404. In another embodiment, the miniaturized impedance sensor 400 may include the growth substrate 402, the first insulating layer 404, the conductive layer 406, the catalyst layer 410, the miniaturized electrode 412, and/or the interstitial filler 414, and may omit the second insulating layer 408. In an embodiment, the miniaturized impedance sensor 400 may include the growth substrate 402, the first insulating layer 404, the conductive layer 406, the second insulating layer 408, the miniaturized electrode 412, and/or the interstitial filler 414, and may omit the catalyst layer 410. In an embodiment, the miniaturized impedance sensor 400 may include the growth substrate 402, the first insulating layer 404, the conductive layer 406, the second insulating layer 408, and/or the miniaturized electrode 412 and may omit the interstitial filler 414.

In various embodiments, the elements of the miniaturized impedance sensor 400 may be provided in a different order and/or may be provided and/or consumed at different stages of a manufacturing process of the miniaturized impedance sensor 400. For example, miniaturized electrode 412 may be grown on the growth substrate 402 by laying the medial insulating layer 408 and the catalyst layer 410 on the growth substrate 402. The miniaturized electrodes 412, the medial insulating layer 408, and/or the catalyst layer 410 may be released from the growth substrate 402 and the medial insulating layer 408 may be etched away. The conductive layer 406 may be adhered to the miniaturized electrode 412, such as by a conductive adhesive. Various embodiments and/or arrangements may be selected based on resulting durability of the miniaturized impedance sensor 400, manufacturing constraints, electrical performance of the miniaturized impedance sensor 400, adhesion of the elements of the miniaturized impedance sensor 400, and so forth.

FIG. 4B illustrates a head-on view of a first side of the miniaturized impedance sensor 400 illustrated in FIG. 4A, according to an embodiment. Some of the features in FIG. 4B are the same as or similar to some of the features in FIGS. 1-4A as noted by same and/or similar reference characters, unless expressly described otherwise. In various embodiments, the miniaturized impedance sensor 400 may include one or more dimensions and/or surfaces. For example, the miniaturized impedance sensor 400 may include a back side 416 and a user side 418. The user side 418 may include electrical pads. The electrical pads may be formed by a plurality miniaturized electrodes 412, in one embodiment. The user side 418 of the miniaturized impedance sensor 400 may be positioned in the wearable device to face a user wearing the wearable device. The user side 418 of the miniaturized impedance sensor 400 may be positioned in the wearable device to press against a skin surface of the user when the user wears the wearable device. The back side 416 of the miniaturized impedance sensor 400 may be disposed on the miniaturized impedance sensor 400 opposite the user side 418. The back side 416 may be positioned in the wearable device to form electrical contact between the miniaturized impedance sensor 400 and electronics of the wearable device. The back side 416 may include conductors to form such electrical contact. In an embodiment, the conductors may include the conductive layer 406. In an embodiment, the conductors may include patterned nickel leads. The miniaturized impedance sensor 400 may include a depth side 420. The depth side 420 of the miniaturized impedance sensor 400 may be aligned perpendicular to the user side 418 or the back side 416. In an embodiment, the depth side 420 may be positioned in the wearable device to form the electrical contact between the miniaturized impedance sensor 400 and the electronics of the wearable device. The depth side 420 may include conductors to form such electrical contact. The conductors may include, in an embodiment, soldering electrically coupled to the conductive layer 406.

The miniaturized impedance sensor 400 may include a height 400*a*, a width 400*b*, and/or a length 400*c*. The height 400*a* may range from 200 micrometers (microns) to 1000 microns, from 300 microns to 800 microns, and/or from 400 microns to 600 microns. In an embodiment, the height 400*a* may be 500 microns. The length 400*c* may range from 2 millimeters (mm) to 10 mm, from 3 mm to 8 mm, and/or from 4 mm to 6 mm. In an embodiment, the width 400*b* may be 500 microns. The length 400*c* may range from 6 mm to 40 mm, from 10 mm to 35 mm, from 15 mm to 30 mm, and/or from 20 mm to 25 mm. In an embodiment, the length 400*c* may be 2 mm. In an embodiment, the miniaturized impedance sensor 400 may be structured and/or configured, such as by the dimensions described above, to occupy a volume ranging from 0.04 cubic millimeters to 20 cubic millimeters. In various embodiments the miniaturized impedance sensor 400 may be configured to occupy a volume ranging from 0.01 cubic millimeters to 0.04 cubic millimeters.

The growth substrate 402 may provide a base support structure for deposition, growth, and/or etching of various microstructures. The microstructures may include the first insulating layer 404, the conductive layer 406, the second insulating layer 408, the catalyst layer 410, the miniaturized electrode 412, or the interstitial filler 414. In general, the growth substrate 402 may have low surface roughness, such as less than or equal to 1 nanometer (nm). The growth substrate 402 may be configured to withstand infiltration of various materials at temperatures ranging up to 1000° C., up to 900° C., and/or up to 850° C. The various materials may include materials from which the microstructures are formed, such as alumina, nickel, iron, carbon, and so forth. In one embodiment, the growth substrate 402 may include a silicon wafer. In another embodiment, the growth substrate 402 may include a tungsten wafer. In yet another embodiment, the growth substrate 402 may include glass such as a borosilicate glass.

In various embodiments, the growth substrate 402 may be removed after preparation of the miniaturized impedance sensor 400 and before the miniaturized impedance sensor 400 is incorporated into the wearable device. In one embodiment, one or more of the microstructures may be deposited, grown, and/or etched on the growth substrate 402, and then removed from the growth substrate 402 to be integrated into the wearable device. For example, the microstructures may be removed from the growth substrate 402 and adhered to a flexible substrate for incorporation into the wearable device. In another embodiment, the growth substrate 402 may be a reusable substrate that may be used in multiple miniaturized impedance sensor preparations. For example, the growth substrate 402 may be an element of an intermediary state of the miniaturized impedance sensor 400 between preparation of the miniaturized impedance sensor 400 and incorporation of the miniaturized impedance sensor 400 into the wearable device. Such an embodiment may be described and/or illustrated in more detail regarding FIG. 8.

In various embodiments, the growth substrate 402 may be incorporated with the miniaturized impedance sensor 400 into the wearable device. For example, the growth substrate 402 may act as a support substrate used to incorporate the miniaturized impedance sensor 400 with other electronics of the wearable device. The growth substrate 402 may include soldered leads which may be electrically coupled to the conductive layer 406 of the miniaturized impedance sensor 400. The soldered leads may electrically couple the conductive layer 406 to electrical traces in the wearable device. An example of such an embodiment may be described and/or illustrated in further detail regarding FIG. 9.

The first insulating layer 404 may provide electrical and/or thermal insulation between the growth substrate 402 and other microstructures of the miniaturized impedance sensor 400. The first insulating layer 404 may prevent diffusion of microstructure materials, such as nickel in the conductive layer 406, into the growth substrate 402 during high temperature growth of the miniaturized electrode 412, where the high temperatures may range from 700° C. to 1000° C. Additionally, the first insulating layer 404 may include a material susceptible to removal by a plasma and/or chemical etch to expose the conductive elements of the miniaturized impedance sensor 400 for integration into circuitry. Alternatively, the first insulating layer 404 may include a material that is rendered conductive by one or more processes and/or conditions during manufacture of the miniaturized impedance sensor 400. For example, alumina may be rendered conductive after exposure to temperatures at which the miniaturized electrode 412 may be grown.

In one embodiment, the first insulating layer 404 may include aluminum oxide ("alumina"). In another embodiment, the first insulating layer 404 may include tungsten. The first insulating layer 404 may be deposited on and/or otherwise affixed to the growth substrate 402. For example, the first insulating layer 404 may be deposited on the growth substrate 402 by sputtering and/or electron beam deposition. Accordingly, a thickness of the first insulating layer 404 may range from a few nm to a few microns. The first insulating layer 404 may cover an area of the growth substrate 402's growth surface corresponding to a set of the microstructures. The set of microstructures may be disposed on the first insulating layer over the area of the growth surface. The set of microstructures may include the conductive layer 406, the catalyst layer 410, or the miniaturized electrode 412. The growth substrate 402 may include a set of first insulating layers 404, and each set of first insulating layers 404 may include a set of the microstructures.

The conductive layer 406 may provide conductive electrical connection between the miniaturized electrode 412 and the wearable device. For example, the conductive layer 406 may be electrically coupled to electrical traces in the wearable device. Alternatively, the conductive layer 406 may be electrically coupled to leads on a printed circuit board (PCB). The conductive layer 406 may be electrically coupled to a PCB by solder bridging the conductive layer 406 to electrical leads coupled to electrical traces in the PCB. In general, the conductive layer 406 may be electrically conductive, may easily delaminate from the growth substrate after growth of the miniaturized electrode 412, and/or may have other properties favorable to fabrication and/or manufacturing such as solderability. In various embodiments, the conductive layer 406 may include nickel, nickel oxide, chromium, stainless steel, aluminum gold, nickel platinum, chromium gold, and so forth. In one embodiment, nickel may have an advantage of being solderable. In another embodiment, the chromium gold may have an advantage being easily released from a silicon wafer.

The conductive layer 406 may be deposited by one or more physical vapor deposition methods such as sputtering deposition and/or evaporation deposition. The conductive layer 406 may be deposited on the first insulating layer 404, then patterned. The patterning may be accomplished by optical lithography, lift-off, and/or etching for pattern transfer.

The conductive layer 406 may have regions of conductive material, which may be referred to as a positive region 422a. The conductive layer 406 may have regions without material, which may be referred to as a negative region 422b. The positive region 422a may have a dimension such as an area, and the negative region 422b may have a dimension such as an area. The negative region 422b area may encompass a large enough volume and/or surface area to electrically isolate neighboring positive regions 422a from each other for amperages and/or potentials up to a maximum level for the device. The maximum current and/or voltage may be the same as and/or similar to that discussed regarding FIGS. 15A-B. The negative region 422b area may encompass a large enough volume and/or surface area to electrically isolate each miniaturized electrode 412 from each other miniaturized electrode 412. For example, the negative region 422b may have an area ranging from 0.025 mm$^2$ to 1 mm$^2$. In another example, the negative regions 422b and the positive regions 422a may form two patterns are aligned to form positive regions 422a that are conductive regions and negative regions 422b that are non-conductive regions. The non-conductive regions electrically may isolate the conductive regions from each other.

The second insulating layer 408 may contribute to and/or enhance growth of the miniaturized electrode 412. Accordingly, the second insulating layer 408 may be complimentary to the catalyst layer 410. The second insulating layer 408 may provide a barrier between the catalyst layer 410 and the growth substrate 402 and/or the conductive layer 406 to prevent infiltration of the layers into each other. The second insulating layer 408 may be rendered conductive by one or more conditions and/or processes during growth of the miniaturized electrode 412. In various embodiments, the second insulating layer 408 may include alumina.

The catalyst layer 410 may provide structural support and/or chemical reactiveness to stimulate and/or catalyze growth of the miniaturized electrode 412. The catalyst layer 410 may be conductive to allow for electrical conduction between the miniaturized electrode 412 and the conductive layer 406. In various embodiments, the catalyst layer 410 may include iron, cobalt, and/or molybdenum. The catalyst layer 410 may be deposited on the second insulating layer 408 over the conductive layer 406. The catalyst layer 410 may be deposited by a physical vapor deposition technique. In various embodiments, the catalyst layer 410 may be deposited by sputtering and/or evaporation deposition.

FIG. 4C illustrates a head-on view of a second side of the miniaturized impedance sensor 400 illustrated in FIG. 4A, according to an embodiment. Some of the features in FIG. 4C are the same as or similar to some of the features in FIGS. 1-4B as noted by same and/or similar reference characters, unless expressly described otherwise. As discussed previously, various layers of the miniaturized impedance sensor 400 may be patterned on a preceding layer. A pattern may include the positive region 422a and the negative region 422b. The positive region 422a may include material of a patterned layer. The negative region 422b may lack material of the patterned layer. The first insulating layer 404, the conductive layer 406, the second insulating layer 408, the catalyst layer 410, and/or the miniaturized electrode 412 may be patterned. As used throughout this disclosure, "positive" may refer to a region of a layer pattern where the layer includes material, and "negative" may refer to a region of the layer pattern where the layer lacks material. For example, as illustrated in FIG. 4C, the conductive layer 406 may be positive where other layers, such as the first insulating layer 404, the second insulating layer 408, the catalyst layer 410, and/or the miniaturized electrode 412, are negative. In another example, as illustrated in FIG. 4B, the conductive layer 406 may be positive where other layers, such as the first insulating layer 404, the second insulating layer 408, the catalyst layer 410, and/or the miniaturized electrode 412, are positive, and the conductive layer 406 may be negative where other layers, such as the first insulating layer 404, the second insulating layer 408, the catalyst layer 410, and/or the miniaturized electrode 412, are negative. In an embodiment, one or more of the first insulating layer 404, the conductive layer 406, the second insulating layer 408, the catalyst layer 410, and the miniaturized electrode 412 may be patterned similar to each other. For example, positive regions of various layers, such as the first insulating layer 404, the conductive layer 406, the second insulating layer 408, the catalyst layer 410, or the miniaturized electrode 412, may be aligned. In another embodiment, various layers, such as the first insulating layer 404, the conductive layer 406, the second insulating layer 408, the catalyst layer 410, or the miniaturized electrode 412, may be misaligned.

In an embodiment, the miniaturized electrode 412 may be aligned perpendicular to the growth substrate 402. In an embodiment, the miniaturized electrode 412 may include a bundle of nanotubes running roughly along the length 400c. The bundle may be infiltrated with a bolstering material, where "bolster" may refer to a property of a material that increases resistance against an applied force of the material and/or another material with which the material is incorporated. Accordingly, the bolstering material may increase the rigidity of the bundle relative to similarly structured bundles not including the bolstering material. The bolstering material may reduce the brittleness of the bundle relative to similarly structured bundles not including the bolstering material. In various embodiments, the nanotubes may include Carbon Nanotubes (CNTs). The bolstering material may include carbon and/or a conductive polymer. In one embodiment, the miniaturized electrode 412 may include CNTs infiltrated with carbon. In another embodiment, the nano electrode 412 may include CNTs infiltrated with a conductive polymer. In another embodiment, the miniaturized electrode 412 may include a polymer coated with a conductive film. The conductive film may include a thin film. The thin film may include metal and/or carbon. In an embodiment, the polymer may be formed into a pillar.

In one embodiment, the miniaturized electrode 412 may include an array of pillars, such as miniaturized electrode pillars. In one example, the pillar may have a width 412a and a length 412b that define a top surface area of a pillar. In one embodiment, the width 412 and the length 412b may be the same. In another embodiment, the width 412a and the length 412b may be different. The array of pillars may include a first row of miniaturized electrode pillars positioned in a band or a wearable device to be aligned approximately perpendicular with a diameter of a muscular-walled tube as the user wears the band; and a second row of miniaturized electrode pillars positioned in the band to be aligned approximately perpendicular with the diameter of the muscular-walled tube as the user wears the flexible band. In one example, the first row of miniaturized electrode pillars may be positioned against the dermal layer along the first side of the muscular-walled tube as the user wears the band and the second row of miniaturized electrode pillars may be positioned against the dermal layer along the second side of the muscular-walled tube as the user wears the band. In another example, the first row of miniaturized electrode pillars may be configured in the flexible band to be positioned against a segment of the dermal layer as the user wears the band. The segment of the dermal layer may be directly adjacent to the muscular-walled tube such that, as the user wears the band, the portion of the dermal layer is situated between the first row of miniaturized electrode pillars and the muscular-walled tube.

In another example, the array of miniaturized electrode pillars may include a first row of pillars and a second row pillars. The first row of pillars and the second row of pillars may be are configured such that the electrical signal travels from the first row to the second row. For example, the first row of pillars may include a first pillar and a second pillar and the second row of pillars may include a third pillar and a fourth pillar. In one embodiment, the first pillar and the third pillar may be positioned in the band to be situated against the dermal layer along a first side of the muscular-walled tube as the user wears the band. In another embodiment, the second pillar and the fourth pillar are positioned in the band to be situated against the dermal layer along a second side of the muscular-walled tube as the user wears the band.

In another embodiment, a single pillar of the array of miniaturized electrode pillars comprising a height greater than a length or a width. In one example, a contact surface of the single pillar may be a dot defined by the width 412a and the length 412b. In another example, a height 412c of the pillar may extend from a band towards the wrist as the user wears the wearable device 100.

According to one embodiment, the interstitial filler 414 may be positioned between rows and/or columns of microstructures on the growth substrate 402. In an embodiment, the interstitial filler 414 may be deposited on the second insulating layer 408. The interstitial filler 414 may fill a region between separate miniaturized electrodes 412. In another embodiment, the interstitial filler 414 may be deposited on the growth substrate 402 along a first inter-columnar region and may be deposited on the second insulating layer 408 along a second inter-columnar region. The interstitial filler 414 may be deposited against and/or on the miniaturized electrode 412. For example, the interstitial filler 414 may be deposited against a side surface 412d of the miniaturized electrode 412. The interstitial filler 414 may adhere to the side surface 412d. The interstitial filler may be deposited against a top surface 412e of the miniaturized electrode 412. The interstitial filler 414 may adhere to the top surface 412e. In an embodiment, the interstitial filler 414 may include wells 414a and 414b between neighboring miniaturized electrodes 412. In an embodiment, the wells 414a and/or 414b may be rounded, squared, u-shaped, and/or v-shaped. In an embodiment, a top surface 414c of the interstitial filler 414 may be disposed against top edges 412f of the miniaturized electrode 412, in an embodiment. The topmost surface may be sloped away from the top edges along the height 412c of the miniaturized electrode 412. In one example, the wells 414a may dip away from a first miniaturized electrode or a second miniaturized electrode of the neighboring miniaturized electrodes 412 towards the growth substrate 402. In another example, the interstitial filler 414 may include a first top surface where the first top surface forms a well 414a that dips from a first horizontal plane down to a second horizontal plane. The miniaturized electrodes 412 may include a second top surface. The second top surface may be flush with the first horizontal plane and an edge of the first top surface of the interstitial filler 414 may be flush with an edge of the second top surface of the miniaturized electrodes 412.

In conventional impedance sensor, breakage of electrodes, may cause the impedance sensor to malfunction, such as by causing a short in the impedance circuit. Additionally, depending on a material the electrodes are made of, breakage of the electrodes may cause physiological harm to a user of the impedance sensor. In an extreme example, long-term exposure may lead to disease such as mesothelioma. However, features of the miniaturized impedance sensor 400 may prevent such risk, such as infiltration of the CNTs with the bolstering material and/or reinforcement of the miniaturized electrode 412 with the interstitial filler 414. The interstitial filler 414 may bolster the miniaturized electrode 412 to prevent breakage of the miniaturized electrode 412. The interstitial filler 414 may protect the miniaturized electrode 412 from torque that may otherwise bend and/or break the miniaturized electrode 412. The interstitial filler 414 may be rigid and/or flexible in an embodiment. The interstitial filler 414 may be compressible. In general the interstitial filler 414 may include a polymer such as an epoxy. In one embodiment, the interstitial filler 414 may include polyimide.

Figure 5A:
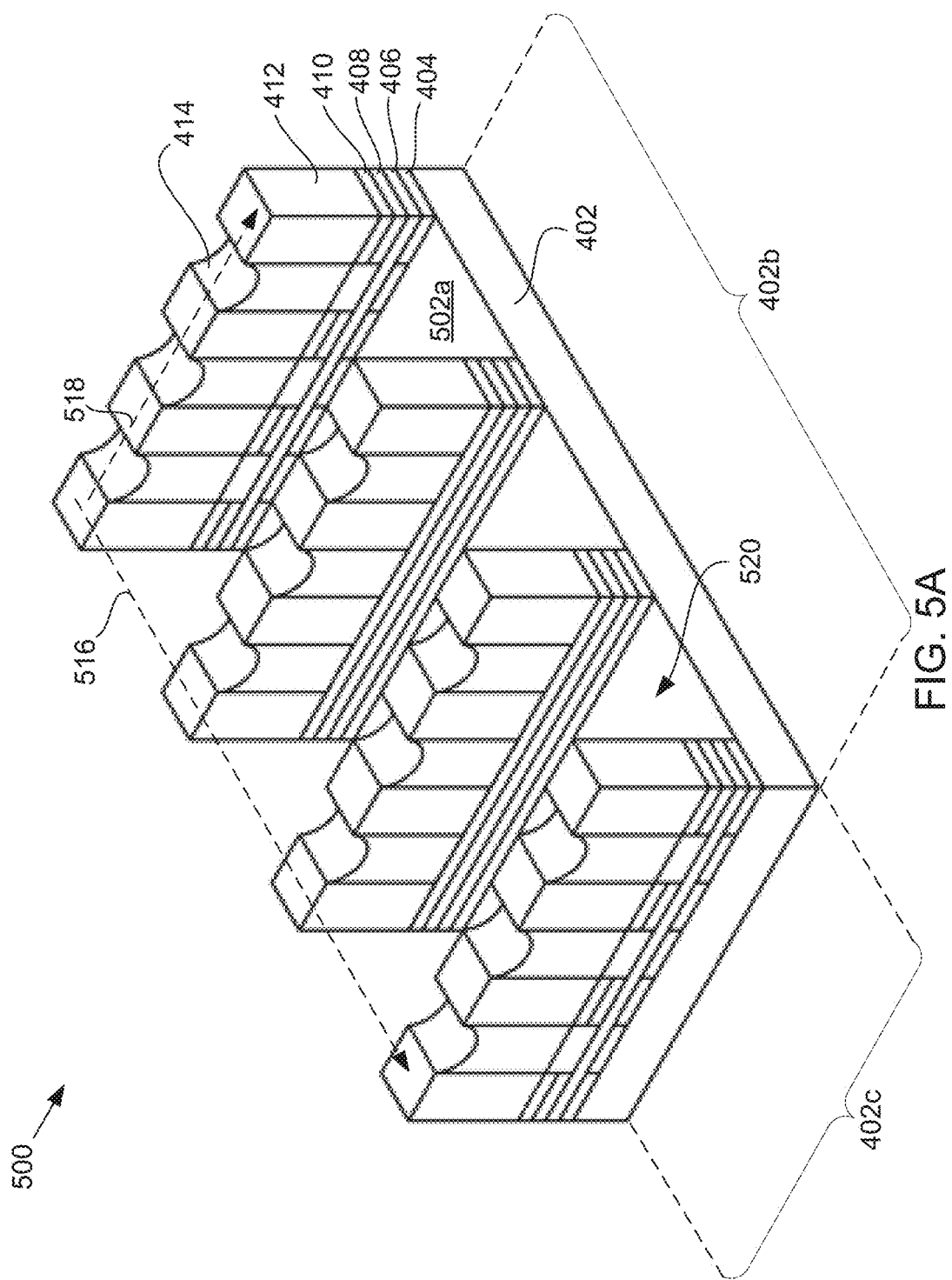
FIG. 5A illustrates a perspective view of the miniaturized impedance sensor with an interstitial filler disposed between miniaturized electrodes in a row, according to an embodiment.

FIG. 5A illustrates a perspective view of the miniaturized impedance sensor 400 with the interstitial filler 414 disposed between neighboring miniaturized electrodes 412 in a row, according to an embodiment. Some of the features in FIG. 5A are the same as or similar to some of the features in FIGS. 1-4C as noted by same and/or similar reference characters, unless expressly described otherwise. The miniaturized impedance sensor 400 may include the growth substrate 402 and/or the first insulating layer 404 on which various microstructures may be deposited, grown, and/or otherwise disposed. The growth substrate 402 and/or first insulating layer 404 may be the same as or similar to other similarly named elements described and/or illustrated throughout this disclosure. The microstructures may include the conductive layer 406, the second insulating layer 408, the catalyst layer 410, the miniaturized electrode 412, and/or the interstitial filler 414, which elements may be the same as or similar to other similarly named elements described and/or illustrated throughout this disclosure. The microstructures may be layered on the growth substrate 402. In one embodiment, the microstructures may be arranged in columns 516 and/or rows 518. The interstitial filler 414 may be disposed on the second insulating layer 408 between neighboring miniaturized electrodes 412 along the same row 518. At least a portion of a growth surface 502a of the growth substrate 402 may remain exposed. In an embodiment, the growth surface 502a may be defined by the length 402b and/or the width 402c of the growth substrate 402.

FIG. 5B illustrates a head-on view of a first side of the miniaturized impedance sensor 400, according to an embodiment. Some of the features in FIG. 5B are the same as or similar to some of the features in FIGS. 1-5A as noted by same and/or similar reference characters, unless expressly described otherwise. Between neighboring miniaturized electrodes 412 within the column 516 there is no interstitial filler 414. This may allow for flexibility of the miniaturized impedance sensor 400 to bend about an axis perpendicular to the column 516. The lack of interstitial filler 414 may leave a channel 520a between two neighboring rows 518. In an embodiment, the miniaturized electrodes 412 may press against skin of a user to take bioimpedance measurements. The channel 520 may provide a path for channeling away sweat and/or debris that may otherwise interfere with the bioimpedance measurements.

FIG. 5C illustrates a head-on view of a second side of the miniaturized impedance sensor 400 illustrated in FIG. 5A, according to an embodiment. Some of the features in FIG. 5C are the same as or similar to some of the features in FIGS. 1-5B as noted by same and/or similar reference characters, unless expressly described otherwise. A section between neighboring miniaturized electrodes 412 along the row 518 may include the interstitial filler 414. The interstitial filler 414 may bond neighboring miniaturized electrodes 412 along the row 518, thereby strengthening the neighboring miniaturized electrodes 412. In an embodiment, the interstitial filler 414 may prevent and/or reduce a likelihood of breakage of the neighboring miniaturized electrodes 412 while the channel 520 may allow for flexibility of the miniaturized impedance sensor 400. In an embodiment, the miniaturized impedance sensor 400 may be integrated into a flexible athletic band that the user may wear during athletic and/or other strenuous activities. During such activities, the user may move quickly, frequently, and/or may engage in a wide range of movement. The movement of the user may put stress on the flexible athletic band that causes the flexible athletic band to flex quickly, frequently, and/or across a wide range. The channel 520 in the miniaturized impedance sensor 400 may allow the miniaturized impedance sensor 400 to flex with the flexible athletic band as the user moves, while the interstitial filler 414 may maintain rigidity of the miniaturized electrode 412 to prevent breakage as the user moves. The channel 520 may additionally allow a path in the miniaturized impedance sensor 400 for channeling away sweat and/or debris as the user moves.

Figure 6:
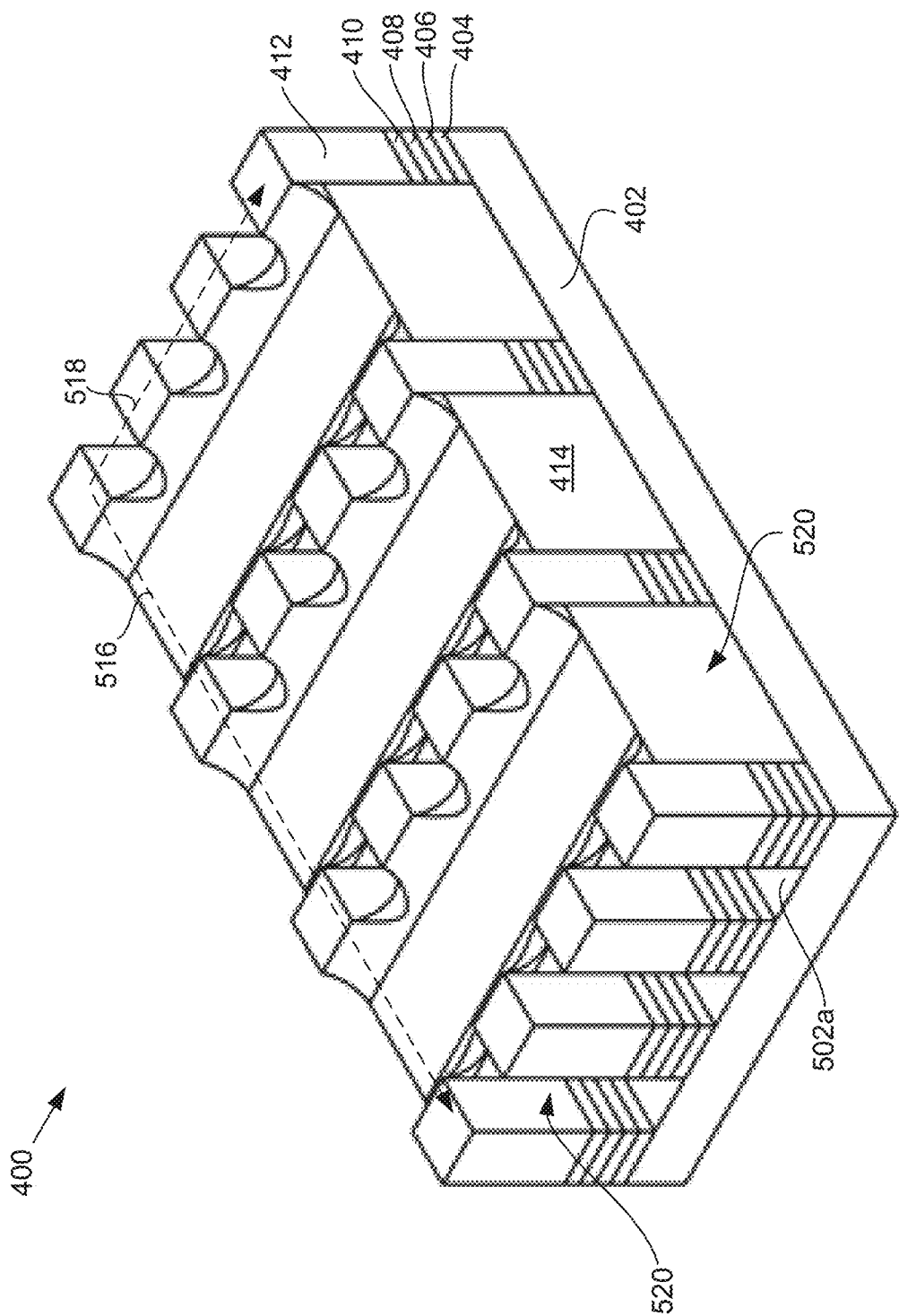
FIG. 6 illustrates a perspective view of the miniaturized impedance sensor with an interstitial filler disposed between rows of miniaturized electrodes, according to an embodiment.

FIG. 6 illustrates a perspective view of the miniaturized impedance sensor 400 with the interstitial filler 414 disposed between rows of miniaturized electrodes 412, according to an embodiment. Some of the features in FIG. 6 are the same as or similar to some of the features in FIGS. 1-5C as noted by same and/or similar reference characters, unless expressly described otherwise. The miniaturized impedance sensor 400 may include the growth substrate 402 and/or first insulating layer 404 on which various microstructures may be deposited, grown, and/or otherwise disposed. The microstructures may include the conductive layer 406, the second insulating layer 408, the catalyst layer 410, the miniaturized electrode 412, and/or the interstitial filler 414. The microstructures may be layered on the growth substrate 402. In one embodiment, the microstructures may be arranged in columns 616 and/or rows 618. The interstitial filler 414 may be disposed on the growth substrate 402 between neighboring rows 618. At least a portion of the growth surface 502a of the growth substrate 402 may remain exposed between neighboring miniaturized electrodes 412 along the same row 618. In an embodiment, the interstitial filler 414 may bolster the neighboring rows 618 of miniaturized electrodes 412.

Because air is a good insulator, various embodiments may include air as the interstitial filler 414. Because various polymers may have good structural strength, various embodiments may include one or more polymers as the interstitial filler 414. In a general embodiment, the miniaturized impedance sensor 400 may include a first region such as channel 520 between neighboring miniaturized electrodes 412 a second region 620 between neighboring miniaturized electrodes 412. In one embodiment, The channel 520 may be filled with a polymer such as polyimide and/or SU-8 to take advantage of the properties of such materials that may make the miniaturized impedance sensor 400 more durable and/or capable of resisting forces to break the miniaturized impedance sensor 400, and the second region 620 may be filled with air to take advantage of the insulating properties of air.

In one example, the miniaturized electrode 412 may have a rectangular cubic shape with a contact surface configured to form electrical contact with an object external to the miniaturized electrodes 412 or a wearable device that miniaturized electrodes 412 are integrated into. The rectangular cubic shape may include a first side and a second side longer than the first side. The contact surface may include the first side or the second side.

FIG. 7A illustrates a side view of the miniaturized impedance sensor 400 with circular miniaturized electrodes 412, according to an embodiment. Some of the features in FIG. 7A are the same as or similar to some of the features in FIGS. 1-6 as noted by same and/or similar reference characters, unless expressly described otherwise. Though shown separate from other elements of the miniaturized impedance sensor, the segment 700 may be incorporated with other miniaturized impedance sensor elements as described throughout this disclosure. The segment 700 may include the miniaturized electrode 412 and the interstitial filler 414. In an embodiment, the miniaturized electrode 412 may include a circular column of bundled and/or infiltrated nanotubes. The circular column may be cylindrical. The shape of the miniaturized electrode 412 may cause the wells 414a to be concave. For example, the interstitial filler 414 may be sprayed around the miniaturized electrodes 412 in a solution. The solution may be allowed to evaporate, which may reduce an overall volume of the interstitial filler 414. The interstitial filler 414 may adhere to the miniaturized electrodes 412 as the solution evaporates. This may cause portions of the interstitial filler 414 to slope down and/or away from the miniaturized electrodes 412. In an embodiment where the miniaturized electrodes 412 are cylindrical, the evaporation process may therefore cause the wells 414a to be concave.

Figure 7:
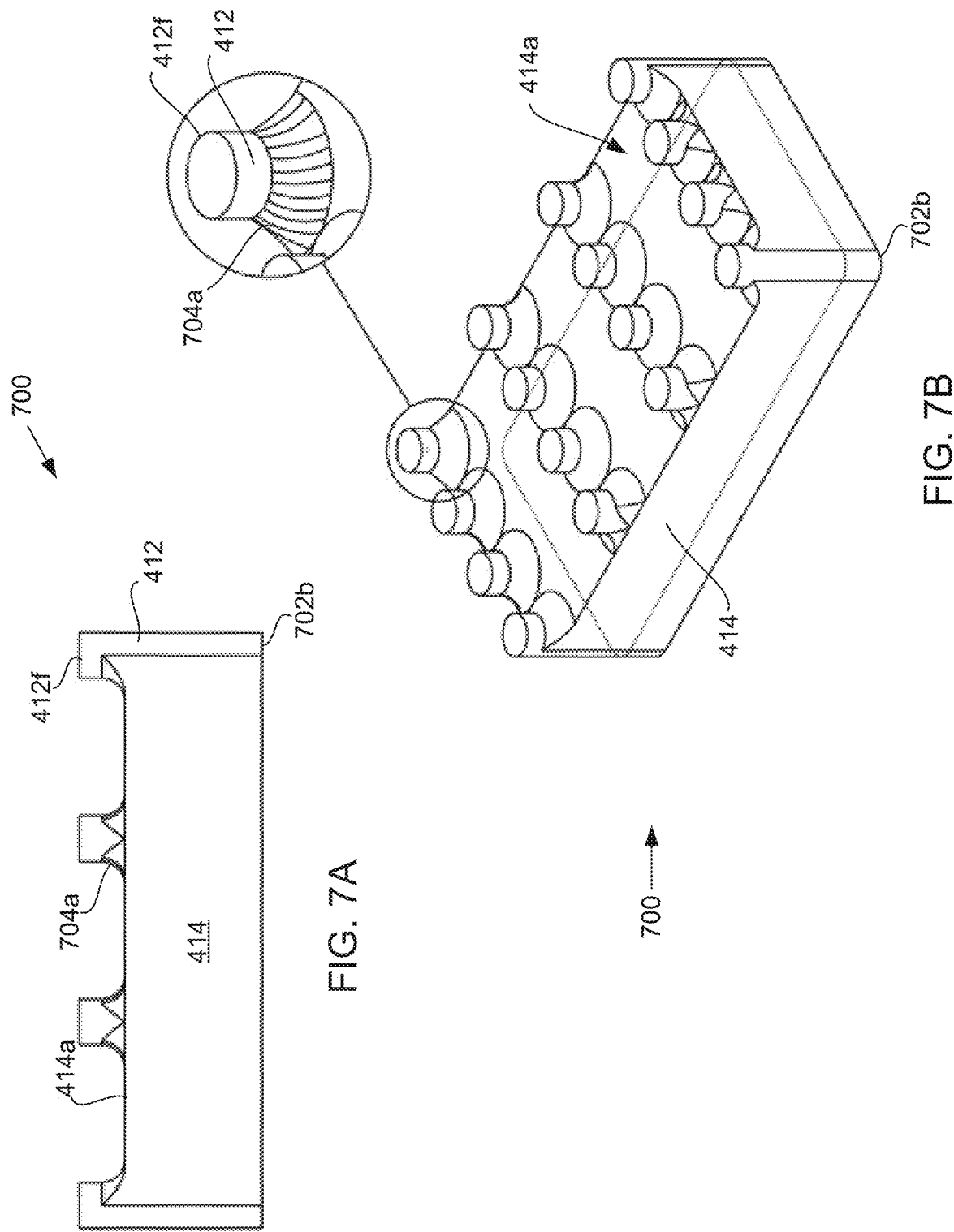
FIG. 7A illustrates a side view of the miniaturized impedance sensor with circular miniaturized electrodes, according to an embodiment.
FIG. 7B illustrates a perspective view of the miniaturized impedance sensor of FIG. 7A, according to an embodiment.

FIG. 7B illustrates a perspective view of the miniaturized impedance sensor of FIG. 7A, according to an embodiment. Some of the features in FIG. 7B are the same as or similar to some of the features in FIGS. 1-7A as noted by same and/or similar reference characters, unless expressly described otherwise. The miniaturized electrode 412 may have a top edge 702a and a bottom edge 702b. The interstitial filler 414 may be disposed against the miniaturized electrode 412 and/or surround at least a portion of the miniaturized electrode 412 between the bottom edge 702b and the top edge 702a. The interstitial filler 414 may be disposed around the miniaturized electrode 412 against and/or touching the bottom edge 702b while the top edge 702a of the miniaturized electrode 412 remains exposed from the interstitial filler 414. In an embodiment, this may increase contact with a user's skin while still providing the structural support of the interstitial filler 414. The interstitial filler 414 may include a sloped surface 704a that slopes up the miniaturized electrode 412 towards the top edge 702a and away from a main body of the interstitial filler 414. The sloped surface 704a may have a shape complimentary to a shape of the miniaturized electrode 412. In an embodiment, he sloped surface 704a may be circular.

Figure 8:
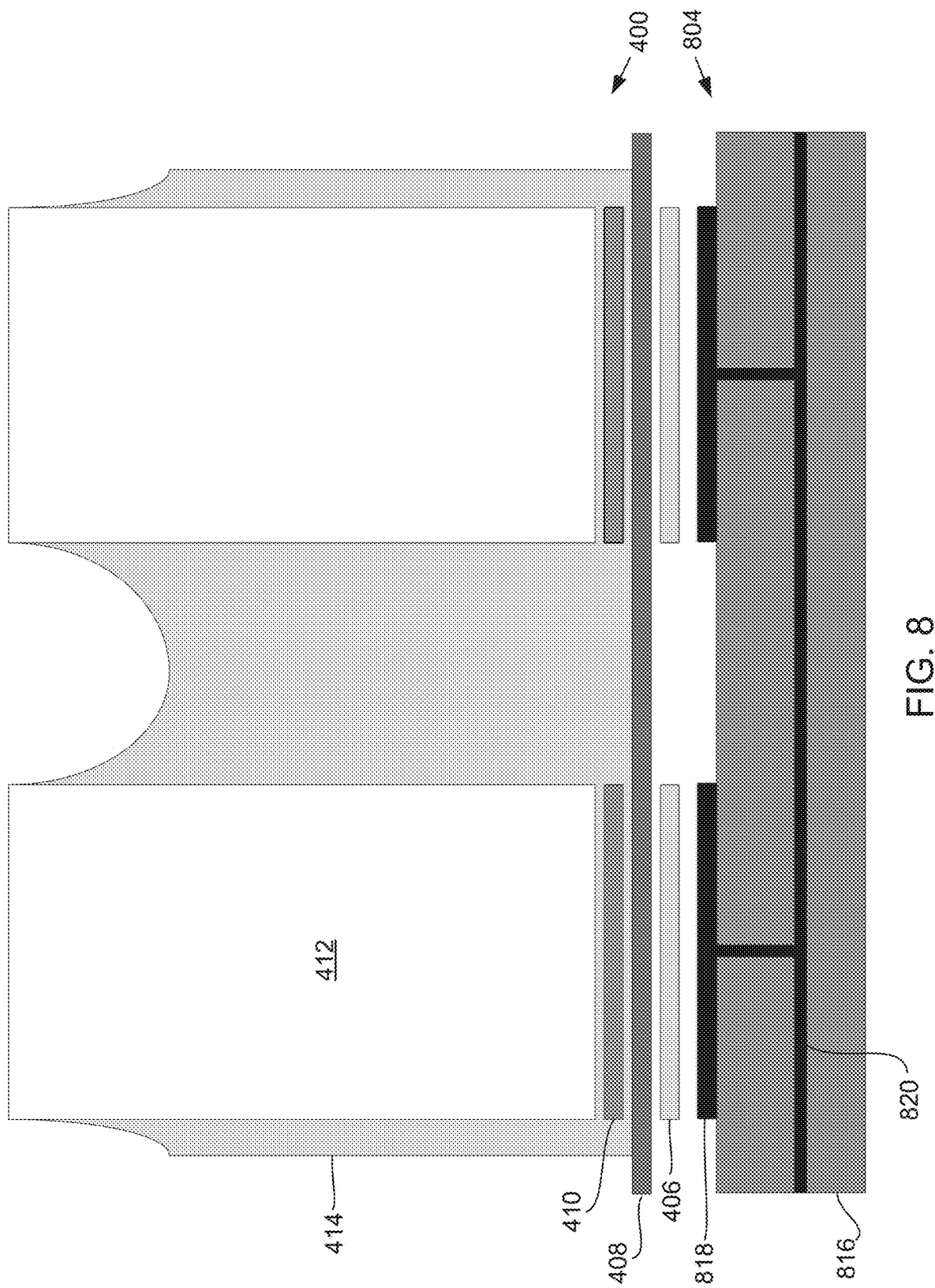
FIG. 8 illustrates a partially exploded schematic view of the miniaturized impedance sensor electrically coupled to a circuit board, according to an embodiment

FIG. 8 illustrates a partially exploded schematic view of the miniaturized impedance sensor 400 electrically coupled to a circuit board 804, according to an embodiment. Some of the features in FIG. 8 are the same as or similar to some of the features in FIGS. 1-7B as noted by same and/or similar reference characters, unless expressly described otherwise. The miniaturized impedance sensor 400 may include the conductive layer 406, the second insulating layer 408, the catalyst layer 410, the miniaturized electrode 412, or the interstitial filler 414. The circuit board 804 may include a substrate 816, a substrate conductor 818, or an electrical trace 820. The elements of the miniaturized impedance sensor 400 may have been manufactured on a growth substrate and base insulating layer, such as the growth substrate 402 and the first insulating layer 404. The growth substrate and/or base insulating layer may have been removed from the miniaturized impedance sensor 400 to expose the conductive layer 406 for direct contact with the substrate conductor 818.

The circuit board 804 may provide structural support and/or electronic interconnectivity of various electronic components integrated into an electronic device. In various embodiments, the electronic device may include a wearable device, such as the various embodiments of wearable devices described throughout this disclosure. In various embodiments, the electronic device may include a health monitoring device, such as the various embodiments of health monitoring devices described throughout this disclosure. The circuit board 804 may include a printed circuit board (PCB), a single-sided PCB, a double-sided PCB, a multi-layer PCB, a rigid PCB, a flex PCB, or a rigid-flex PCB, according to an embodiment. The circuit board 804 may be an integrated component of the wearable device. For example, the wearable device may include a band such as the band 106 illustrated in and described regarding FIGS. 1A-C. The band 106 may include the circuit board 804. The circuit board 804 may be disposed within the band 106. The circuit board 804 may be integrated into the band 106. The circuit board 804 may form one or more components of the band 106 such that the circuit board 804 is an integrated part of the band 106. For example, the band 106 may be formed of the substrate 816 and may have embedded in it the electrical trace 820. The circuit board 804 may include a rigid PCB, a flex PCB, and/or a rigid-flex PCB.

Although shown and labeled separately in FIG. 8, in an embodiment, various elements and/or layers of the miniaturized impedance sensor 400 may form structural components of the circuit board 804. In an embodiment, the miniaturized impedance sensor 400 may be integrated into a PCB. For example, the circuit board 804 may include a rigid-flex PCB. In an embodiment, the rigid-flex PCB may include layers of rigid materials integrated together with layers of flexible materials. The rigid materials may include the second insulating layer 408 and/or the flexible materials may include the substrate 816. According to an embodiment, the rigid-flex PCB may include a layer of alumina and/or a layer of polyimide, where the second insulating layer 408 includes the alumina and/or the substrate 816 includes the polyimide.

The substrate 816 of the circuit board 804 may be durable, flexible, rigid, compressible, and/or expandable. The substrate 816 may include alumina, aluminum nitride, beryllium oxide, polytetrafluoroethylene (PTFE), polyimide, or polyether ether ketone (PEEK). In an embodiment, the substrate 816 may include a ceramic-filled PTFE composite, a hydrocarbon ceramic laminate, or a glass-reinforced epoxy laminate. The substrate 816 may include layers of material to take advantage of different properties of different materials. In an embodiment, the electrical trace 820 may be disposed within the substrate 816, between two layers of the substrate 816, and/or on the substrate 816. In an embodiment, the substrate 816 may extend over and/or around the miniaturized impedance sensor 400 such that an upper section of the miniaturized electrode 412 may be exposed to a user wearing the wearable device while a remaining portion of the miniaturized impedance sensor may be disposed within the substrate 816.

The substrate conductor 818 may enable electrical conduction between the miniaturized impedance sensor 400 and the circuit board 804. The substrate conductor 818 may make contact with the conductive layer 406. In an embodiment, the substrate conductor 818 may include electrical solder, copper, tungsten, and/or nickel. The electrical trace 820 may be electrically coupled to the substrate conductor. In an embodiment, the substrate conductor 818 may include a through-hole through the substrate 816. The through-hole may include copper walls connected to a copper electrical trace 820. The conductive layer 406 may include leads that extend from the conductive layer 406. The leads may extend into the through-hole and form electrical contact with the copper. In another embodiment, the substrate conductor 818 may include patterned leads that match a pattern of the conductive layer 406. The conductive layer 406 may be set against the patterned leads of the substrate conductor 818. The electrical trace 820 may run through the substrate 816 and form electrical contact with the substrate conductor.

The electrical trace 820 may carry electrical power and/or signals between the miniaturized impedance sensor 400, the circuit board 804, and/or other electronic components electrically connected to the circuit board 804. The electrical trace 820 may be electrically coupled to the substrate conductor 818 and/or conductors corresponding to other electronic components of the wearable device. The electrical trace 820 may include a power trace, a ground trace, and/or a signal trace. In an embodiment, the electrical trace may include copper, silver, aluminum, gold, platinum, and so forth.

Figure 9:
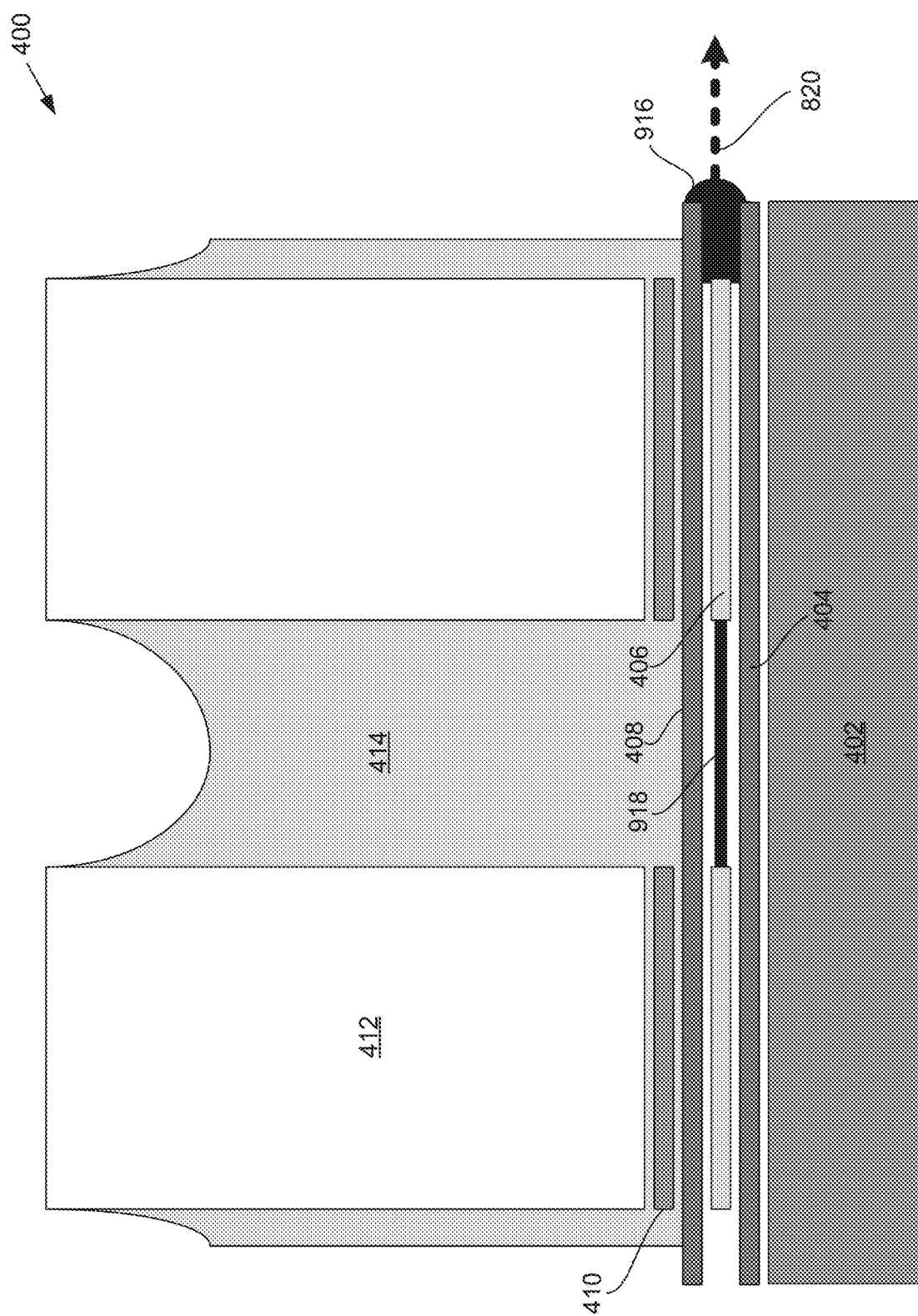
FIG. 9 illustrates a partially exploded schematic view of the miniaturized impedance sensor, according to an embodiment.

FIG. 9 illustrates a partially exploded schematic view of the miniaturized impedance sensor 400, according to an embodiment. Some of the features in FIG. 9 are the same as or similar to some of the features in FIGS. 1-8 as noted by same and/or similar reference characters, unless expressly described otherwise. The miniaturized impedance sensor 400 may include the growth substrate 402, the first insulating layer 404, the conductive layer 406, the second insulating layer 408, the catalyst layer 410, the miniaturized electrode 412, the interstitial filler 414, soldering 916, and/or an electrical interconnect 918. In an embodiment, the growth substrate 402 and/or first insulating layer 404 may be removed after manufacture of various microstructures of the miniaturized impedance sensor 400, which microstructures may include the conductive layer 406, the second insulating layer 408, the catalyst layer 410, the miniaturized electrode 412, or the interstitial filler 414. The microstructures may be integrated into a circuit board, which circuit board may be the same as or similar to other similarly named elements described and/or illustrated throughout this disclosure. The microstructures and/or circuit board may be integrated into a wearable device, according to an embodiment. In another embodiment, the growth substrate 402 and/or first insulating layer 404 may be retained with the microstructures and integrated with the microstructures into the wearable device. The wearable device may include the band. The growth substrate 402, the first insulating layer 404, and/or the microstructures may be integrated into the band. In such an embodiment, the growth substrate 402 may include a silicon interposer and/or a fused silica substrate. In one embodiment, the band may be flexible and the miniaturized impedance sensor 400 may be flexible with locally non-flexible regions. For example, the miniaturized impedance sensor 400 may include a first region with a non-flexible silicon substrate and a second region with a non-flexible silicon substrate. The first and second regions may be interconnected by a flexible substance such as polyimide. The first and second regions may further be electrically interconnected by conductive traces in the flexible substance. In another example, a flexible printed circuit board may be designed to be integrated into a band of a wrist-worn device. A shape or a size of the substrate 402 and/or a shape or a size of the locally non-flexible regions may be designed to flex with the flexible printed circuit board. In another example, the locally non-flexible regions may correspond to subsets of the miniaturized electrodes 412. In another example, the locally non-flexible regions may retain their shape as the flexible material changes shape.

In an embodiment, the band may include the electrical trace 820. The electrical trace 820 may electrically interconnect various electrical components integrated into the wearable device. The soldering 916 and/or the electrical interconnect 918 may electrically couple a microstructure of the miniaturized impedance sensor 400, such as the conductive layer 406, to the electrical trace 820 of the band. The miniaturized impedance sensor 400 may be electrically coupled to the other electrical components of the wearable device via the electrical trace 820 by the soldering 916 and/or the electrical interconnect 918. The electrical interconnect 918 may electrically couple neighboring positive regions of the conductive layer 406.

Figure 10:
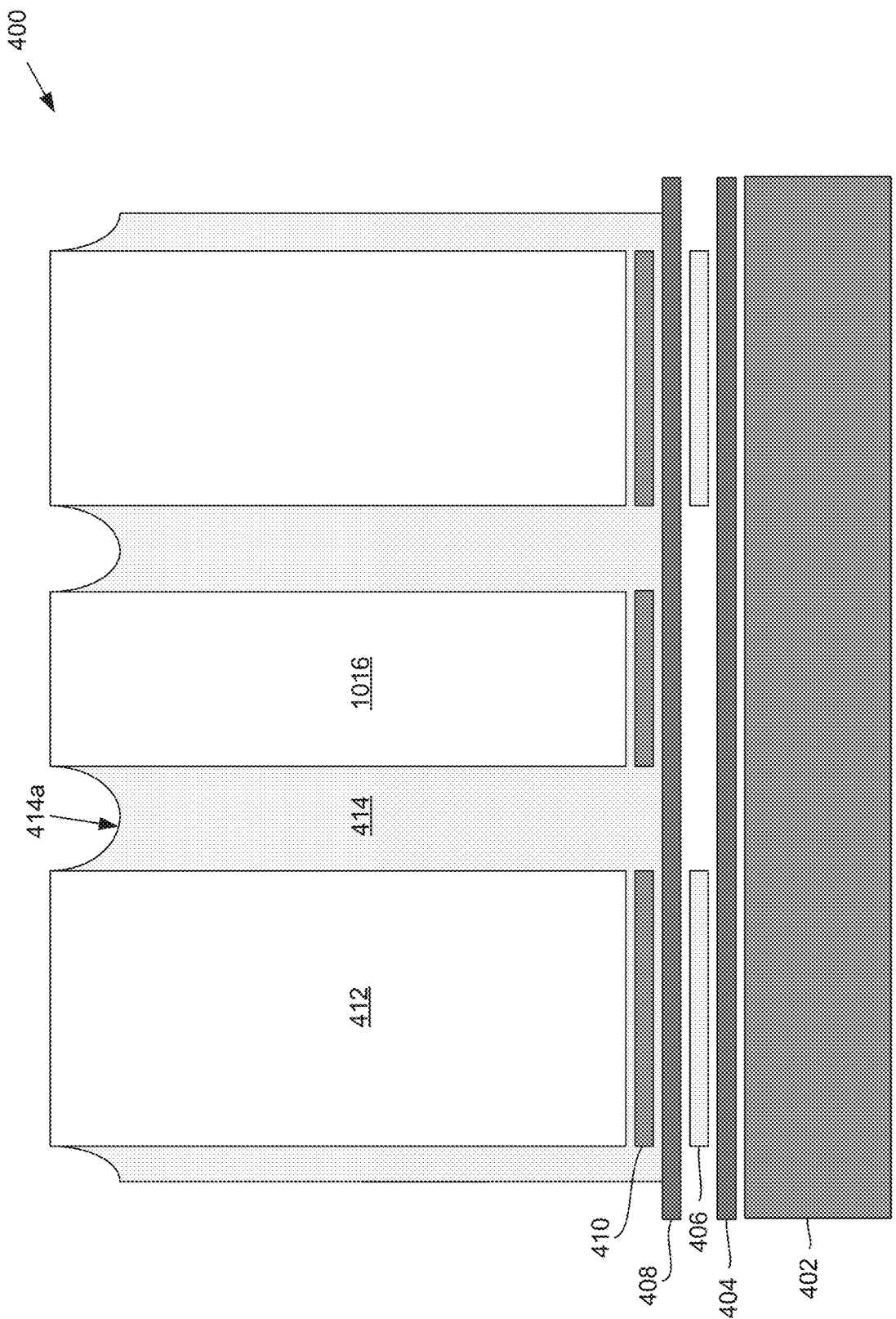
FIG. 10 illustrates a partially exploded schematic view of a miniaturized impedance sensor with an insulating column between neighboring miniaturized electrodes, according to an embodiment.

FIG. 10 illustrates a partially exploded schematic view of a miniaturized impedance sensor 400 with an insulating column 1016 between neighboring miniaturized electrodes 412, according to an embodiment. Some of the features in FIG. 10 are the same as or similar to some of the features in FIGS. 1-9 as noted by same and/or similar reference characters, unless expressly described otherwise. The miniaturized impedance sensor 400 may include the growth substrate 402, the first insulating layer 404, the conductive layer 406, the second insulating layer 408, the catalyst layer 410, the miniaturized electrode 412, the interstitial filler 414, and/or the insulating column 1016. The insulating column 1016 may be similar in structure and/or composition to the miniaturized electrode 412. For example, the insulating column 1016 may be grown on the catalyst layer 410 and/or may include bundles of carbon-infiltrated CNTs.

The insulating column 1016 may prevent bleeding of current between two miniaturized electrodes 412. In order to measure impedance of a material, current is passed between two electrodes through the material. Bleeding of current occurs when current bypasses the material and goes directly between the electrodes. This may negatively impact the impedance measurement. The insulating column 1016 may prevent bleeding of current by providing an alternative path for current that may bleed from the miniaturized electrodes 412. The insulating column 1016 may be electrically coupled to the catalyst layer 410. The catalyst layer 410 may be conductive, and/or may be electrically coupled to a ground. The insulating column 1016 may provide a path to ground for current that may bleed from the miniaturized electrodes 412. The insulating column 1016 may be electrically isolated from the conductive layer 406. The catalyst layer 410 may be patterned such that neighboring positive regions of the catalyst layer 410 may be electrically isolated from each other. Electrical isolation of the catalyst layer 410 positive regions may be accomplished by a spacing between neighboring positive regions and/or by coupling of a positive region coupled to the insulating column 1016 to the ground.

The insulating column 1016 may be grown and/or situated over a negative region of the conductive layer 406, such as the negative region described and/or illustrated regarding FIGS. 4A-C. The insulating column 1016 may increase the rigidity of the reinforced miniaturized impedance sensor 400 relative to a miniaturized impedance sensor embodiment without the insulating column 1016. The insulating column 1016 may decrease a depth of the well 414a relative to an embodiment without the insulating column 1016. The depth of the filler well 1014 may be measured from a top edge of the miniaturized electrode 412 to a point level with a lowest point of a top surface of the interstitial filler 414.

Figure 11A:
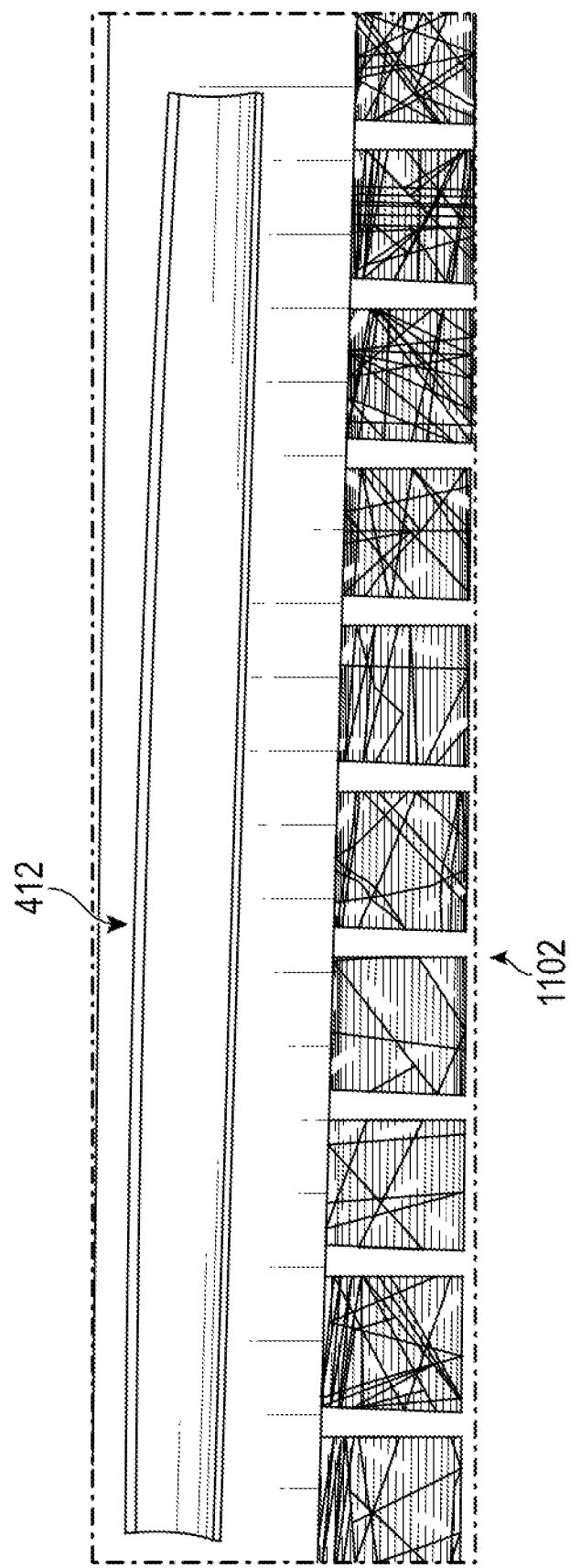
FIG. 11A is a picture of a miniaturized electrode for use in a miniaturized impedance sensor, according to an embodiment.

FIG. 11A is a picture of the miniaturized electrode 412 for use in a miniaturized impedance sensor, according to an embodiment. Some of the features in FIG. 11A are the same as or similar to some of the features in FIGS. 1-10 as noted by same and/or similar reference characters, unless expressly described otherwise. The miniaturized electrode 412 may be positioned next to a ruler 1102 with mm tick marks to demonstrate size of the miniaturized electrode. The miniaturized electrode 412 may have a width and/or height ranging from 0.1 mm to 2 mm. The miniaturized electrode may have a length of 10 mm. The miniaturized electrode 412 may have an average density ranging from 1 gram per cubic centimeter ($g/cm^3$) to 2 $g/cm^3$. In an embodiment, the miniaturized electrode 412 may have a width and/or height of 0.5 mm or 1.0 mm. In an embodiment, a set of miniaturized electrodes 412 of the miniaturized impedance sensor 400 may have an average density of 1.55+/−0.001 g/cm³, 1.50+/−0.05 g/cm³, or 1.25+/−0.02 g/cm³.

Figure 11B:
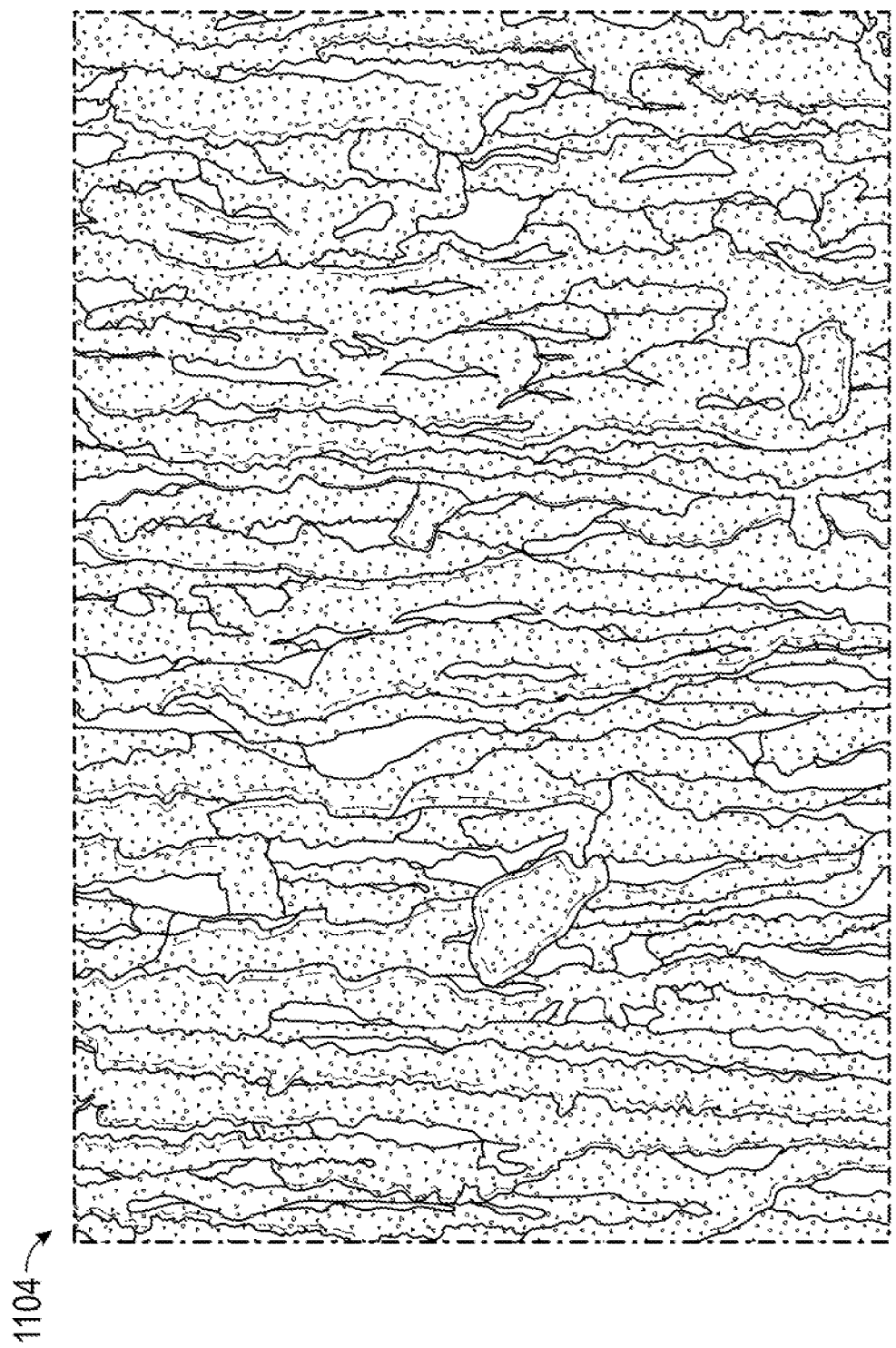
FIG. 11B is a picture of a nanotube forest within the miniaturized electrode of FIG. 11A, according to an embodiment.

FIG. 11B is a picture of a nanotube forest 1104 within the miniaturized electrode 412, according to an embodiment. Some of the features in FIG. 11B are the same as or similar to some of the features in FIGS. 1-11A as noted by same and/or similar reference characters, unless expressly described otherwise. The picture may show an approximately 12 micron by 9 micron area of nanotubes. The miniaturized electrode 412 may have been cut open to reveal the nanotube forest 1104. The nanotube forest 1104 may be infiltrated with carbon, as shown by the rough surface of the nanotubes. As described elsewhere herein, the nanotube forest 1104 may be aligned substantially parallel, with the nanotubes as grown aligned perpendicular to the growth substrate. For example, the nanotube forest 1104 may be part of an array of miniaturized electrodes that includes a carbon-infiltrated carbon nanotube forest. The carbon-infiltrated carbon nanotube forest comprises a bundle of aligned carbon nanotubes.

Figures 11C, 11D, 11E:
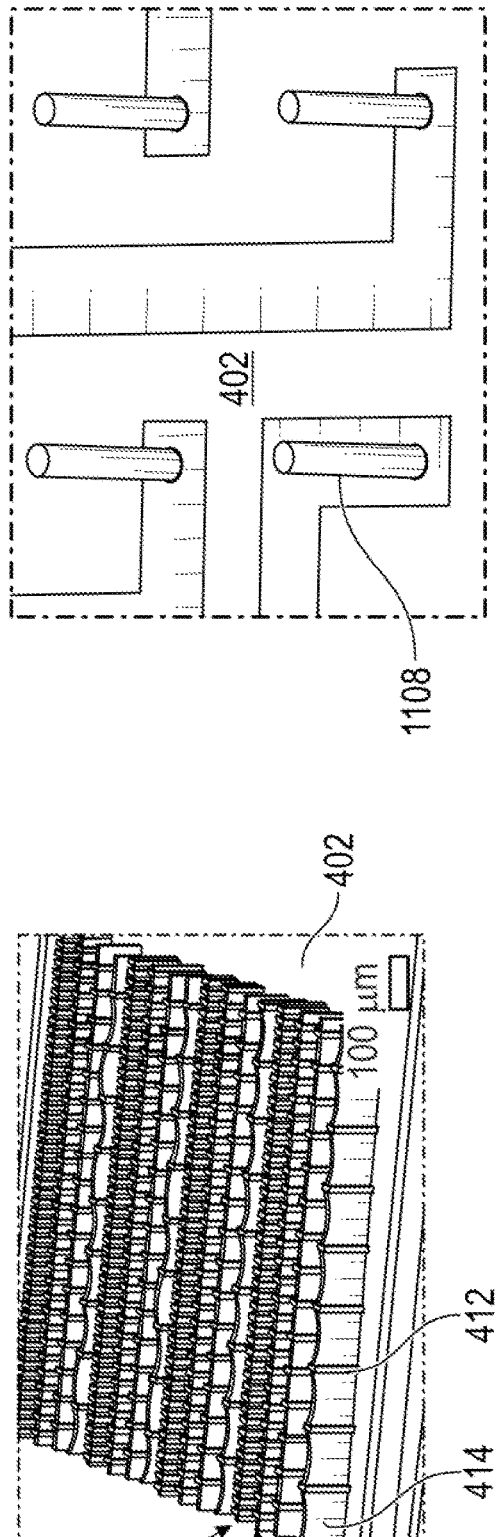
FIG. 11C is a picture of various configurations of rows of miniaturized electrodes, according to an embodiment.
FIG. 11D is a picture of miniaturized electrode pillars, according to an embodiment.
FIG. 11E is a picture of miniaturized electrode strips, according to an embodiment.

FIG. 11C is a picture of various configurations of rows 1106a-d of miniaturized electrodes 412, according to an embodiment. Some of the features in FIG. 11C are the same as or similar to some of the features in FIGS. 1-11B as noted by same and/or similar reference characters, unless expressly described otherwise. The rows 1106a-d of miniaturized electrodes 412 may be grown and/or patterned on the growth substrate 402. The rows 1106a-d may include a plurality of the miniaturized electrode 412 with the interstitial filler 414 disposed between the miniaturized electrode 412. A first row 1106a may have an inter-electrode spacing ranging from 50 microns to 150 microns. A second row 1106b may have an inter-electrode spacing ranging from 30 microns to 70 microns. A third row 1106c may have an inter-electrode spacing ranging from 5 microns to 30 microns. A fourth row 1106d may have an inter-electrode spacing ranging from less than 1 micron to 10 microns. The miniaturized electrodes 412 may have a height ranging from 50 microns to 150 microns. The miniaturized electrodes 412 may have a width ranging from 10 microns to 30 microns. In an embodiment, the first row 1106a may have a center-to-center inter-electrode spacing of 100 microns; the second row 1106b may have a center-to-center inter-electrode spacing of 60 microns; the third row 1106c may have a center-to-center inter-electrode spacing of 15 microns; the fourth row 1106d may have a center-to-center inter-electrode spacing of 5 microns; and the miniaturized electrodes 412 in the rows 1106a-d may have a height of 100 microns and a width of 15 microns.

FIG. 11D is a picture of miniaturized electrode pillars 1108, according to an embodiment. Some of the features in FIG. 11D are the same as or similar to some of the features in FIGS. 1-11C as noted by same and/or similar reference characters, unless expressly described otherwise. The miniaturized electrode pillars 1108 may be grown on the growth substrate 402. In general, the miniaturized electrode pillars 1108 may be characterized by having a height extending from the growth substrate 402 that may be greater than a width and/or diameter of the miniaturized electrode pillar 1108. The miniaturized electrode pillars 1108 may be circular. The miniaturized electrode pillars 1108 may have a height ranging from 100 microns to 500 microns. The miniaturized electrode pillars 1108 may have a width ranging from 20 microns to 60 microns. In an embodiment, the miniaturized electrode pillars 1108 may have a width of approximately 40 microns and a height of approximately 200 microns.

FIG. 11E is a picture of miniaturized electrode strips 1110, according to an embodiment. Some of the features in FIG. 11E are the same as or similar to some of the features in FIGS. 1-11D as noted by same and/or similar reference characters, unless expressly described otherwise. The miniaturized electrode strips 1110 may be grown on the growth substrate 402. In general, the miniaturized electrode strips 1110 may have a length parallel to the growth substrate 402 that may be greater than a width of the miniaturized electrode strips 1110. In one embodiment, the miniaturized electrode strips 1110 may be formed straight with the miniaturized electrode strips 1110 aligned parallel to each other. In another embodiment, the miniaturized electrode strips 1110 may for formed into a pattern such as a zig-zag pattern with the patterns of the miniaturized electrode strips 1110 aligned with each other. The miniaturized electrode strips 1110 may be formed of the nanotube forest 1104.

FIG. 12A illustrates a schematic view of a section of the wearable device 100 with an integrated sensor, according to an embodiment. Some of the features in FIG. 12A are the same as or similar to some of the features in FIGS. 1-11E as noted by same and/or similar reference characters, unless expressly described otherwise. The wearable device 100 may include the miniaturized impedance sensor 400, the band 106, electronic components 1206, and/or an electrical trace 820. The electronic components 1206 may include elements the same as or similar to those illustrated in and described regarding FIGS. 1A-C, FIG. 24, and/or FIG. 26. In an embodiment, the miniaturized impedance sensor 400 may be integrated into the band 106.

FIG. 12B illustrates a zoomed in view of the sensor illustrated in FIG. 12A, according to an embodiment. Some of the features in FIG. 12B are the same as or similar to some of the features in FIGS. 1-12A as noted by same and/or similar reference characters, unless expressly described otherwise. The miniaturized impedance sensor 400 may include a substrate 1210, the miniaturized electrode 412, the soldering 916, and the electrical interconnect 918. The substrate 1210 may include a base substrate layer such as the growth substrate 402 and/or a flexible substrate, a conductive layer corresponding to the miniaturized electrode 412, and/or an interstitial filler between neighboring miniaturized electrodes 412. The electrical interconnect 918 may be embedded in the substrate 1210. The electrical interconnect 918 may electrically couple the miniaturized electrode 412 and/or the corresponding conductive layer to the soldering 916. The soldering 916 may be electrically coupled to the electrical trace 820. The electrical trace 820 may electrically couple the miniaturized impedance sensor 400 to a processing device, a power source, or a memory device incorporated with the electronic components 1206. The power source may supply power to the miniaturized impedance sensor 400 so that the miniaturized impedance sensor 400 may take a bioimpedance measurement from a user wearing the wearable device. The bioimpedance measurement may be received by the processing device. The processing device may utilize the bioimpedance measurement to determine a physiological condition of the user. The memory device may store the bioimpedance measurement or the physiological condition. The electronic components 1206 may interact with the miniaturized impedance sensor 400 in a variety of ways, some of which may be described in more detail regarding other FIGs. in this disclosure, such as FIG. 26.

Neighboring miniaturized electrodes 412 may be arranged in rows which may include a first row 1212a and a second row 1212b. The neighboring miniaturized electrodes 412 in the same row 1212a or 1212b may be interconnected by the electrical interconnect 918, which may electrically couple the row 1212a or 1212b to the electrical trace 820. In an embodiment, one electrical trace 820 may correspond to one row 1212a or 1212b. In an embodiment, one electrical trace 820 may correspond to multiple rows 1212a and 1212b. In one embodiment, the first row 1212a may be a positive electrode of a circuit, and the second row 1212b may be a negative electrode of the circuit. The first row 1212a may be electrically coupled to a separate electrical trace 820 from the second row 1212b. In another embodiment, the first and second rows 1212a and 1212b may both be negative electrodes, and another row may be the positive electrode. The electrical traces 820 connected to each of the first and second rows 1212a and 1212b may be combined into a single electrical trace 820 before connecting to the electronic components. The first and second rows 1212a and 1212b may otherwise be electrically coupled to each other between the miniaturized impedance sensor 400 and the electronic components 1206.

The wearable device 100 may be configured in one or more of a variety of ways to enable measurement of one or more of a variety of physiological conditions, physiological parameters, and/or physiological constituents. In an embodiment, one or more rows 1212a and/or 1212b of miniaturized electrodes 412 may be fixed as a positive electrode or a negative electrode. In an embodiment, one or more rows of miniaturized electrodes 412 may be switchable between acting as a positive electrode and acting as a negative electrode. In an embodiment where rows of miniaturized electrodes 412 are switchable, the electrical trace 820 corresponding to a switchable row of miniaturized electrodes 412 may include and/or be electrically coupled to logic and/or hardware to switch the switchable row between on, off, positive, and/or negative configurations. In an embodiment, a single row of miniaturized electrodes 412 may be the positive electrode and the remaining rows of miniaturized electrodes 412 of the miniaturized impedance sensor 400 may be the negative electrode. In another embodiment, a single row of miniaturized electrodes 412 may be the negative electrode and the remaining rows of miniaturized electrodes 412 of the miniaturized impedance sensor 400 may be the positive electrode. One or more of the remaining rows of miniaturized electrodes 412 may be switchable between on and/or off configurations. The single row of miniaturized electrodes 412 may be switchable between on and/or off configurations.

In various embodiments, a first set of rows of miniaturized electrodes 412 may be the positive electrode and a second set of rows of miniaturized electrodes 412 may be the negative electrode. In one such embodiment, the first set of rows of miniaturized electrodes 412 may be disposed on a first end of the miniaturized impedance sensor 400, and the second set of rows of miniaturized electrodes 412 may be disposed on a second end of the miniaturized impedance sensor 400. In another such embodiment, the first and second sets of rows of miniaturized electrodes 412 may be interspersed such that sequential rows alternate between positive electrode rows and negative electrode rows.

A configuration of the electrical trace 820 may enable switching of the rows of miniaturized electrodes 412 between various arrangements of positive electrode rows and negative electrode rows. The configuration may include hardware and/or software logic that may switch the electrical trace 820 from a positive end of a circuit to a negative end of the circuit. The configuration may include one or more electrical connections between separate electrical traces 1208 connecting separate rows of miniaturized electrodes 412. A processing device and/or memory device electrically coupled by the electrical trace 820 to the rows of miniaturized electrodes 412 may store machine-readable instructions which, when executed by the processing device, may configure the rows of miniaturized electrodes 412 to a particular electrode configuration (i.e. the positive and negative electrode configurations described throughout this disclosure) by the switching logic via the electrical trace 1208.

Figure 13A:
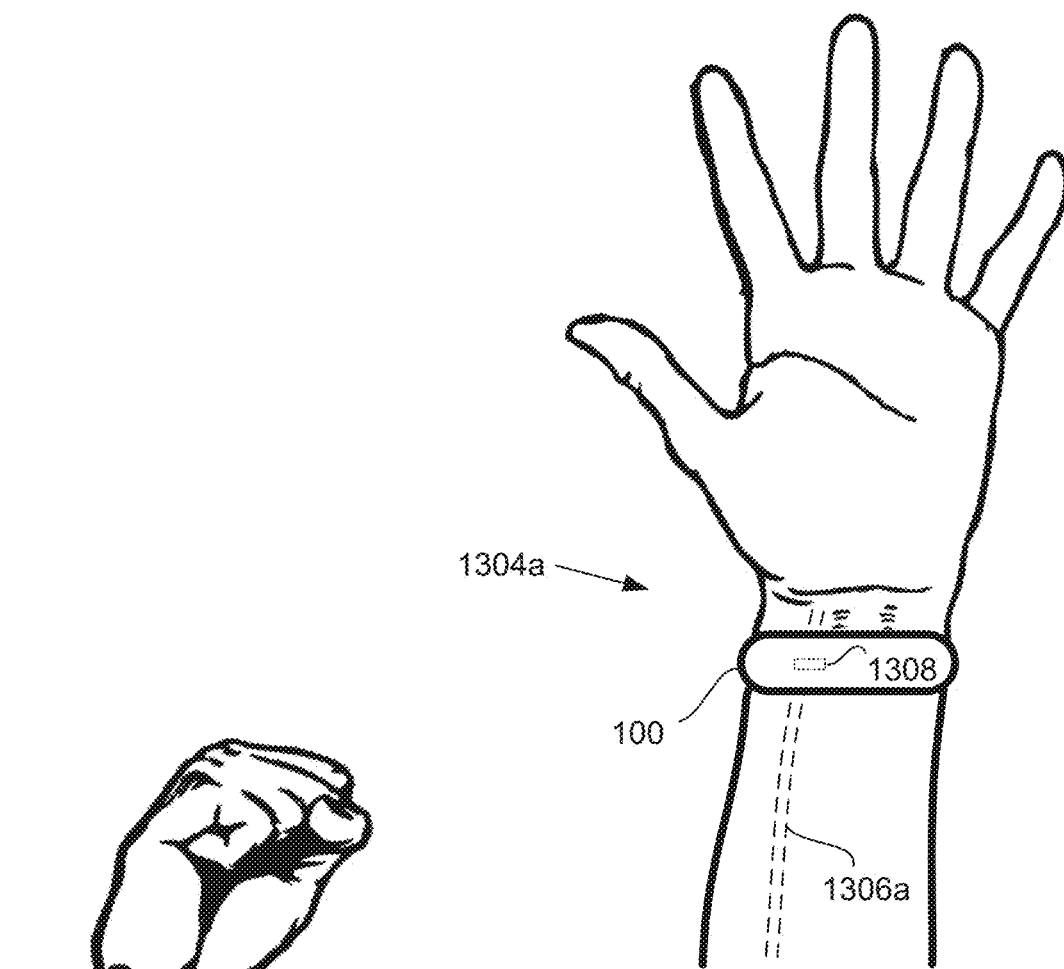
FIG. 13A illustrates the wearable device on a wrist of a user, according to an embodiment.

FIG. 13A illustrates the wearable device 100 on a wrist 1304a of a user, according to an embodiment. Some of the features in FIG. 13A are the same as or similar to some of the features in FIGS. 1-12B as noted by same and/or similar reference characters, unless expressly described otherwise. The wrist 1304a may include a first muscular-walled tube 1306a. The first muscular-walled tube 1306a may be, in an embodiment, a vein or an artery. The wearable device 100 may have an integrated biometric sensor 1308. The biometric sensor 1308 may include a miniaturized impedance sensor.

The wearable device 100 may be positioned on the wrist 1304a so that the biometric sensor 1308 may be positioned over the muscular-walled tube 1306a. In an embodiment, the first muscular-walled tube 1306a may be positioned in the wrist 1304a approximate to an underside of the wrist 1304a. For example, the first muscular-walled tube 1306a may be positioned in the wrist 1304a between a dermal layer of the wrist 1304a and one or more bones in the wrist 1304a. The biometric sensor 1308 may be positioned against the underside of the wrist 1304a. This may optimize an accuracy and/or precision of a measurement taken by the biometric sensor 1308 from the muscular-walled tube 1306a. The wearable device 100 may use the measurements to determine a physiological condition of the user. Positioning the biometric sensor 1308 against the underside of the wrist may also reduce a chance of the biometric sensor 1308 being struck or otherwise damaged in a way that may affect the accuracy and/or precision of the measurement taken by the biometric sensor 1308. For example, an outside of the wrist 1304a may be exposed to other surfaces against which the wearable may be struck, whereas in underside of the wrist 1304a may be less likely to strike other surfaces because it faces towards a body of the user.

Figure 13B:
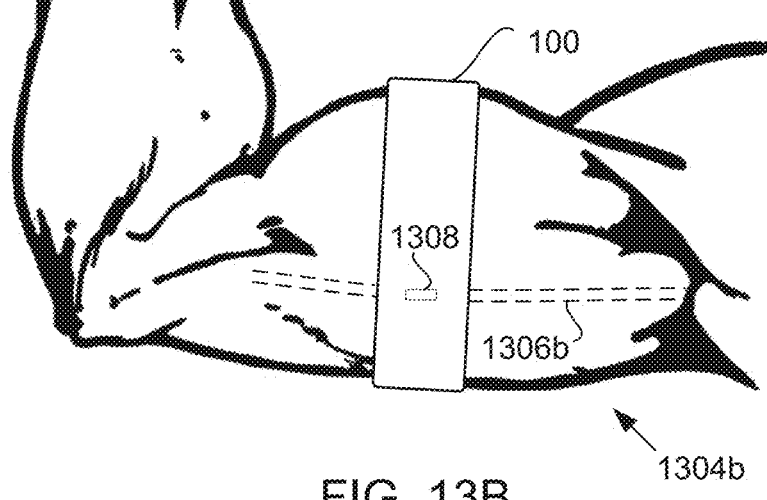
FIG. 13B illustrates the wearable device on an arm of a user, according to an embodiment.

FIG. 13B illustrates the wearable device 100 on an arm 1304b of the user, according to an embodiment. Some of the features in FIG. 13B are the same as or similar to some of the features in FIGS. 1-13A as noted by same and/or similar reference characters, unless expressly described otherwise. The arm 1304b may include a second muscular-walled tube 1306b. The second muscular-walled tube 1306b may be, in an embodiment, a vein or an artery. The wearable device 100 may be positioned on the arm 1304b so that the biometric sensor 1308 may be positioned over the second muscular-walled tube 1306b.

In various embodiments, the wearable device 100 may be worn by the user on another body part such as a hand of the user, a forearm of the user, an elbow of the user, a chest of the user, a neck of the user, a head of the user, a torso of the user, a waist of the user, a thigh of the user, a calf of the user, a knee of the user, an ankle of the user, or a foot of the user. Accordingly, the body part may include a muscular-walled tube. The he muscular-walled tube may include an ulnar artery, a radial artery, a brachial artery, a basilic vein, a cephalic vein, an axillary artery, an axillary vein, a carotid artery, a jugular vein, an iliac artery, a femoral artery, a femoral vein, a tibial artery, a great saphenous vein, a dorsalis pedis artery, an arch of foot artery, or a temporal artery.

In various embodiments, the biometric sensor 1308 may be pressed against a skin surface of the body part. The biometric sensor 1308 and/or wearable device 100 may be positioned on the body part over a region of the body part where the muscular-walled tube may be closest to the skin surface for the body part. The biometric sensor 1308 may be positioned against the body part where the muscular-walled tube may be positioned between the biometric sensor 1308 and a skeletal structure of the body part. This may minimize a distance between the biometric sensor 1308 and the muscular-walled tube, which in turn may optimize one or more biometric measurements taken by the biometric sensor 1308 from the muscular-walled tube. In various embodiments, the biometric sensor 1308 and/or the wearable device 100 may be positioned on the body part over a region of the body part where the skeletal structure is positioned between the skin surface and the muscular-walled tube. This may maximize the distance between the biometric sensor 1308 and the muscular-walled tube, which in turn may minimize effects of the muscular-walled tube on measurements taken by the biometric sensor 1308. For example, the user may desire to take a measurement of a relatively static physiological condition, physiological parameter, and/or physiological constituent such as a bone density of the user and/or a body fat percentage of the user. The muscular-walled tube may be dynamic and may interfere with measuring the static physiological condition, physiological parameter, and/or physiological constituent. Accordingly, maximizing the distance between the biometric sensor 1308 and the muscular-walled tube may result in more accurate and/or precise measurements of the static physiological condition, physiological parameter, and/or physiological constituent. In various embodiments, the biometric sensor 1308 and/or the wearable device 100 may be positioned on the body part such that the biometric sensor 1308 may be approximate the muscular-walled tube and the skeletal structure such that the muscular-walled tube is not between the skeletal structure and the biometric sensor 1308 and the skeletal structure is not between the muscular-walled tube and the biometric sensor 1308.

FIG. 14A illustrates impedance paths 1410 for the miniaturized impedance sensor 400 from a side view of the miniaturized impedance sensor 400, according to an embodiment. Some of the features in FIG. 14A are the same as or similar to some of the features in FIGS. 1-13B as noted by same and/or similar reference characters, unless expressly described otherwise. The miniaturized impedance sensor 400 may include a first substrate 1402, a second substrate 1404, the miniaturized electrode 412, and/or the interstitial filler 414, which elements may be the same as or similar to other similarly named elements described and/or illustrated throughout this disclosure. The first substrate may include a circuit board and/or electrical trace, which elements may be similar to or the same as other similarly named elements described and/or illustrated throughout this disclosure. The second substrate 1404 may be layered. The second substrate 1404 may include a first insulating layer such as the first insulating layer 404, a conductive layer such as the conductive layer 406, a second insulating layer such as the second insulating layer 408, and/or a catalyst layer such as the catalyst layer 410.

Neighboring miniaturized electrodes 412 may be electrically interconnected, such as is illustrated in and described regarding FIGS. 12A-B. In an embodiment, within the miniaturized impedance sensor 400, the miniaturized electrodes 412 may be electrically interconnected along a Y-axis, and/or may be electrically insulated from each other along an X-axis. In another embodiment, the miniaturized electrodes 412 may be electrically interconnected along the X-axis, and/or may be electrically insulated from each other along the Y-axis. The top sides of the miniaturized electrodes 412 may be positioned against a surface. In an embodiment, the surface may include a skin surface of a user wearing a wearable device into which the miniaturized impedance sensor 400 may be incorporated. A current may be applied between a first row 1412 of miniaturized electrodes 412 and a second row 1414 of miniaturized electrodes 412. In an embodiment, the first row 1412 of miniaturized electrodes 412 may be a positive electrode, and/or the second row 1414 of miniaturized electrodes 412 may be a negative electrode. The current may follow a path through the surface and/or a subsurface layer.

A measurement of impedance of a surface and/or subsurface layer or element may indicate a state of the surface and/or subsurface layer or element. Impedance may be measured by passing current between the positive electrode and the negative electrode, where the surface and/or subsurface layer or element may impede at least a portion of the current. The impedance paths 1410 may illustrate the current paths between the positive electrode and the negative electrode. The positive electrode and the negative electrode may be electrically coupled to a common power source which may supply the current. Impedance may be indicated by a voltage or a change in current. In an embodiment, the voltage may be measured between the positive electrode and the negative electrode. The voltage may be used by a processing device to determine an impedance of the surface and/or the subsurface layer. In another embodiment, the change in current may be measured between the positive electrode and the negative electrode. The change in current may be used by the processing device to determine the impedance of the surface and/or subsurface layer. In an embodiment, the subsurface layer may be a subcutaneous region of the user. Accordingly, the impedance may represent a bioimpedance measurement of the user, in an embodiment.

Figure 15A:
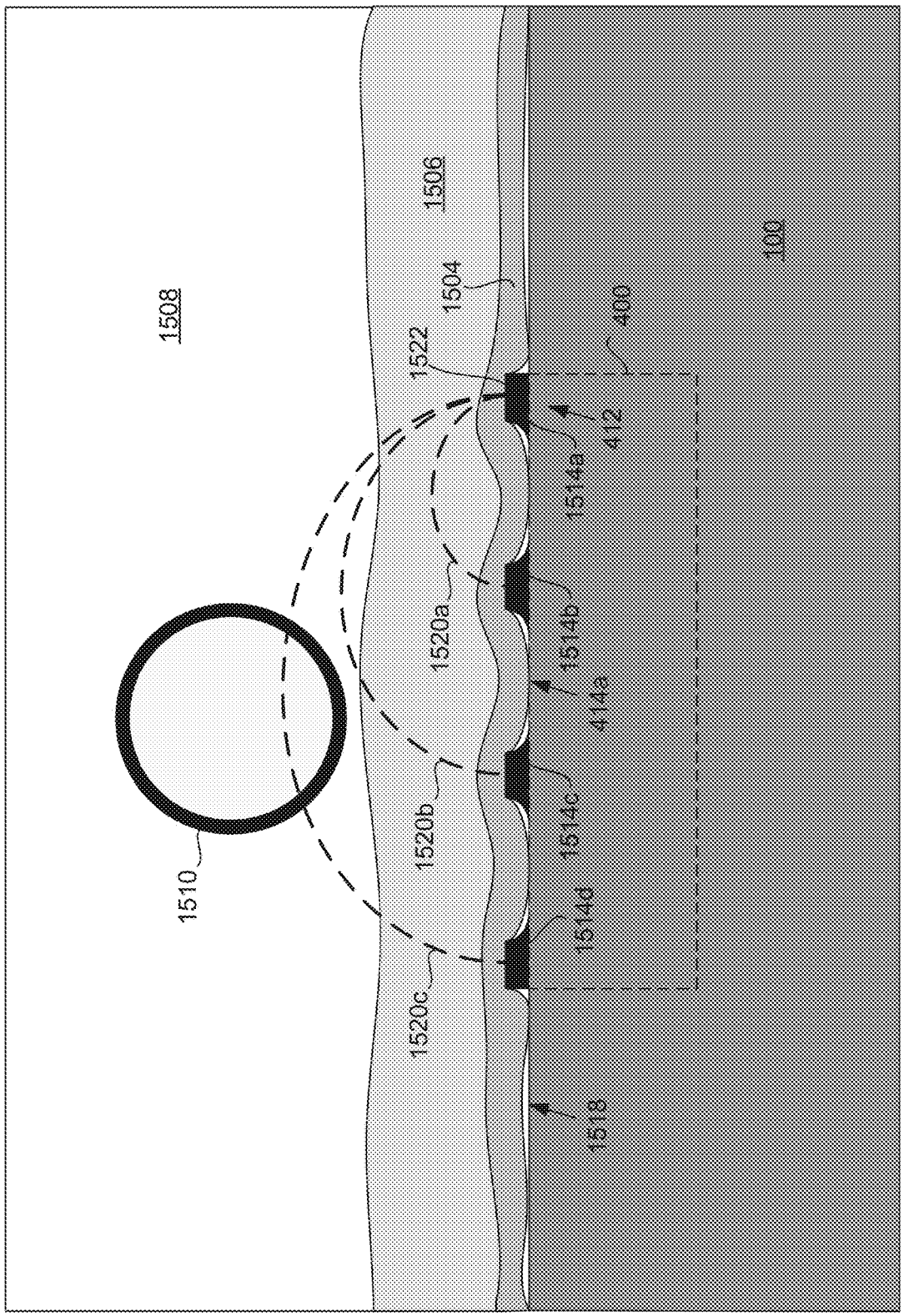
FIG. 15A illustrates impedance paths through various subcutaneous layers of a user of a wearable device, where the wearable device is aligned perpendicular to a muscular-walled tube, according to an embodiment.
Figure 15B:
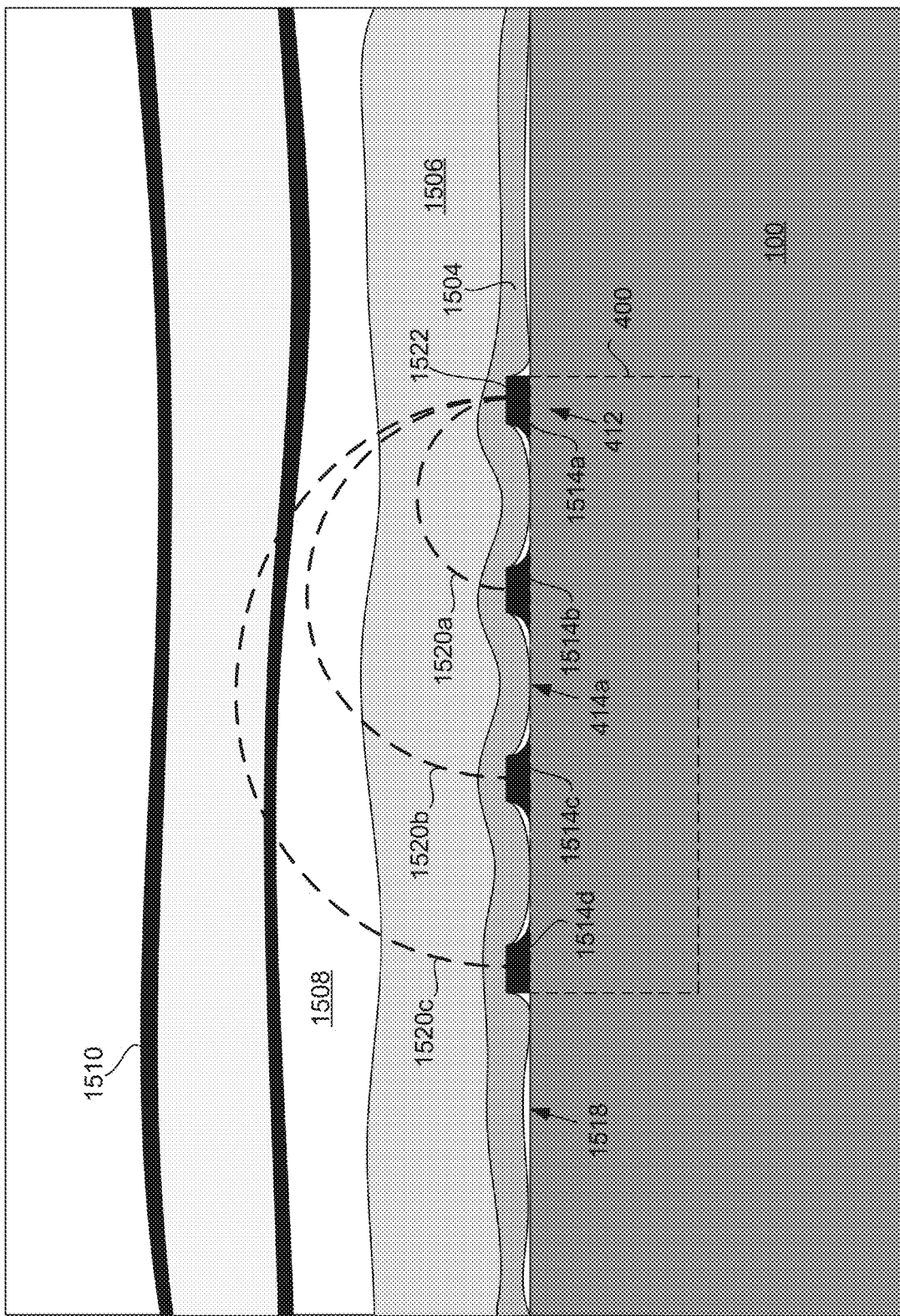
FIG. 15B illustrates the impedance paths through the subcutaneous layers illustrated in FIG. 15A, where the wearable device is aligned parallel to the muscular-walled tube, according to an embodiment.

FIG. 15A illustrates impedance paths of the miniaturized impedance sensor 400 aligned perpendicular to a muscular-walled tube 1510. FIG. 15B illustrates impedance paths of the miniaturized impedance sensor 400 aligned parallel to the muscular-walled tube 1510. Some of the features in FIGS. 15A-B are the same as or similar to some of the features in FIGS. 1-14B as noted by same and/or similar reference characters, unless expressly described otherwise. The dermal layers of the user may include an epidermis 1504, a dermis 1506, a hypodermis 1508, and/or an internal element or subsurface element such as the muscular-walled tube 1510, which elements may be the same as or similar to other similarly named elements described and/or illustrated throughout this disclosure. The wearable device 100 may be the same as or similar to other wearable devices and/or wearable devices described and/or illustrated throughout this disclosure. The wearable device 100 may have an embedded miniaturized impedance sensor 400. The wearable device 100 may include the band 106, where the band is configured or shaped to press an array of miniaturized electrodes of the miniaturized impedance sensor 400 into the epidermis 1504 or skin of a body part of a user with an optimal pressure. The optimal pressure may maximizes contact of the array of miniaturized electrodes with the epidermis 1504 or skin and minimizes shunting of capillary sphincters.

The miniaturized impedance sensor 400 may features described and/or illustrated regarding other FIGs. throughout this disclosure. The miniaturized impedance sensor 400 may include the miniaturized electrode 412 and/or the interstitial wells 414*a*. In one example, the miniaturized electrode 412 may form and electrical contact with a body part, such as the epidermis 1504, and transmit electrical current through the body part to be received at another miniaturized electrode.

Conventional bioimpedance sensors may include pads. The pads may have a wide area, such as an area measured in square millimeters and/or square centimeters. The pads may additionally be formed of a relatively rough and/or porous material when compared with human skin, especially skin along areas of body parts with veins and/or arteries close to the surface of the skin. The features of the pads relative to the skin may result in poor initial conductive contact between the pads and the skin. In such configurations, the present inventors have discovered that there may be an "acclimation period" at the end of which time the pad maximizes conductive contact with the skin of a user. The acclimation period may last approximately 30 minutes. During the acclimation period, measurements taken using the bioimpedance sensor may be unreliable. Other factors may cause the measurements to be unreliable. For example, sweat and/or debris may accumulate between the pads and the skin which may result in poor conductive contact between the pads and the skin. Such accumulation may lead to further unreliability of measurements. Various embodiments throughout this disclosure may address the unreliability of bioimpedance sensors having relatively large, rough, and/or porous pads, in addition to improving upon other previous solutions in various ways.

The wearable device 100 may be pressed against the epidermis 1504. In one embodiment, the miniaturized electrode 412 may protrude from a surface 1518 of the wearable device 100. The interstitial well 414*a* may be flush with the wearable device surface 1518 to form a continuous surface with the wearable device surface 1518. The top portion of the miniaturized electrode 412 may press into the epidermis 1504. The top portion of the miniaturized electrode 412 may deform the regions of the epidermis 1504 immediately surrounding the top portion of the miniaturized electrode 412 with little or no deformation of other regions of the epidermis 1504 such as those regions against the wearable device surface 1518. The top portion of the miniaturized electrode 412 may form smooth and/or complete contact with the epidermis 1504. The epidermis 1504 may flex and/or form into the interstitial well 414*a*. The interstitial well 414*a* may provide a channel for collecting and/or channeling away sweat and debris from the miniaturized electrode 412 and/or epidermis 1504. This may further improve contact between the top portion of the miniaturized electrode 412 and the epidermis 1504 by providing an outlet for debris and/or sweat that may otherwise accumulate between the epidermis 1504 and the miniaturized electrode 412. The miniaturized electrode 412 may be formed of a smooth and/or non-porous material that may additionally improve contact between the miniaturized electrode 412 and the epidermis 1504. For example, in one embodiment the miniaturized electrode 412 may be formed of CNTs coated with polyimide.

In one embodiment, a top surface 1522 of the miniaturized electrode 412 may be flush with the wearable device surface 1518 to form a continuous surface with the wearable device surface 1518. The miniaturized electrode 412 may be formed of the smooth and/or non-porous material such that the miniaturized electrode 412 may form continuous contact with the epidermis 1504. The top surface 1522 may contact the epidermis 1504 without deforming the epidermis 1504. This may improve accuracy of measurements taken by the miniaturized impedance sensor 400 by ensuring constant, complete contact with the epidermis 1504 without altering the epidermis 1504 in a way that may affect a measurement take from the epidermis 1504.

The top surface 1522 may have a surface area. The size of the surface area relative to a thickness of the epidermis 1504 may minimize an impact the wearable device 100 and/or miniaturized impedance sensor 400 may have on various physiological conditions, physiological parameters, and/or physiological constituents of the user. For example, in order to ensure accurate measurement, a bioimpedance sensor may be pressed against the epidermis 1504. However, pressing on the epidermis 1504 to hold the sensor against the epidermis 1504 may deform the dermal layers and/or various subdermal features of the user. The deformation may alter the physiological condition, physiological parameter, and/or physiological constituent the user desires to measure. For example, pressing on the epidermis 1504 may cause blood to be forced out of capillaries. Reducing the size of the electrodes may reduce the amount of force required to maintain sufficient contact between the electrodes and the epidermis 1504. This may in turn reduce a degree to which the epidermis 1504, the dermis 1506, and/or the hypodermis 1508 may be deformed. In an embodiment, an optimal surface area for minimally deforming the skin may range from 100 microns' to 500 microns' for each electrode. At this scale, the acclimation period for maximizing conductive contact between the miniaturized electrode 412 and the epidermis 1504 may be significantly reduced. In an embodiment, the acclimation period may be reduced from a range of 5 minutes to 15 minutes to a range less than or equal to 1 minute. In one embodiment, the acclimation period may be eliminated.

Miniaturization of the electrodes to the microscale as described herein may allow for optimal contact of the miniaturized electrodes 412 with the epidermis 1504. Optimal pressure of the miniaturized electrodes 412 into the epidermis 1504 may result in conformation of the epidermis around the miniaturized electrodes 412, up to and/or including contact of the epidermis 1504 with the interstitial well 414*a*. Conformation of the epidermis 1504 may optimally enhance signal response from the muscular-walled tube 1510 and/or fluid within the muscular-walled tube 1510 by the miniaturized electrodes 412. The pressure of the miniaturized electrodes 412 into the epidermis 1504 may be low enough to prevent and/or minimize shunting of capillary sphincters either open or close, which may generate physiological noise which may interfere with the signal from the muscular-walled tube 1510.

Incorporation of the miniaturized electrodes 412 into the miniaturized impedance sensor may allow for incorporation of a plurality of miniaturized electrodes 412 for measuring to a variety of subcutaneous depths. The miniaturized electrodes 412 may include a material that may be formed and/or manipulated on the scale of the surface area range. Such material may include CNTs. The CNTs may be formed into pillars with smooth surfaces on the scale of the surface area range. Additionally, the pillars may be electrically isolated from each other while still allowing for a plurality of electrodes for taking measurement at a plurality of depths.

A path of a current passed between the first miniaturized electrode and the second miniaturized electrode may depend on the size of the current and/or a separation distance between the first miniaturized electrode and the second miniaturized electrode, according to an embodiment. For example, the current may follow a first impedance path 1520a between a positive electrode 1514a and a first negative electrode 1514b. The first impedance path 1520a may pass through the epidermis 1504 and/or the dermis 1506. A measurement taken along the first impedance path 1520a may measure an impedance of the epidermis 1504 and/or the dermis 1506. A physiological condition, physiological parameter, and/or physiological constituent of the epidermis 1504 and/or the dermis 1506 may be determined by the measurement taken along the first impedance path 1520a. In an embodiment, the physiological condition may include a hydration condition of the user of the wearable device 100.

The current may follow a second impedance path 1520b between the positive electrode 1514a and a second negative electrode 1514c. The second impedance path 1520b may pass through the epidermis 1504, the dermis 1506, and/or the hypodermis 1508. A measurement taken along the second impedance path 1520b may measure an impedance of the epidermis 1504, the dermis 1506, and/or the hypodermis 1508. A physiological condition, physiological parameter, and/or physiological constituent of the epidermis 1504, the dermis 1506, and/or the hypodermis 1508 may be determined by the measurement take along the second impedance path 1520b. In an embodiment, the physiological parameter may include a body fat percentage of the user of the wearable device 100.

The current may follow a third impedance path 1520c between the positive electrode 1514a and a third negative electrode 1514d. The second impedance path 1520b may pass through the epidermis 1504, the dermis 1506, the hypodermis 1508, and/or the muscular-walled tube 1510. A measurement taken along the third impedance path 1520c may measure an impedance of the epidermis 1504, the dermis 1506, the hypodermis 1508, and/or the muscular-walled tube 1510. A physiological condition, physiological parameter, and/or physiological constituent of the epidermis 1504, the dermis 1506, the hypodermis 1508, and/or the muscular-walled tube 1510 may be determined by the measurement taken along the third impedance path 1520c. In an embodiment, the physiological constituent may include a blood glucose level of a user of the wearable device 100.

In an embodiment, a negative electrode closest to the positive electrode 1515a may be separated from the positive electrode 1514a by a distance such that the current passes through the epidermis 1504 without passing through the dermis 1506. The negative electrode closest to the positive electrode 1514a may be separated from the positive electrode 1514a by a distance such that the current passes through the epidermis 1504 and/or the dermis 1506 without passing through the hypodermis 1508, according to an embodiment. The negative electrode closest to the positive electrode 1514a may be separated from the positive electrode 1514a by a distance such that the current passes through the epidermis 1504, the dermis 1506, and/or the hypodermis 1508 without passing through the muscular-walled tube 1510. In an embodiment, the negative electrode closest to the positive electrode 1514a may be separated from the positive electrode 1514a by a distance such that the current passes through the epidermis 1504, the dermis 1506, the hypodermis 1508, and/or the muscular-walled tube 1510. In an embodiment, the negative electrode closest to the positive electrode 1514a may be separated from the positive electrode 1514a by a distance such that the current passes through the epidermis 1504, the dermis 1506, the hypodermis 1508, the muscular-walled tube 1510, and/or deeper tissue.

In one embodiment, the miniaturized impedance sensor 400 may be positioned against the user such that the current may flow perpendicular to the muscular-walled tube 1510 as the current passes from the positive electrode 1514a to the first negative electrode 1514b, the second negative electrode 1514c, and/or the third negative electrode 1514d. In another embodiment, the miniaturized impedance sensor 400 may be positioned against the user such that the current may pass through the muscular-walled tube 1510 along a length of the muscular-walled tube 1510 as the current passes from the positive electrode 1514a to the first negative electrode 1514b, the second negative electrode 1514c, and/or the third negative electrode 1514d.

In various embodiments, the first impedance path 1520a, the second impedance path 1520b, and/or the third impedance path 1520c may be symmetrical and/or smooth In another embodiment, the first impedance path 1520a, the second impedance path 1520b, and/or the third impedance path 1520c may vary over time across a region of the material as the conductive properties of the material change to change the path of least resistance for the current. The illustrated impedance paths may be provided to aid in describing the properties, features, and/or functions of various elements of embodiments throughout this disclosure. Accordingly, the illustrated impedance paths are not intended to be limiting of the path followed by a flow of current through a material.

In an embodiment, one or more miniaturized electrodes 412 may be electrically coupled to a processing device such that the processing device may assign the miniaturized electrode 412 to be the positive electrode and/or the negative electrode. The miniaturized impedance sensor 400 may include a number of rows of miniaturized electrodes 412, with a number of miniaturized electrodes 412 in each row. In some embodiments, a row of miniaturized electrodes 412 may include a single strip electrode. In some embodiments, a row of miniaturized electrodes 412 may include two or more miniaturized electrodes 412. For example, a row of miniaturized electrodes 412 may include 1 to 40 miniaturized electrodes 412, 5 to 35 miniaturized electrodes 412, 10 to 30 miniaturized electrodes 412, and/or 15 to 25 miniaturized electrodes 412. In one embodiment, a row of miniaturized electrodes 412 may include 5 miniaturized electrodes 412. Having a plurality of rows may allow for measurement of different depths within a material, substance, and/or body using the same sensor. Having a plurality of miniaturized electrodes 412 in each row may increase a surface area of the covered by the row, which may in turn reduce negative effects associated with, for example, debris and/or sweat. Having a plurality of miniaturized electrodes 412 in each row may also increase the structural strength of the miniaturized impedance sensor 400, such as the resistance of the miniaturized impedance sensor 400 to deforming and/or or breaking under various stresses.

The number of rows, the number of miniaturized electrodes 412 in each row, a spacing between rows, and/or a spacing between each miniaturized electrode 412 may correspond to a diameter and/or cross-sectional dimension of a body part on which a user wears the wearable device 100 incorporating the miniaturized impedance sensor 400. For example, the body part may be a wrist of the user. The spacing between the rows of miniaturized electrodes 412 spaced furthest from each other may be enough that current passed between the rows passes from an epidermal layer on an underside of the wrist and through an epidermal layer on a topside of the wrist opposite the underside. The underside of the wrist may face towards the user's body as the arm hangs in a resting position, and the topside may face away from the user's body as the arm hangs in a resting position. The spacing between each row of the miniaturized impedance sensor 400 may be such that the user may select depths into the wrist from the miniaturized impedance sensor 400 in increments ranging from 5 cm to 50 microns. Having a plurality of rows of miniaturized electrodes 412 may allow the miniaturized impedance sensor 400 to be adapted to different body parts and different users.

Different users may have differently-sized body parts. A thickness of a dermal layer may be different for one user for one body part than for a different user for the same body part. A depth of a muscular-walled tube may be different for one user for one body part than for a different user for the same body part. A thickness of a dermal layer of one body part may be different for one user than a thickness of a dermal layer of a different part for the same user. A depth of a muscular-walled tube may be different for one body part of a user than a depth of a muscular-walled tube for a different body part of the same user. The plurality of miniaturized electrodes 412 incorporated into the miniaturized impedance sensor 400 may allow for one design of the miniaturized impedance sensor 400, include dimensions, numbers of electrodes, and electrode spacing, to accommodate a wide variety of users and/or user body parts.

Having a plurality of rows of miniaturized electrodes 412, which each row selectable as a positive electrode or negative electrode, may allow for dynamic selecting of a depth to measure and/or a physiological condition, physiological parameter, and/or physiological constituent to measure. For example, for a fixed current, a spacing between the positive and negative electrode may be varied until a selected depth is reached. In one embodiment, for a fixed spacing, the current may be varied until a selected signal strength is reached. In one embodiment, the current and the spacing may be varied until a selected signal strength is reached. In an embodiment, a particular waveform associated with a particular physiological condition, physiological parameter, and/or physiological constituent may be established. The spacing and/or the current may be varied until the miniaturized impedance sensor 400 outputs the established waveform.

The miniaturized impedance sensor 400 may be configured to take measurements at various depths into the body part at various increments. A particular physiological condition, physiological parameter, and/or physiological constituent may correspond to a particular depth and/or range of depths into the body part. A memory device electrically coupled to the processing device may store data correlating a list of physiological conditions, physiological parameters, and/or physiological constituents with a list of depths into the body part. The processing device may obtain, from the memory device, the depth and/or range of depths associated with a selected physiological condition, physiological parameter, and/or physiological constituent. The processing device may choose a row of miniaturized electrodes 412 to act as a positive electrode and one or more rows of miniaturized electrodes 412 to act as negative electrodes corresponding to the depth associated with the selected physiological condition, physiological parameter, and/or physiological constituent. The processing device may activate the selected positive and negative electrode rows such that electrical current passes from the positive electrode row, through the body part to the associated depth, and to the negative electrode row or rows. The processing device may measure the impedance between the positive and negative electrode rows. The processing device may compare the resulting impedance to data stored in the memory device which may correlate a list of impedances with the list physiological conditions, physiological parameters, and/or physiological constituents and the list of depths.

In one embodiment, a body part includes a first subdermal feature at a first depth within the body part and a second subdermal feature at a second depth within the body part deeper than the first depth. In one example, the first subdermal feature and/or the subdermal feature is the epidermis 1504, the dermis 1506, the hypodermis 1508, the muscular-walled tube 1510, and/or deeper tissue. In another example, the first subdermal feature and the second subdermal feature are positioned in a same region of the body part.

In another embodiment, the miniaturized impedance sensor 400 may include a first miniaturized electrode 1514*a-d* to transmit an electronic signal through the body part as the user wears the band. In one example, the electronic signal is transmitted at a first power level or a second power level. In another embodiment, the miniaturized impedance sensor 400 includes a second miniaturized electrode 1514*a-d* spaced from the first miniaturized electrode at a first distance. The first distance may be a distance so that the second miniaturized electrode 1514*a-d* receives the electronic signal from the first miniaturized electrode 1514*a-d* through the first subdermal feature when the user wears the band. In one example, the electronic signal may bypass the second subdermal feature when it is received by the second miniaturized electrode 1514*a-d*. In another example, the first distance ma be less than first threshold distance to prevent the electric signal from penetrating into the body part to a depth of the second subdermal feature.

In another embodiment, the miniaturized impedance sensor 400 may include a third miniaturized electrode 1514*a-d* spaced from the first miniaturized electrode 1514*a-d* at a second distance. In one example, the second distance is greater than the first distance. In another example, the third miniaturized electrode 1514*a-d* receives the electronic signal from the first miniaturized electrode through the second subdermal feature when the user wears the band. In one example, when the first miniaturized electrode 1514*a-d* transmits the electric signal at the first power level and at the first distance from the second miniaturized electrode 1514*a-d*, the first miniaturized electrode generates a circular electric field in the body part as the user wears the band. In another example, when the first miniaturized electrode 1514*a-d* transmits the electric signal at the second power level and at the second distance from the second miniaturized electrode 1514*a-d*, the first miniaturized electrode 1514*a-d* generates an elliptical electric field in the body part as the user wears the band.

In another example, the first miniaturized electrode 1514*a-d* and the second miniaturized electrode 1514*a-d* or the first miniaturized electrode 1514*a-d* and the third miniaturized electrode 1514*a-d* are positioned in a band of a wearable device such that: as the user wears the band a first electric field between the first miniaturized electrode 1514*a-d* and the second miniaturized electrode 1514*a-d* or between the first miniaturized electrode 1514*a-d* and the third miniaturized electrode 1514*a-d* is aligned parallel to a muscular-walled tube 1510 of a body part, such as the hypodermis 1508; or a second electric field between the first miniaturized electrode 1514*a-d* and the second miniaturized electrode 1514*a-d* or between the first miniaturized electrode 1514*a-d* and the third miniaturized electrode 1514*a-d* is aligned perpendicular to the muscular-walled tube 1510.

In one example, a processing device coupled to the miniaturized electrode 1514*a-d* may automatically select a pair of miniaturized electrodes 1514*a-d* from the array of miniaturized electrodes 1514*a-d* based on an impedance signal generated by the pair of miniaturized electrodes 1514*a-d*. In one example, the first miniaturized electrode 1514*a-d* is configured in the miniaturized impedance sensor to transmit the electronic signal at a discreet frequency or at a spectrum of different frequencies. In another example, the processing device may measure an impedance of the first subdermal feature or the second subdermal feature for a spectrum of frequencies by transmitting the electronic signal from the first miniaturized electrode 1514*a-d* at the first power level or the second power level and across the spectrum of frequencies.

In another example, the processing device may iteratively select transmitting the electronic signal between the first miniaturized electrode 1514*a-d* and the second miniaturized electrode 1514*a-d* and between the first miniaturized electrode 1514*a-d* and the third miniaturized electrode 1514*a-d* until the miniaturized impedance sensor detects the electronic signal indicative of a threshold impedance measurement. In another example, the processing device may iteratively select a frequency from a spectrum of different frequencies until the miniaturized impedance sensor detects the electronic signal indicative of the threshold impedance measurement. The threshold impedance measurement may correspond to a measurement taken at the first subdermal feature or the second subdermal feature.

In another example, the processing device may apply power via a power source to the first miniaturized electrode such that the first miniaturized electrode 1514*a-d* transmits a first signal when the user selects, via the user interface, a first measurement corresponding to the first subdermal feature. In another example, the processing device may apply power via the power source to the second miniaturized electrode 1514*a-d* such that the second miniaturized electrode 1514*a-d* transmits a second signal when the user selects, via a user interface, a second measurement corresponding to the second subdermal feature. In another example, a processing device may select a depth from the multiple depths at which the impedance is measured. The processing device may select the depth that corresponds to a subdermal feature within the body part based on a spacing between the first miniaturized electrode 1514*a-d* and the second miniaturized electrode 1514*a-d*.

In another example, the processing device may measure impedance at a number of depths within the body part as the user wears the band, where the number of depths correspond to a number of electrically separate miniaturized electrodes of an array of miniaturized electrodes. In another example, the processing device may select a pair of miniaturized electrodes based on a difference between a first signal to noise ratio corresponding to a first subdermal feature of the body part and a second signal to noise ratio corresponding to a second subdermal feature of the body part. In another example, the processing device may compare the impedance of the electronic signal to defined impedance values measured using different miniaturized electrodes 1514*a-d*. In another example, the defined impedance values may be associated with one or more features of the body part. In another example, the processing device may correlate a change in the impedance with a change in the body part 1508. The body part 1508 may include the muscular-walled tube 1510 within the body part. The muscular-walled tube 1510 may have blood flowing through the muscular-walled tube 1510. The change may include a change in an amount of glucose in the blood flowing through the muscular-walled tube 1510.

Figure 16B:
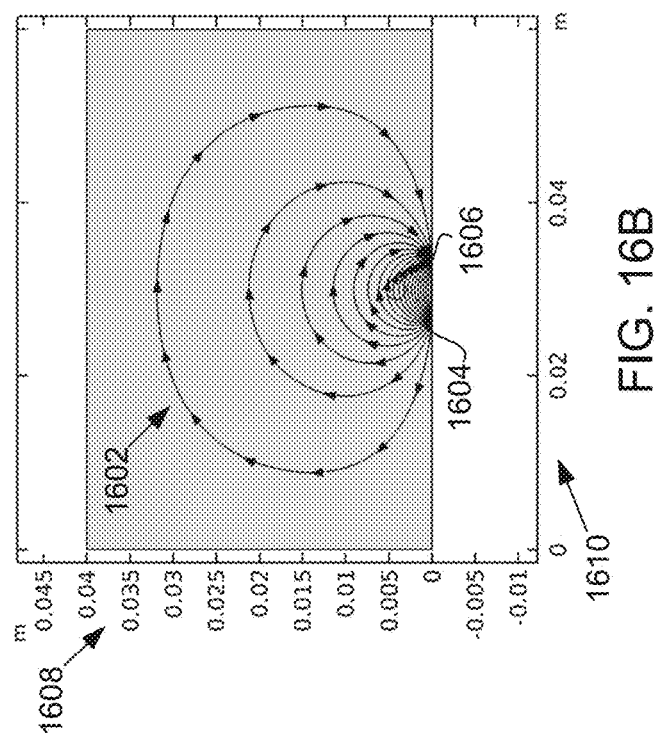
FIG. 16B illustrates a graph showing electric field lines between electrodes of the miniaturized impedance sensor at a second to separation distance, according to an embodiment.
Figure 16A:
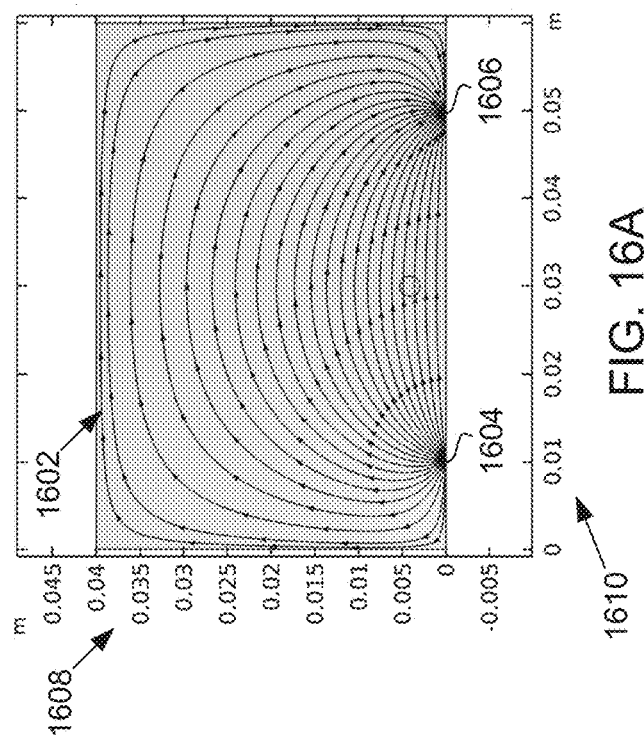
FIG. 16A illustrates a graph showing electric field lines between electrodes of the miniaturized impedance sensor at a first separation distance, according to an embodiment.

FIGS. 16A-B illustrate graphs showing electric field lines 1602 between a first miniaturized electrode 1604 and a second miniaturized electrode 1606 of a miniaturized impedance sensor such as the miniaturized impedance sensor 400. The first miniaturized electrode 1604 and/or the second miniaturized electrode 1606 may be the same as or similar to the miniaturized electrode 412 described and illustrated throughout this disclosure. A vertical axis 1608 may show a depth the electric field lines 1602 penetrate into a substance in meters, and a horizontal axis 1610 may show a separation distance between the first miniaturized electrode 1604 and the second miniaturized electrode 1606 in meters. A density of the electric field lines 1602 may indicate a strength of an electric field at a point in the substance. In an embodiment, the substance may include a dermal and/or subdermal region of a user wearing a wearable device such as is described and/or illustrated throughout this disclosure. FIG. 16A illustrates the first electrode 1604 and the second electrode 1606 separated by approximately 0.04 m. FIG. 16B illustrates the first electrode 1604 and the second electrode 1606 separated by approximately 0.01 m.

A greater separation between the first electrode 1604 and the second electrode 1606 may correlate with a deeper penetration of the electric field into the substance. For example, a separation of 0.01 m may correspond to a penetration of 0.03 m, whereas a separation 0.04 m may correspond to a penetration of at least 0.04 m. As the separation distance between the first electrode 1604 and the second electrode 1606 changes, a shape of the electric field may also change. For example, as the separation distance increases from 0.01 m to 0.04 m, the shape of the electric field may change from circular to oblong. A particular shape of the shape of the electric field may be suited for a particular a physiological condition, physiological parameter, and/or physiological constituent. For example, an oblong shape may be suited to measure a physiological condition, physiological parameter, and/or physiological constituent that corresponds to an average measurement of a volume. A circular shape may be suited to measure a physiological condition, physiological parameter, and/or physiological constituent that corresponds to a cross-sectional area. The shape of the electric field may be varied by the number and/or relative positions of the electrodes. For example, a single positive electrode may be positioned between two negative electrodes. The spacing of the electrodes and the strength of the current may create two side-by-side circular electric fields. One electric field may pass through a cross-section of a vein; the other electric field may pass through a cross-section of an artery. The side-by-side arrangement may be used to compare blood constituents of blood flowing to a body part with blood flowing from the body part.

The miniaturized impedance sensor may have a number of positive-negative pairs of miniaturized electrodes, which may allow for selection of the physiological condition, physiological parameter, and/or physiological constituent to be measured by the miniaturized impedance sensor. The spacing between the positive-negative pair may determine the depth from which the miniaturized impedance sensor may take a measurement. Incorporating a number of positive-negative pairs of miniaturized electrodes, each pair having a different spacing from each other pair, may accordingly allow for measurement to different depths by a single miniaturized impedance sensor. For example, a first pair of miniaturized electrodes of the miniaturized impedance sensor may be separated by approximately 0.01 m, and a second pair of miniaturized electrodes of the miniaturized impedance sensor may be separated by approximately 0.04 m. The first pair of miniaturized electrodes may take a measurement corresponding to a physiological condition at 0.005 m beneath a surface of skin of a user, such as a hydration condition of the user. The first pair of nano electrodes may measure an impedance of the skin. The second pair of nano electrodes may take a measurement corresponding to a physiological condition at 0.01 m beneath the surface of the skin, where a vein or artery may be located. The second pair of nano electrodes may measure an impedance of blood in the vein or artery, which may be processed by a processing device to determine respective quantities of various constituents of the blood.

Figures 17A, 17B:
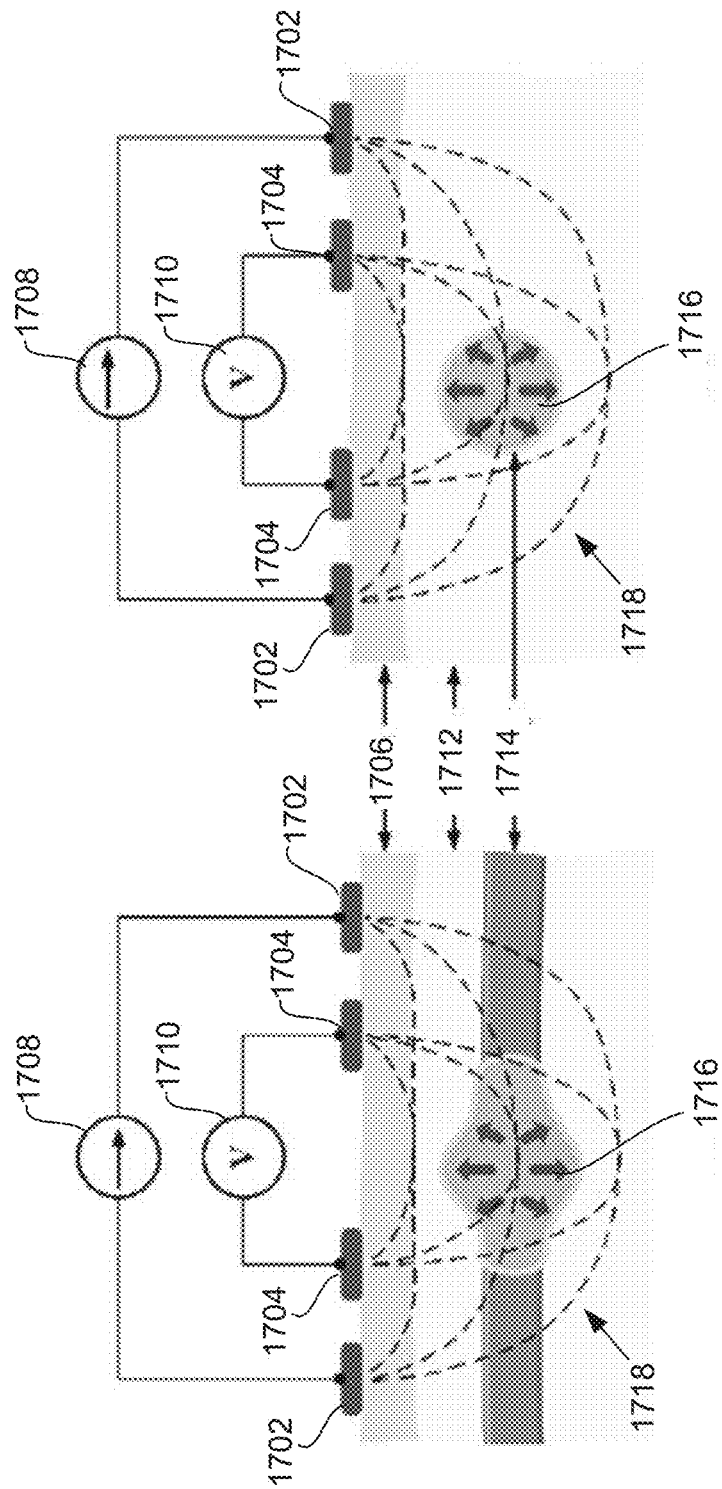
FIG. 17A illustrates miniaturized electrodes against skin of a user aligned parallel to a muscular-walled tube, according to an embodiment.
FIG. 17B illustrates miniaturized electrodes against skin of a user aligned perpendicular to a muscular walled tube, according to an embodiment.

FIGS. 17A-B illustrate a first set of miniaturized electrodes 1702 and a second set of miniaturized electrodes 1704 against a user 1706, according to an embodiment. Some of the features in FIGS. 17A-B are the same as or similar to some of the features in FIGS. 1-16B as noted by same and/or similar reference characters, unless expressly described otherwise. FIG. 17A illustrates impedance paths 1718 aligned parallel to an artery 1714. FIG. 17B illustrates impedance paths 1718 aligned perpendicular to the artery 1714. The first set of electrodes 1702 may be electrically coupled to a current source 1708. In an embodiment, the current source 1708 may include a voltage to current converter, which may be the same as or similar to the voltage to current converter 1806 described and/or illustrated regarding FIG. 18. The second set of electrodes 1704 may be electrically coupled to a voltmeter 1710. In an embodiment, the voltmeter may include an operational amplifier, which may be the same as or similar to the operational amplifier 1816 described and/or illustrated regarding FIG. 18. The first set of miniaturized electrodes 1702 may cause a current to be passed through the skin 1706, a subcutaneous tissue 1712, and/or the artery 1714. The second set of miniaturized electrodes 1704 may be placed between the two electrodes of the first set of miniaturized electrodes 1702 to measure a voltage between the two electrodes of the first set of miniaturized electrodes 1702. The resulting voltage may be subsequently used to determine an impedance of the skin 1706, the subcutaneous tissue 1712, and/or the artery 1714. In an embodiment, an impedance of the artery 1714 may include an impedance of substances found within the artery 1714, such as blood and/or various blood constituents.

Arrows 1716 may indicate an expansion of the artery 1714 as blood is pumped through the artery 1714 by a heart. The artery may expand according to a heartbeat of the heart. Expansion of the artery 1714 may change a volumetric composition of a volume for which the impedance is measured. The change in the volumetric composition may change the impedance in cadence with the heartbeat. Accordingly, changes in impedance may be caused by the heartbeat, and may be correlated directly with a condition, parameter, and/or constituent of the heart and/or circulatory system.

Figures 17C, 17D:
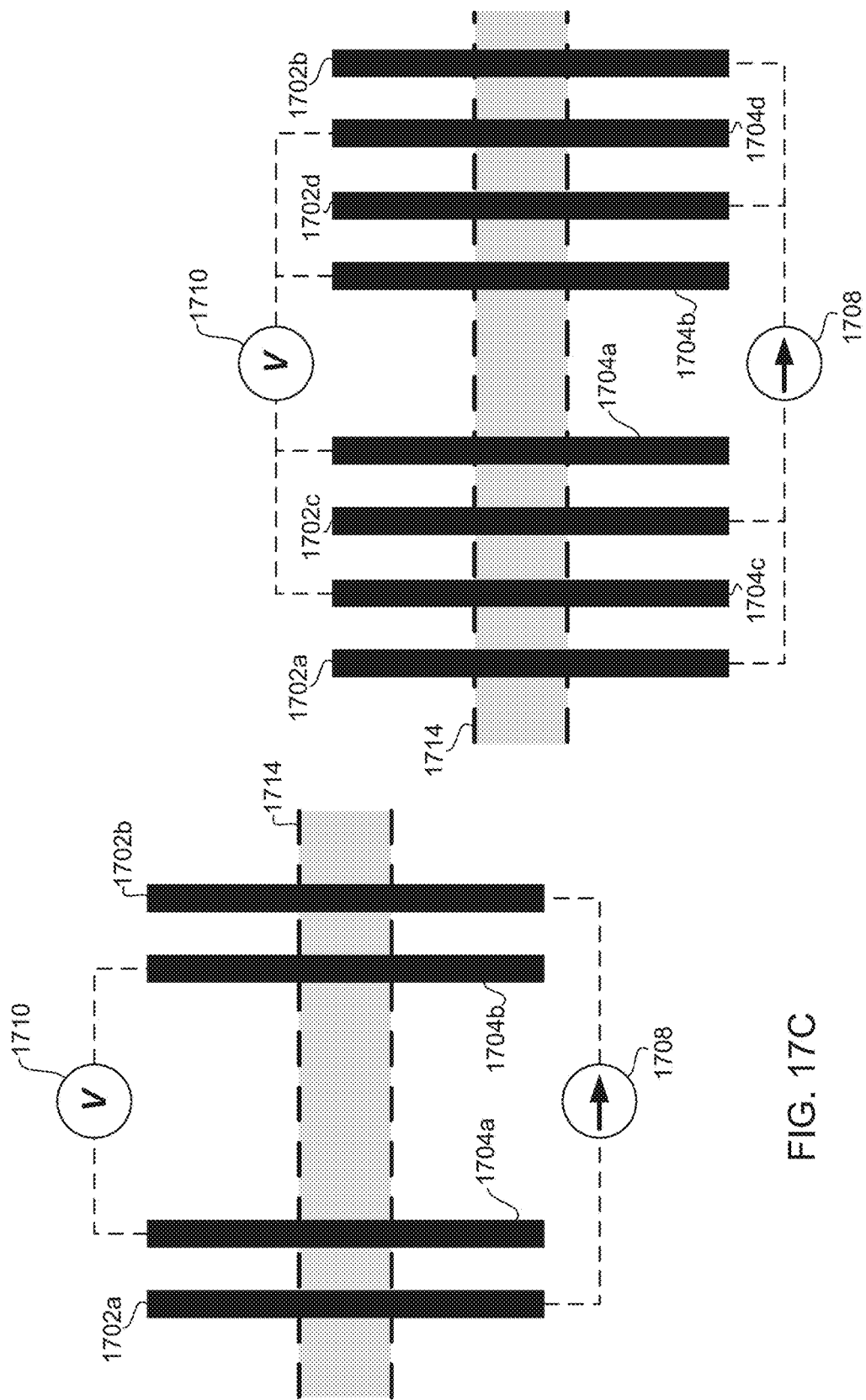
FIG. 17C illustrates an electronic schematic of the miniaturized electrodes described regarding FIGS. 17A-B, according to an embodiment.
FIG. 17D illustrates interdigitated miniaturized electrodes, according to an embodiment.

17C illustrates an electronic schematic of the miniaturized electrodes described regarding FIGS. 17A-B, according to an embodiment. Some of the features in FIG. 17C are the same as or similar to some of the features in FIGS. 1-17B as noted by same and/or similar reference characters, unless expressly described otherwise. The first set of miniaturized electrodes 1702 and second set of miniaturized electrodes 1704 may be structured as bars. The bars may be aligned perpendicular to a length of the artery 1714. The first set of miniaturized electrodes 1702 may include the first miniaturized electrode 1702a and the second miniaturized electrode 1702b. The second set of miniaturized electrodes 1704 may include the third miniaturized electrode 1704a and the fourth miniaturized electrode 1704b.

The second set of miniaturized electrodes 1704 may be set between the first miniaturized electrode 1702a and the second miniaturized electrode 1702b. The third miniaturized electrode 1704a may be positioned closer to the first miniaturized electrode 1702a than to the other miniaturized electrode of the second set, miniaturized electrode 1704b. Similarly, the fourth miniaturized electrode 1704b may be positioned closer to the second miniaturized electrode 1702b than to the third miniaturized electrode 1704a. For example, a distance between the miniaturized electrodes of the first set 1702 may range from 0.5 cm to 3 cm, from 0.75 cm to 2 cm, and/or from 1 cm to 1.5 cm. A distance between the miniaturized electrodes of opposing sets, such as between the first miniaturized electrode 1702a and the third miniaturized electrode 1704a, and/or between the second miniaturized electrode 1702b and the fourth miniaturized electrode 1704b, may be a fraction of the distance between the miniaturized electrodes of the first set 1702. For example, a distance between the first miniaturized electrode 1702a and the third miniaturized electrode 1704a may range from 0.05 cm to 1 cm, from 0.075 cm to 0.75 cm, and/or from 0.1 cm to 0.5 cm. Similar ranges may apply to a distance between the second miniaturized electrode 1702b and the fourth miniaturized electrode 1704b. In one embodiment, the distance between the miniaturized electrodes of the first set 1702 may be 1 cm and the distance between the miniaturized electrodes of opposing sets may be 0.1 mm.

A minimum distance between neighboring electrodes of opposing sets, such as between the first miniaturized electrode 1702a and the third miniaturized electrode 1704a, and/or between the second miniaturized electrode 1702b and the fourth miniaturized electrode 1704b may be related to a minimum distance at which capacitive coupling is prevented between the first set of miniaturized electrodes 1702 and the second set of miniaturized electrodes 1704. The greater the distance between neighboring electrodes of opposing sets, the less likely capacitive coupling will occur. However, a maximum distance between neighboring electrodes of opposing sets may be related to a distance greater than that at which a signal to noise ratio is less than or equal to 1. The smaller the distance between neighboring electrodes of opposing sets, the greater the signal to noise ratio may be. Accordingly, an optimal distance between neighboring electrodes of opposing sets may be a minimum distance at which capacitive coupling is prevented. Additionally, a distance between the miniaturized electrodes of the second set 1704 may be greater than the distance between neighboring electrodes of opposing sets. As described herein, a distance between the miniaturized electrodes of the first set may correspond to a depth to which measurements may reach.

FIG. 17D illustrates interdigitated miniaturized electrodes, according to an embodiment. Some of the features in FIG. 17D are the same as or similar to some of the features in FIGS. 1-17C as noted by same and/or similar reference characters, unless expressly described otherwise. In addition to the first miniaturized electrode 1702a and the second miniaturized electrode 1702b, the first set of miniaturized electrodes 1702 may include the fifth miniaturized electrode 1702c and the sixth miniaturized electrode 1702d. In addition to the third miniaturized electrode 1704a and the fourth miniaturized electrode 1704b, the second set of miniaturized electrodes 1704 may include the seventh miniaturized electrode 1704c and the eighth miniaturized electrode 1704d. The first set of miniaturized electrodes 1702 and the second set of miniaturized electrodes may be interdigitated. Accordingly, one miniaturized electrode of one set may be positioned between and adjacent to two miniaturized electrodes of the other set. For example, the third miniaturized electrode 1704a may be positioned between and adjacent to the first miniaturized electrode 1702a and the fifth miniaturized electrode 1702c, and so forth. Additionally, similar to the embodiment depicted in FIG. 17C, a distance between the miniaturized electrodes of the second set 1704 may be greater than the distance between neighboring electrodes of opposing sets.

Interdigitated electrodes may enable a user to select a depth to which measurement may be taken. For example, for a first depth, the user may select as the voltage electrodes the third miniaturized electrode 1704a and the fourth miniaturized electrode 1704b, and as the current electrodes the fifth miniaturized electrode 1702c and the sixth miniaturized electrode 1702d. For a second depth, the user may select as the voltage electrodes the seventh miniaturized electrode 1704c and the fourth miniaturized electrode 1704b, and as the current electrodes the first miniaturized electrode 1702a and the fifth miniaturized electrode 1702c. For a third depth, the user may select as the voltage electrodes the seventh miniaturized electrode 1704c and the eighth miniaturized electrode 1704d, and as the current electrodes the first miniaturized electrode 1702a and the second miniaturized electrode 1702b. One or more of the miniaturized electrodes may be connected to a switch between the miniaturized electrode and the current source or the voltmeter. The user may select various of the miniaturized electrodes via software, which may activate and/or deactivate the switch based on a selection by the user.

Interdigitated electrodes may enable a user to tune the signal to noise ratio based on a material and/or substance to be measured by the miniaturized electrodes. For example, noise may include impedance of other tissue than a tissue of interest. Noise may include electrical signals generated by the body. Noise may include harmonics from the signal across the current electrodes. Noise may include capacitive coupling, inductive coupling, internal current leakage of the circuitry, and so forth. As discussed above, capacitive coupling may be staved off by ensuring an appropriate spacing between miniaturized electrodes of opposing sets. However, capacitive coupling may also be related to a material between the miniaturized electrodes. For a set of miniaturized electrodes with an air gap, a minimum spacing between adjacent miniaturized electrodes of opposing sets to prevent capacitive coupling may range from 1 times an average height of the miniaturized electrodes to 3 times and average height of the miniaturized electrodes, from 1.5 times an average height of the miniaturized electrodes to 2.5 times an average height of the miniaturized electrodes, or may be 2 times an average height of the miniaturized electrodes. In an embodiment, the minimum spacing between miniaturized electrodes of opposing sets to prevent capacitive coupling may be 2.5 times an average height of the miniaturized electrodes. However, as described herein, one or more various materials may be disposed between adjacent miniaturized electrodes of opposing sets, such as a polymer and/or tissue to be measured by the miniaturized electrodes. Accordingly, interdigitation of the miniaturized electrodes may allow for tuning of the spacing between adjacent miniaturized electrodes of opposing sets to minimize the effect of capacitive coupling and/or other noise.

Figure 17E:
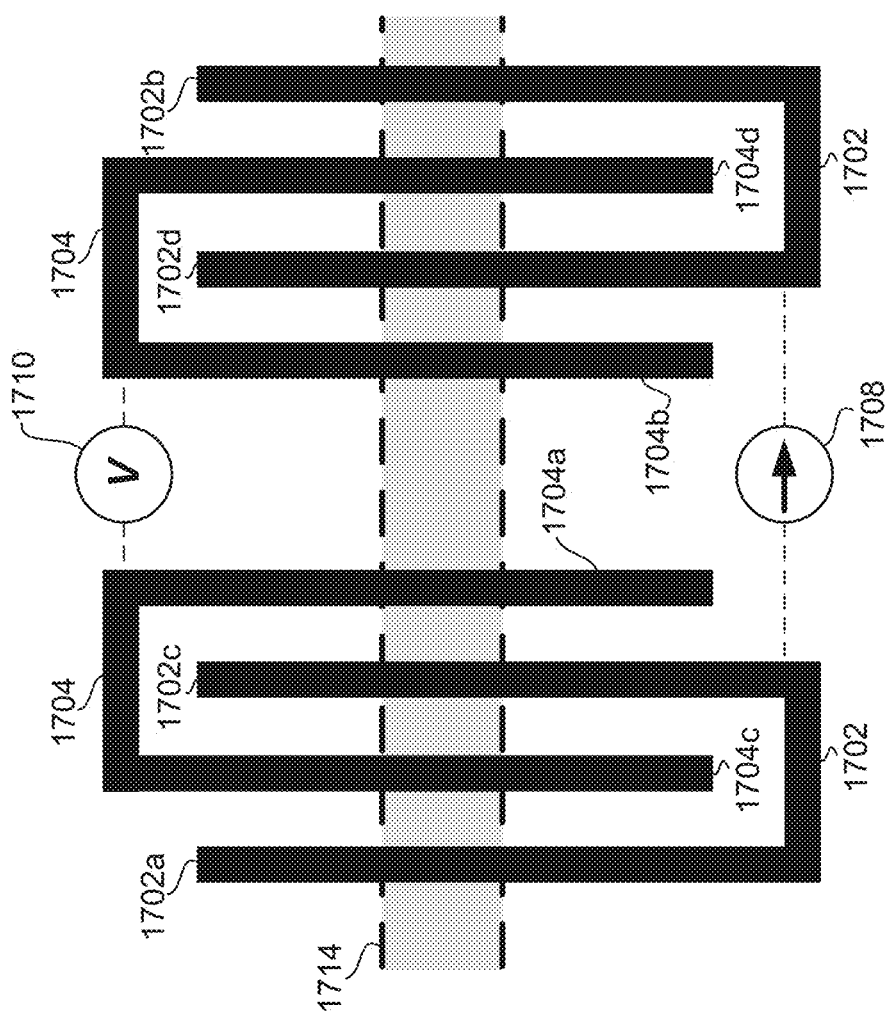
FIG. 17E illustrates sets of miniaturized electrodes with interdigitated fingers, according to an embodiment.

FIG. 17E illustrates sets of miniaturized electrodes with interdigitated fingers, according to an embodiment. Some of the features in FIG. 17E are the same as or similar to some of the features in FIGS. 1-17D as noted by same and/or similar reference characters, unless expressly described otherwise. In various embodiments, miniaturized electrodes of the first set 1702 may be interconnected by electrode material, and miniaturized electrodes of the second set 1704 may be interconnected by electrode material. For example, the first miniaturized electrode 1702a and the fifth miniaturized electrode 1702c may be interconnected by electrode material, and so forth. The first miniaturized electrode 1702a and the fifth miniaturized electrode 1702c may be fingers of the first set of miniaturized electrodes 1702, and so forth. Such embodiments may have similar effects and/or features as those described regarding the interdigitated miniaturized electrodes of FIG. 17D. Additionally, the sets of miniaturized electrodes with interdigitated fingers depicted in FIG. 17E may allow for further enhancement of the signal to noise ratio. The positioning of a finger of the second set of miniaturized electrodes 1704 adjacent to and between two fingers of the first set of miniaturized electrodes 1702 may enhance an amount of signal detected by the second set of miniaturized electrodes 1704. The proximity of the fingers of the opposing sets of miniaturized electrodes may increase a ratio of signal to background noise relative to, for example, an impedance sensor including pads which may cover a similar surface area.

In one example, a miniaturized impedance sensor may include a row of interdigitated miniaturized electrodes alternating between a miniaturized electrode 1702a or 1702c of a first set of miniaturized electrodes 1702 and another miniaturized electrode 1704a or 1704c of a second set of miniaturized electrodes 1704. In another example, a first end miniaturized electrode 1702a may be positioned at a first end of the row of interdigitated miniaturized electrodes and a second end miniaturized electrode 1704a may be positioned at a second end of the row of interdigitated miniaturized electrodes. In another example, the first set of miniaturized electrodes and/or the second set of miniaturized electrodes may include middle miniaturized electrodes 1702c and 1704c adjacent to each other and positioned at a middle of the row of interdigitated miniaturized electrodes. In another example, the first set of miniaturized electrodes may transmit an electrical signal and the second set of miniaturized electrodes may receive the electrical signal, or vice versa.

In one embodiment, a miniaturized electrode 1702a-1702d or 1704a-1704d maybe a miniaturized electrode strip or a miniaturized electrode pillar. In one example, a contact surface of the miniaturized electrode strip for contacting the body part may be formed by a length of the miniaturized electrode strip and a width of the miniaturized electrode strip. In another example, a thickness of the miniaturized electrode strip may extend from the band towards the body part as a user wears a wearable device that the miniaturized electrode 1702a-1702d and/or 1704a-1704d are integrated into. In another example, a contact surface of the miniaturized electrode pillar may include a dot defined by a length and a width of the miniaturized electrode pillar. In another example, a height of the miniaturized electrode pillar is configured to extend from a band of a wearable device towards the body part as the user wears the wearable device.

In another example, the first set of miniaturized electrodes 1702 or the second set of miniaturized electrodes 1704 comprises a forked miniaturized electrode. The forked miniaturized electrode may include two strips 1702a and 1702c, 1702b and 1702d, 1704a and 1704c, or 1704b and 1704d that extending parallel to the dermal layer of a body part. The two strips may be interconnected by an interconnecting strip of miniaturized electrode material. In another example, the first forked miniaturized electrode may be positioned in the band to face an opposite direction as the second forked miniaturized electrode such that the first forked miniaturized electrode and the second forked miniaturized electrode are interdigitated. In another example, the first set of miniaturized electrodes 1702 forms a first circuit and the second set of miniaturized electrodes 1704 forms a second circuit. The first circuit and the second circuit may be electronically isolated from each other in the miniaturized impedance sensor. In another example, the first set of miniaturized electrodes 1702 and the second set of miniaturized electrodes 1704 form a circuit via the body part in a miniaturized impedance sensor.

In another example, the first set of miniaturized electrodes 1702 may pass a current through the body part as the user wears the band and the second set of miniaturized electrodes 1704 measures an electric field in the body part as the user wears the band. In another example, the miniaturized impedance sensor may include a row of interdigitated miniaturized electrodes alternating between a miniaturized electrode of a first set of miniaturized electrodes 1702 and another miniaturized electrode of a second set of miniaturized electrodes 1704. In another example, a first electrode pad of the first set of miniaturized electrodes 1702 or the second set of miniaturized electrodes 1704 may be situated against the body part along a first plane and a second electrode pad of the first set of miniaturized electrodes 1702 or the second set of miniaturized electrodes 1704 may be situated against the body part along a second plane. The first plane and the second plane intersect.

In another example, the first set of miniaturized electrodes 1702 or the second set of miniaturized electrodes 1704 may include a first miniaturized electrode strip and a second miniaturized electrode strip. The first miniaturized electrode strip may be aligned approximately parallel to the second miniaturized electrode strip. The first miniaturized electrode strip and the second miniaturized electrode strip may be monolithically coupled to each other by an interconnecting strip. The interconnecting strip may be aligned approximately perpendicular to the first miniaturized electrode strip and the second miniaturized electrode strip. In another example, the first set of miniaturized electrodes 1702 or the second set of miniaturized electrodes 1704 may include a row of two or more miniaturized electrode pillars having a greater height than length or width. A contact surface of one of the two or more miniaturized electrode pillars may include a dot defined by a length of the miniaturized electrode pillar and a width of the miniaturized electrode pillar. The miniaturized electrode pillar may include the contact surface to contact the body part as the user wears the band. The miniaturized electrode pillar may extend towards the body part from the band as the user wears the band. In another example, a row of interdigitated miniaturized electrodes may be positioned within a band of the wearable device and run parallel to a diameter of the muscular-walled tube as the user wears the band or run perpendicular to the diameter of the muscular-walled tube as the user wears the band.

Figure 17F:
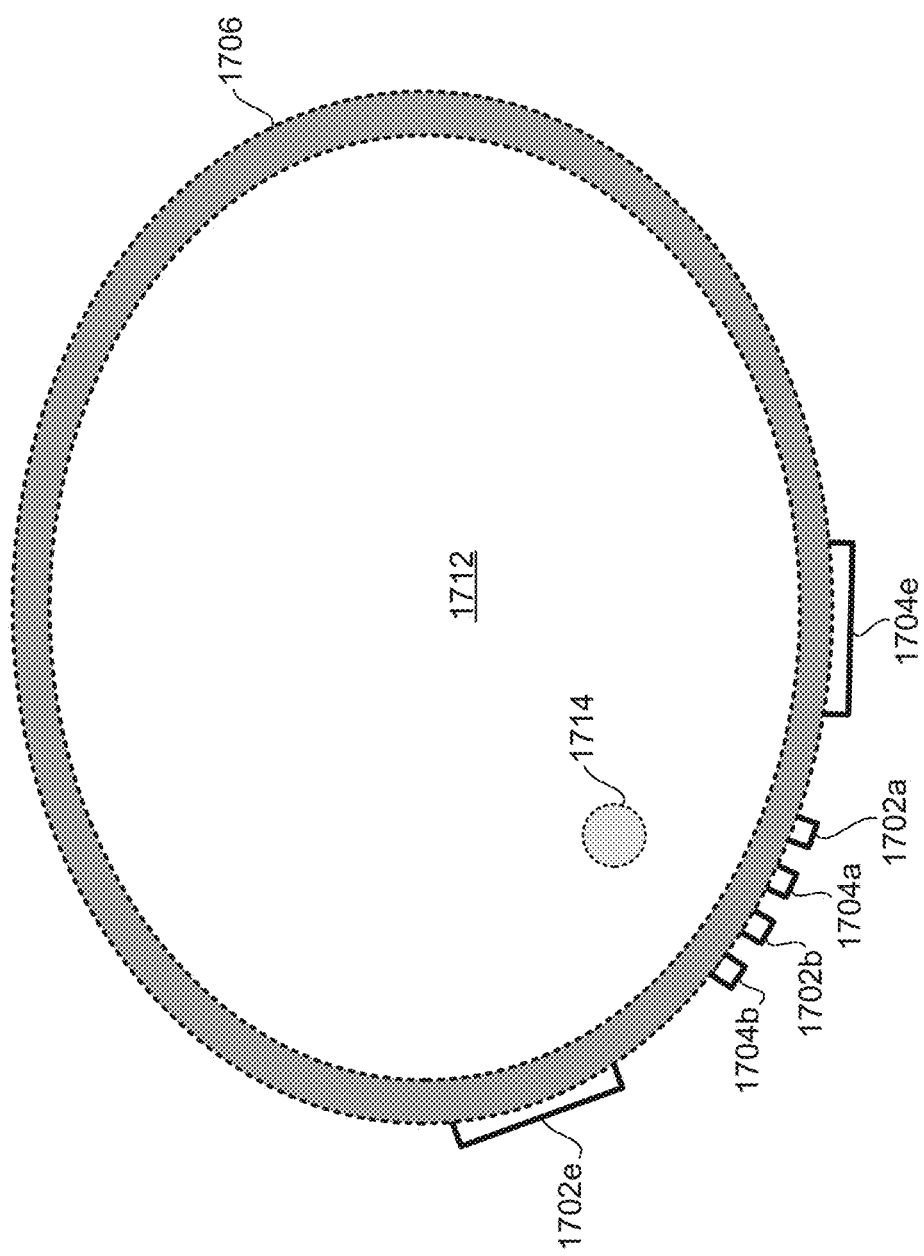
FIG. 17F illustrates interdigitated miniaturized electrodes between electrode pads, according to an embodiment.

FIG. 17F illustrates interdigitated miniaturized electrodes between electrode pads, according to an embodiment. Some of the features in FIG. 17F are the same as or similar to some of the features in FIGS. 1-17E as noted by same and/or similar reference characters, unless expressly described otherwise. The first set of miniaturized electrodes 1702 may additionally include a first impedance pad 1702e. The second set of miniaturized electrodes 1704 may additionally include a second impedance pad 1702e. The first impedance pad 1702e and/or the second impedance pad 1704e may have surface areas ranging from 0.5 cm$^2$ to 2 cm$^2$. The first impedance pad 1702e and the second impedance pad 1704e may be positioned on opposite sides of the other miniaturized electrodes. In various embodiments, placing the first impedance pad 1702e along an opposite side of the artery 1714 from the second impedance pad 1704e may allow a user to tune an impedance measurement to the artery 1714, eliminating noise such as background noise, physiological noise, and so forth.

Figure 18:
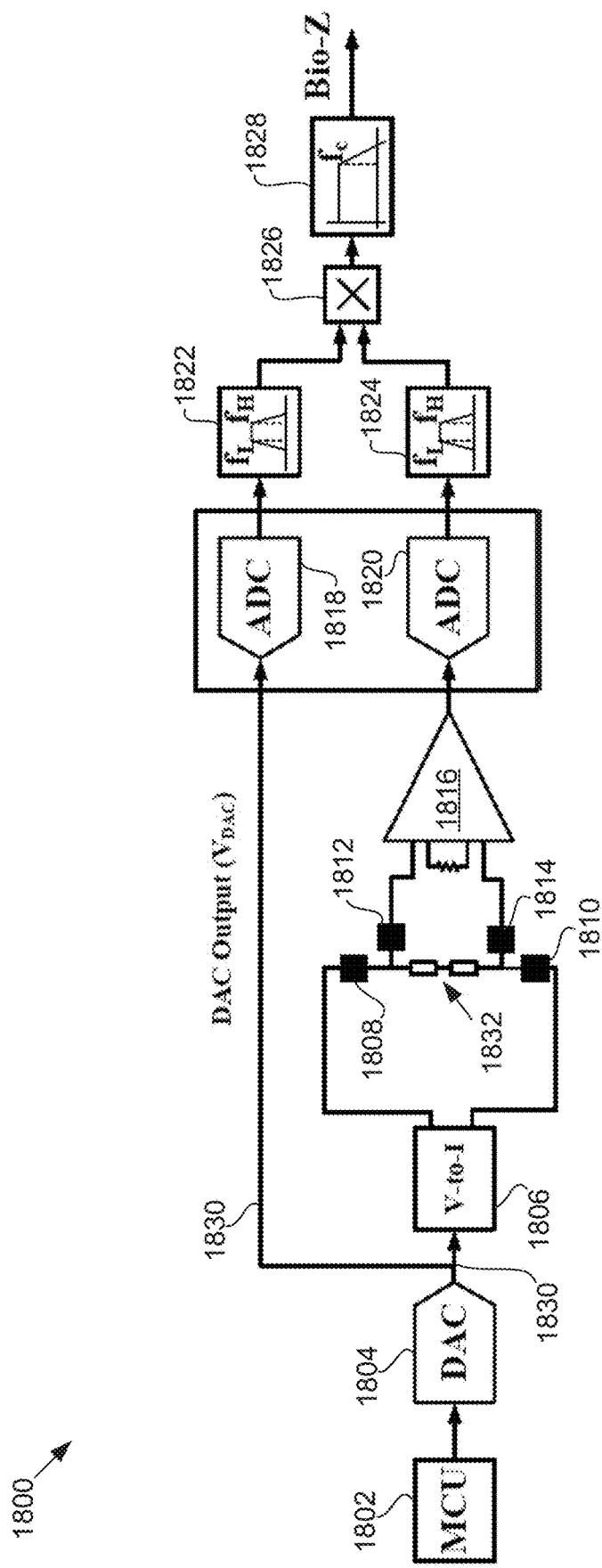
FIG. 18 illustrates a controls schematic for the miniaturized impedance sensor, according to an embodiment.

FIG. 18 illustrates a controls schematic for a bioimpedance circuit 1800, according to an embodiment. Some of the features in FIG. 18 are the same as or similar to some of the features in FIGS. 1-17E as noted by same and/or similar reference characters, unless expressly described otherwise. The bioimpedance circuit 1800 may include a microcontroller 1802 (MCU 1802), a digital-to-analog converter 1804 (DAC 1804), a voltage-to-current converter 1806 (V to I 1806), a first miniaturized electrode 1808, a second miniaturized electrode 1810, a third miniaturized electrode 1812, a fourth miniaturized electrode 1814, an operational amplifier 1816 (op amp 1816), a first analog-to-digital converter 1818 (first ADC 1818), a second analog-to-digital converter 1820 (second ADC 1820), a first bandpass filter 1822 (first BPF 1822), a second bandpass filter 1824 (second BPF 1824), a signal mixer 1826, and a low pass filter 1828 (LPF 1828). In an embodiment, one or more of the first miniaturized electrode 1808, the second miniaturized electrode 1810, the third miniaturized electrode 1812, and the fourth miniaturized electrode 1814 may be the same as or similar to the miniaturized electrode 412 described and/or illustrated throughout this disclosure. The bioimpedance circuit 1800 may be implemented for generating signals to measure physiological characteristics, detecting the resulting signals, and transmitting the signals to a processing device.

In an embodiment, the MCU 1802 may pass an electronic signal 1830 to the DAC 1804. After the DAC 1804, the electronic signal 1830 may be split. A portion of the electronic signal 1830 may be directed to the first ADC 1818, and a portion of the electronic signal 1830 may be directed to the V to I 1806. The portion of the electronic signal 1830 passed to the first ADC 1818 may have a first voltage measurement matching an output voltage of the DAC 1804. The V to I 1806 may convert the output voltage of the DAC 1804 to a current. In an embodiment, the current may be 500 microamps pulsing at a frequency of 8 kHz. The current may be passed from the V to I 1806, through the first miniaturized electrode 1808, through an impeding substance 1832, through the second miniaturized electrode 1810, and back into the V to I 1806. The third miniaturized electrode 1812 and the fourth miniaturized electrode 1814 may be disposed against the impeding surface 1832 between the first miniaturized electrode 1808 and the second miniaturized electrode 1810. In an embodiment, the first miniaturized electrode 1808 and the second miniaturized electrode 1810 may be part of a first set of miniaturized electrodes. The first set of miniaturized electrodes may be similar to the first set of miniaturized electrodes 1702 described and/or illustrated regarding FIGS. 17A-B, and/or may include the miniaturized electrodes 412 described and illustrated throughout this disclosure. In an embodiment, the third miniaturized electrode 1812 and the fourth miniaturized electrode 1814 may be part of a second set of miniaturized electrodes. The second set of miniaturized electrodes may be similar to the second set of miniaturized electrodes 1704 described and/or illustrated regarding FIGS. 17A-B, and/or may include the miniaturized electrodes 412 described and illustrated throughout this disclosure.

The second set of miniaturized electrodes may be electrically coupled to the op amp 1816. In an embodiment, the op amp 1816 may include a comparator. The op amp 1816 may output a voltage to the second ADC 1820 based on a voltage difference between the third miniaturized electrode 1812 and the fourth miniaturized electrode 1814. The first ADC 1818 and the second ADC 1820 may convert the input from analog to digital signals. The digital signals may be passed to the first BPF 1822 and the second BPF 1824, respectively. The digital signals may be combined into a single signal by the signal mixer 1826, passed through the LPF 1828, and then passed to a processing device for calculation impedance and correlation with a physiological condition, physiological parameter, and/or physiological constituent.

Figure 19:
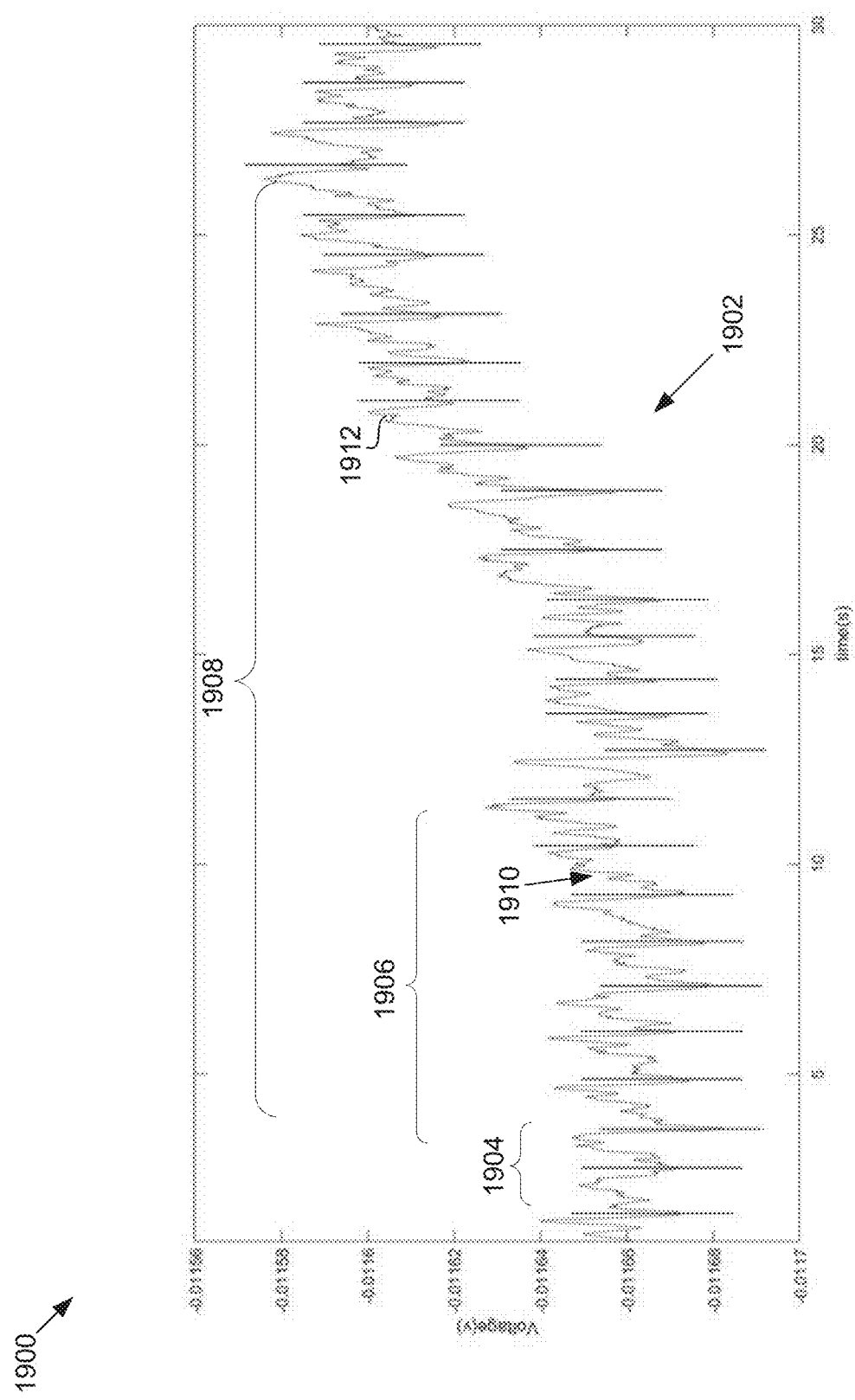
FIG. 19 illustrates a heartbeat waveform as measured by the miniaturized impedance sensor, according to an embodiment.

FIG. 19 illustrates a heartbeat waveform 1900 as measured by a miniaturized impedance sensor such as the miniaturized impedance sensor 400, according to an embodiment. In one example, a structure of a body part of a user, such as a muscular-walled tube, may include a dynamic internal feature which causes a variability in an impedance of the structure. The dynamic internal feature may include a variable volume or material constituency, such as an amount of blood in the muscular-walled tube or a diameter or size of the muscular-walled tube.

The heartbeat waveform 1900 may be used by a processing device to isolate and/or identify a physiological condition, a physiological parameter, and/or a physiological constituent of a user of a wearable device such as the wearable device 100. A biometric impedance measurement 1902 may fluctuate over a variety of timeframes. The timeframes may include a first timeframe 1904, a second timeframe 1906, and a third timeframe 1908. The biometric impedance measurement 1902 may correspond to a change in a volume of blood within a body part adjacent to the miniaturized impedance sensor. The body part may include a muscular-walled tube for carrying blood, such as a vein or artery. The biometric impedance measurement 1902 may represented as a change in voltage. As the volume of blood within the body part increases, the voltage measured by the miniaturized impedance sensor may increase. As the volume of blood within the body part decreases, the voltage measured by the miniaturized impedance sensor may decrease. A shape of the heartbeat waveform 1900 may include noise 1910. The noise may correspond to one or more other physiological and/or non-physiological factors such as feedback and/or electronic noise within the miniaturized impedance sensor, electrical signals within the body not generated by the miniaturized impedance sensor, and so forth.

Voltage changes within the various timeframes may correspond in time to changes in physiological features that may effect a volume of blood in the user's vein and/or artery. For example, a short timeframe such as the first timeframe 1904 may correspond to the user's heartbeat and/or breathing. Viewing a shorter timeframe may illuminate one or more heart conditions, such as an effectiveness of a mitral valve of the heart as indicated by a dicrotic notch 1912. A longer timeframe such as the second timeframe 1906 may correspond to a sympathetic response of the user or a posture change of the user. One such sympathetic response may include vasoconstriction due to the user being exposed to cold. One such posture change may include the user lowering the body part relative to the user' heart and/or raising the body part relative to the user's heart. The longer timeframe may correspond to the user performing a Valsalva maneuver, such as when lifting weights. A yet longer timeframe such as the third timeframe 1908 and timeframes longer than the third timeframe 1908 may provide indication of a peripheral disease which may effect volumetric flow of blood and/or an amount of current impeded by the blood. For example, increased levels of blood glucose may decrease the impedance of the blood. Sustained levels of decreased impedance may indicate glucose is not being removed from the blood sufficiently. Excess blood glucose may lead to one or more of a number of health conditions, such as blood vessel damage, organ damage, and so forth.

During the first timeframe 1904, the voltage of the measurement may vary by as much as $3\times10^{-5}$ Volts (V) over approximately 3 seconds. A local maximum within the first timeframe 1904 may correspond to the user's heart contracting, forcing blood out of the heart and through the artery and/or vein. A local minimum within the first timeframe 1904 may correspond to the user's heart expanding and drawing blood from the artery and/or vein. During the second timeframe 1906, the voltage of the measurement may vary by as much as $6\times10^{-5}$ V over approximately 10 seconds. The second timeframe 1906 may correspond to a physiological condition, physiological parameter, and/or physiological constituent closely related to the user's heartbeat. A relative increase of the local maximums and/or the local minimums may correspond to, for example, vasodilation. During the third timeframe 1908, the voltage of the measurement may vary by as much as $1\times10^{-4}$ V over approximately 25 seconds. The third timeframe 1908 may correspond to a physiological condition, physiological parameter, and/or physiological constituent unrelated to the user's heartbeat, such as a hydration condition of the user. Longer timeframes may correspond to more a static physiological condition, physiological parameter, and/or physiological constituent of the user, such as body fat percentage and/or bone density.

The biometric impedance measurement 1902 may be passed to a processing device which may perform a function on the heartbeat waveform 1900 to separate constituent waveforms of the heartbeat waveform 1900. The function may include, for example, a regression analysis. The processing device may identify a timeframe associated with an individual constituent waveform to identify a type of physiological condition, physiological parameter, and/or physiological constituent to which the constituent waveform corresponds. In an embodiment, the processing device may select constituent waveforms on a timeframe corresponding to the user's heartbeat to determine physiological constituent of the user's blood. In an embodiment, the processing device may select constituent waveforms on a timeframe much larger than a timeframe of the user's heartbeat to determine a physiological condition of the user's skin. In an embodiment, the processing device may select a constituent waveform based on a shape of succeeding crests and valleys. The shape of succeeding crests and valleys may correspond to one or more of a diastole, a systole, and a dichroic notch of the user's heartbeat.

In an embodiment, the wearable device 100 may include a=the band 106, the user interface 104, the miniaturized impedance sensor 400, the processing device 102, and the electrical circuit 108. The band 106 may be configured to extend at least partially around the body part 320 of a user, the body part 320 comprising the dermal layer and the muscular-walled tube 322 or 324 within the body part 320. The user interface 104 may be coupled to the band 106. The electrical circuit 108 may be embedded in the band 106. The electrical circuit 108 may interconnect the user interface 104, the processing device 102, or the miniaturized impedance sensor 400.

The miniaturized impedance sensor 400 may be integrated into the band 106 and positioned in the band 106 to be pressed against the dermal layer and straddle the muscular-walled tube 322 or 324 when the user wears the band 106. The miniaturized impedance sensor 400 may include a first set of the miniaturized electrodes 412 and a second set of the miniaturized electrodes 412. The first set of the miniaturized electrodes 412 may include a first miniaturized electrode 412 and a second miniaturized electrode 412. The second set of the miniaturized electrodes 412 may include a third miniaturized electrode 412 and a fourth miniaturized electrode 412. The first miniaturized electrode 412 and the second miniaturized electrode 412 may straddle the third miniaturized electrode 412 and the fourth miniaturized electrode 412. The first set of the miniaturized electrodes 412 may be configured to generate a signal, the signal having a property that is variable based on a variable state of the muscular-walled tube 322 or 324. The second set of the miniaturized electrodes 412 may be configured to measure the property of the signal.

The processing device 102 may be configured to interrogate the muscular-walled tube 322 or 324 via the miniaturized impedance sensor 400. The processing device 102 may be configured to generate the signal by the first set of the miniaturized electrodes 412. The signal may be configured to pass through the muscular-walled tube 322 or 324 as the user wears the band. The processing device 102 may be configured to take a set of measurements, by the second set of the miniaturized electrodes 412, over a period of time as the user wears the band 106. The processing device 102 may be configured to determine the heartbeat waveform 1900 of the user based on the set of measurements. The processing device 102 may be configured to determine a change in a condition of the user, the body part 320, or the muscular-walled tube 322 or 324 based on a change in the heartbeat waveform 1900.

In one example of the embodiment, the heartbeat waveform 1900 may include a local peak corresponding to a cardiac diastole as a heart of the user fills with blood. The heartbeat waveform 1900 may include a local valley corresponding to a ventricular systole as the blood is forced from the heart into the muscular-walled tube. The heartbeat waveform 1900 may include the dicrotic notch 1912 between the local valley and the local peak corresponding to a closure of the backflow valve of the heart.

In another example of the embodiment, the heartbeat waveform 1900 may include changes in the heartbeat waveform 1900 over the first timeframe 1904 and the second timeframe 1906. The first timeframe 1904 may correspond to a change in a first condition of the muscular-walled tube 322 or 324 or material within the muscular-walled tube 322 or 324. The second timeframe 1906 may be longer than the first timeframe 1904. The second timeframe 1906 may correspond to a change in a second condition of the muscular-walled tube 322 or 324 or material within the muscular-walled tube 322 or 324. The first condition or the second condition may include a change in shape, a change in volume, or a change in material content of the muscular-walled tube 322 or 324 or the material within the muscular-walled tube 322 or 324.

In an example, the property of the signal may include an electromagnetic property of the signal. The variable state of the muscular-walled tube 322 or 324 may include a change in a shape, a volume, or a material content of the muscular-walled tube 322 or 324 over a period of time. The processing device 102 may be configured to filter noise out of the signal based on the heartbeat waveform 1900. The noise may include changes in the signal over a noise timeframe. The heartbeat waveform 1900 may include a heartbeat timeframe ranging from one quarter of a second to two seconds. The noise timeframe may be less than the heartbeat timeframe.

In another example, the change in the condition may include a change in a volume of blood within the muscular-walled tube 322 or 324. The change in the volume may be caused by a pressure wave within the muscular-walled tube 322 or 324. The pressure wave within the muscular-walled tube 322 or 324 may be caused by the heart of the user pumping the blood through the muscular-walled tube 322 or 324. The change in the volume of the blood may change an impedance measured by the miniaturized impedance sensor 400 as the user wears the band 106. The change in the condition may include a change in an amount of glucose within the muscular-walled tube 322 or 324. The change in the amount of glucose may change an impedance measured by the miniaturized impedance sensor 400 as the user wears the band 106.

In an embodiment, the miniaturized impedance sensor 400 may be electronically coupled to the processing device 102. The miniaturized impedance sensor 400 may be coupled to a dermal layer of the body part 320. The body part 320 may include a subdermal feature such as bone, ligament, or the muscular-walled tube 322 or 324. The miniaturized impedance sensor 400 may include a first miniaturized electrode 412, a second miniaturized electrode 412, a third miniaturized electrode 412, and a fourth miniaturized electrode 412. The first miniaturized electrode 412 and the second miniaturized electrode 412 may straddle the third miniaturized electrode 412 and the fourth miniaturized electrode 412. The first miniaturized electrode 412 and the second miniaturized electrode 412 may be configured to generate a signal. The third miniaturized electrode 412 and the fourth miniaturized electrode 412 may be configured to measure the signal.

The processing device 102 may be configured to generate the signal by the first miniaturized electrode 412 and the second miniaturized electrode 412. The signal may pass through the subdermal feature. The processing device 102 may be configured to measure the signal by the third miniaturized electrode 412 and the fourth miniaturized electrode 412. The processing device 102 may be configured to determine an impedance of the subdermal feature based on the measurement of the signal. The processing device 102 may be configured to map a change in the impedance from a measurement taken at a previous time. The processing device 102 may be configured to generate the heartbeat waveform 1900 based on the change in the impedance.

In an example of the embodiment, the measurement may include a first indicator corresponding to a first condition and a second indicator corresponding to a second condition. The first indicator may be represented within the second indicator in the heartbeat waveform 1900. The second indicator may be discernable from the first indicator by performing a regression analysis on the heartbeat waveform 1900. The subdermal feature may include the muscular-walled tube 322 or 324 carrying blood. The first indicator may correspond to a pressure wave radiating through the muscular-walled tube 322 or 324. The second indicator may correspond to a constriction or a dilation of the muscular-walled tube 322 or 324. The miniaturized impedance sensor 400 may measure the pressure wave and the constriction or the dilation as the miniaturized impedance sensor 400 is coupled to the body part. The processing device 102 may be configured to perform the regression analysis by averaging peaks and valleys of the heartbeat waveform 1900 corresponding to the first indicator. The second indicator may correspond to a change across a plurality of averages of the peaks and the valleys.

In another example, the change in the impedance may correspond to a change in a volume of the subdermal feature. The change in the volume may cause an increase in the impedance. A change in a constituent material of the subdermal feature may cause an increase in the impedance or a decrease in the impedance. The change in the constituent material may occur over a longer timeframe than the change in the volume. The processing device may be configured to identify the change in the volume from the change in the constituent material based on determining whether the change in the impedance occurs over the longer time frame.

In yet another embodiment, the miniaturized impedance sensor 400 may be configured to take a measurement from the muscular-walled tube 322 or 324 within a body part 320 of the user. The miniaturized impedance sensor 400 may include a first set of the miniaturized electrodes 412 and second set of miniaturized electrodes 412. The first set of the miniaturized electrodes 412 may be configured to generate a signal within the muscular-walled tube 322 or 324. The second set of the miniaturized electrodes 412 may be configured to measure the signal, the measurement taken from the muscular-walled tube 322 or 324. The embodiment may include the processing device 102, which may be programmed to interrogate the muscular-walled tube 322 or 324 via the miniaturized impedance sensor 400. The processing device 102 may be configured to generate the signal by the first set of the miniaturized electrodes 412. The processing device 102 may be configured to measure the signal by the second set of miniaturized electrodes 412. The processing device 102 may be configured to generate the heartbeat waveform 1900 based on the measurement of the signal by the second set of the miniaturized electrodes 412. The processing device 102 may be configured to determine a condition of the user based on the heartbeat waveform 1900.

In one example of the embodiment, the processing device 102 may be configured to correlate a change in the measurement with a change in: a posture of the body part; a sympathetic response of the body part; or a Val Salva maneuver by the user. The change in the measurement may occur over a timeframe of less than one minute. The processing device 102 may be configured to correlate a change in the measurement with a change in glucose in the muscular-walled tube or a change in a hydration condition of the user.

In another example, the heartbeat waveform 1900 may include a first pattern indicating a first condition of the user and a second pattern indicating a second condition of the user. The first pattern may be represented within the second pattern in the heartbeat waveform 1900. The processing device 102 may be configured to take a first set of measurements using the miniaturized impedance sensor 400. The processing device 102 may be configured to generate the heartbeat waveform 1900 based on the first set of measurements. The processing device 102 may be configured to take a second set of measurements using a second sensor such as the first sensor 112. The second set of measurements may form a second waveform which may include the second pattern. The processing device 102 may be configured to isolate the first pattern from the heartbeat waveform 1900 by comparing the heartbeat waveform 1900 to the second waveform to identify the second pattern in the heartbeat waveform 1900.

In yet another example, the processing device 102 may be configured to index a change in the measurement to a passage of time. The passage of time may correspond to changes in two conditions of the user. The processing device 102 may be configured to filter noise from the heartbeat waveform. The noise may include a change in the heartbeat waveform 1900 over a first timeframe. The first timeframe may be shorter than a minimum timeframe between a local valley and a local peak of the heartbeat waveform 1900 corresponding to a heartbeat of the user.

FIGS. 20-24 depict various methods for making, manufacturing, and/or preparing a miniaturized impedance sensor such as the miniaturized impedance sensor 400, according to various embodiments. The steps of the methods are illustrated in the figures as blocks. Although an order may be inferred from the illustrations and/or from the accompanying descriptions, the order is not intended to limit the scope of the methods to the particular orders of the steps that may be inferred. Various steps of the methods may be done out of order, in a different order, and/or may be omitted without departing from the substance and/or spirit of this disclosure. For example, two blocks may be described in a particular sequence in this disclosure but may be performed in an opposite sequence without altering the method in any substantial and/or material way.

Methods and/or techniques described throughout this disclosure may generally refer to "depositing," "growing," and/or "patterning." As used throughout this disclosure, "deposit" and/or "grow," including semantic and/or stemmed variations of "deposit" and/or "grow," may refer to any of a variety of processes used for layering material. In one embodiment, a first layer may be deposited on a second layer by forming the first layer and then placing the first layer on the second layer. In another embodiment, the first layer may be deposited on the second layer by a thin film deposition technique. The thin film deposition technique may include physical vapor deposition (PVD), cathodic arc deposition, electron beam PVD, electron beam evaporation, chemical vapor deposition (CVD), atomic layer deposition, close-space sublimation, sputter deposition, pulsed electron deposition, sublimation sandwich deposition, and so forth. In an embodiment, the first layer may be deposited on the second layer by a thin film growth mode such as Frank-van de Merwe growth, Stranski-Krastanov growth, Volmer-Weber growth, epitaxial growth, and/or molecular beam epitaxy. In an embodiment, the first layer may be deposited on the second layer by a sputtering method such as diode sputtering, radio frequency sputtering, magnetron sputtering, and/or reactive sputtering.

As used throughout this disclosure, "pattern," including semantic and/or stemmed variations of "pattern," may refer to a structure and/or order of sections of an individual layer. A patterned layer may have two or more sections and/or regions of various thickness and/or shape. For example, a first section of the layer may have a first thickness, and a section of the layer may have a second thickness that may be greater than or less than the first thickness. A first shape of the first section of the layer may be the same as or different than a second shape of the second section of the layer. In an embodiment, a pattern of the layer may be geometric, tiled, spiraled, meandering, waving, foamy, cracked, symmetric, asymmetric, reflective, chaotic, fractal, and so forth.

As used throughout this disclosure, "coat," including semantic and/or stemmed variations of "coat," may refer to any of a variety of processes for coating an object with a thin film. The thin film may be of uniform thickness or variable thickness. The thickness may vary from less than 1 micron to 5 mm. The processes may include spin coating, spray coating, dip coating, roller coating, and/or sputtering.

FIG. 20 illustrates a method 2000 of preparing a miniaturized impedance sensor, according to an embodiment. The method 2000 may include patterning a conductive layer, such as the conductive layer 406, on a sensor substrate (block 2004). The conductive layer may be patterned on the sensor substrate using a deposition technique such as PVD.

In various embodiments the deposition technique may include sputtering and/or evaporation. The pattern may include one or more of the patterns described and/or illustrated herein. The sensor substrate may include a growth substrate such as the growth substrate 402 and a base insulating layer such as the first insulating layer 404. In various embodiments where the conductive layer may include nickel and the sensor substrate may include silicon, the base insulating layer may prevent formation of nickel silicide. The method 2000 may include depositing a medial insulating layer, such as the second insulating layer 408, on the conductive layer (block 2006). In one embodiment, the medial insulating layer may be deposited over positive and negative regions of the conductive layer. In another embodiment, the medial insulating layer may be patterned. The pattern of the medial insulating layer may align positive regions of medial insulating layer material on positive regions of the conductive layer. In one example, a first insulating layer may be disposed on the growth substrate. The first insulating layer may prevent molecular reaction of a deposition material with the growth substrate during a PVD process or a CVD process. In one example, the growth substrate may withstand infiltration at a threshold temperature for a physical vapor deposition (PVD) process or a chemical vapor deposition (CVD) process.

The method 2000 may include patterning a catalyst layer, such as the catalyst layer 410, on the medial insulating layer (block 2008). The catalyst layer may be patterned similarly to the medial insulating layer so that positive regions of the catalyst layer may be aligned on positive regions of medial insulating layer and/or positive regions of conductive layer. The catalyst layer may be deposited on the medial insulating layer by sputtering, evaporation, and so forth. The method 2000 may include growing miniaturized electrodes, such as the miniaturized electrodes 412, on the catalyst layer (block 2010). In one example, the second insulating layer 408 may be rendered conductive by an environmental condition for growth of the miniaturized electrode on the catalyst layer. The medial insulating layer may be deposited via sputtering, evaporation, and so forth. The environmental condition that renders the second insulating layer may include a temperature, a pressure, or a time frame of the PVD process or the CVD process.

In various embodiments, the miniaturized electrodes may be grown via chemical vapor deposition (CVD). The method 2000 may include infiltrating the miniaturized electrodes with a bolstering material, such as the bolstering material described regarding FIGS. 4A-C (block 2012). The miniaturized electrodes may be infiltrated with the bolstering material via CVD. The method 2000 may include applying a hydrophilic treatment to the miniaturized electrodes to render the miniaturized electrodes hydrophilic (block 2014). For example, in one embodiment, the miniaturized electrodes may include carbon-infiltrated CNTs. Applying the hydrophilic treatment may include exposing the carbon-infiltrated CNTs to Ozone. The CNTs may be placed in a tube having a 6.5 cm$^2$ cross-section and ozone may be flowed over the CNTs at room temperature for 30 minutes at a rate of 4.4 grams/hour.

The method 2000 may include coating the growth substrate, the conductive layer, the medial insulating layer, the catalyst layer, and/or the miniaturized electrodes with an interstitial filler such as the interstitial filler 414 (block 2016). For example, the interstitial filler may include polyimide. The growth substrate, the conductive layer, the medial insulating layer, the catalyst layer, and/or the miniaturized electrodes may be coated with the polyimide by spinning and/or spraying the polyimide over the layers. The method 2000 may include removing a portion of the interstitial filler to expose top portions of the miniaturized electrodes (block 2018). For example, the polyimide may be subjected to photo exposure to a partial depth of the polyimide. The photo exposure may degrade the exposed polyimide. The degraded polyimide may be washed away in a chemical bath to expose the top portions of the miniaturized electrodes. In another example, a portion of the interstitial filler may be removed by polishing the interstitial filler. The method 2000 may include applying a treatment to the interstitial filler to render the interstitial filler insolvent and/or solvent resistant (block 2020). For example, the polyimide may be cross-linked by heating the polyimide or via UV exposer of the polyimide. The method 2000 may include inducing reflow of the interstitial filler (block 2022). For example, the coated layers may be placed in a heating chamber. The temperature of the heating chamber may be slowly increased to a cross-linking temperature of the interstitial filler, such as over 1 minute, 2 minutes, 5 minutes, and/or 10 minutes. The increasing temperature may melt the interstitial filler, thereby inducing reflow of the interstitial filler. The reflow may cause portions of the interstitial filler to slope up the miniaturized electrodes, creating wells, such as the wells 414a and 414b, in the interstitial filler between neighboring miniaturized electrodes.

The method 2000 may include scoring and/or partially dicing through one or more layers, including the sensor substrate, the medial insulating layer, and/or the interstitial filler (block 2024). For example, the sensor substrate may include a silicon wafer having a layer of alumina. A plurality of miniaturized impedance sensors may be formed on and/or incorporating the sensor substrate, according to an embodiment. The sensor substrate, the medial insulating layer, and/or the interstitial filler may be common among the plurality of miniaturized impedance sensors. The miniaturized impedance sensors may be separated from each other by scoring and/or partially dicing the one or more layers to separate the miniaturized impedance sensors. The scoring may be performed from the substrate-side of the miniaturized impedance sensor. The scoring and/or dicing may be aligned with areas of the base insulating material. This may prevent accidental cutting of the miniaturized electrodes. In various embodiments, the sensor substrate may be diced to separate the miniaturized impedance sensors. In various embodiments, the sensor substrate may be scored. The scoring may increase a surface area which may be exposed to allow for quicker and/or easier release of the miniaturized impedance sensor from the sensor substrate. In one example, the substrate may be diced to segregate subsets of an array of miniaturized electrodes while the interstitial filler between the subsets remains intact, to allow the miniaturized impedance sensor to flex between the subsets.

The method 2000 may include releasing the sensor substrate from the other layers (block 2026). For example, the miniaturized impedance sensor, including the sensor substrate and the other layers deposited thereon, may be submersed in a chemical bath such as potassium hydroxide (KOH). The KOH may etch the base insulating layer to release the miniaturized electrodes and conductive layer from the sensor substrate. In an embodiment, after releasing the sensor substrate, some of the base insulating layer may remain attached to one or more of the conductive layer, the medial insulating layer, the catalyst layer, the miniaturized electrodes, and/or the interstitial filler. Accordingly, the method 2000 may include etching the layers to remove the base insulating layer and/or a process byproduct (block 2028). For example, a layer of alumina may remain after the silicon wafer is released. The alumina may be removed by plasma etching and/or wet etching such as a chemical bath. In another example, various of the processes the conductive layer may be subjected to during the process of preparing the miniaturized impedance sensor may expose the conductive layer to high heat and/or chemicals which may catalyze the oxidation of the conductive, according to an embodiment. The oxidized nickel may be removed by plasma etching and/or solder flux. In an embodiment, the remaining layers, including the conductive layer, the medial insulating layer, the catalyst layer, the miniaturized electrodes, and/or the interstitial filler may form an embodiment of a miniaturized impedance sensor, such as the miniaturized impedance sensor 400.

In various embodiments, the miniaturized impedance sensor may be implemented in one or more of a variety of ways as described and/or illustrated throughout this disclosure. The method 2000 may include placing the miniaturized impedance sensor onto a device substrate, such as the substrate 816, for incorporating the miniaturized impedance sensor into a wearable device such as the wearable device 100 (block 2030). The device substrate may include a flexible substrate. The substrate may in an embodiment, include polyimide. In an embodiment, the substrate may include a pattern of electrical leads. The pattern may match a pattern of the conductive layer. The miniaturized impedance sensor may be adhered to the device substrate by applying an adhesive to the device substrate and/or a conductive layer side of the miniaturized impedance sensor and then placing the miniaturized impedance sensor and the device substrate together. The adhesive may include a solder paste, according to an embodiment. In various embodiments, the miniaturized impedance sensor may be adhered to the device substrate by applying a conductive epoxy and/or heat activated conductive adhesive. The device substrate may include patterned leads. The leads may be patterned on the device substrate to match the pattern of the conductive layer. The miniaturized impedance sensor and the device substrate may be joined so that the conductive layer contacts the patterned leads. The adhesive may secure the miniaturized impedance sensor and the device substrate together. Securing the miniaturized impedance sensor and the device substrate with the adhesive may include activating the adhesive. In an embodiment, the adhesive may include solder and activating the adhesive may include heating the solder to induce reflow. In various embodiments, a plurality of miniaturized impedance sensors may be joined to a single sheet of device substrate. Accordingly, the method 2000 may include cutting the device substrate to separate the miniaturized impedance sensors (block 2032).

Figure 20A:
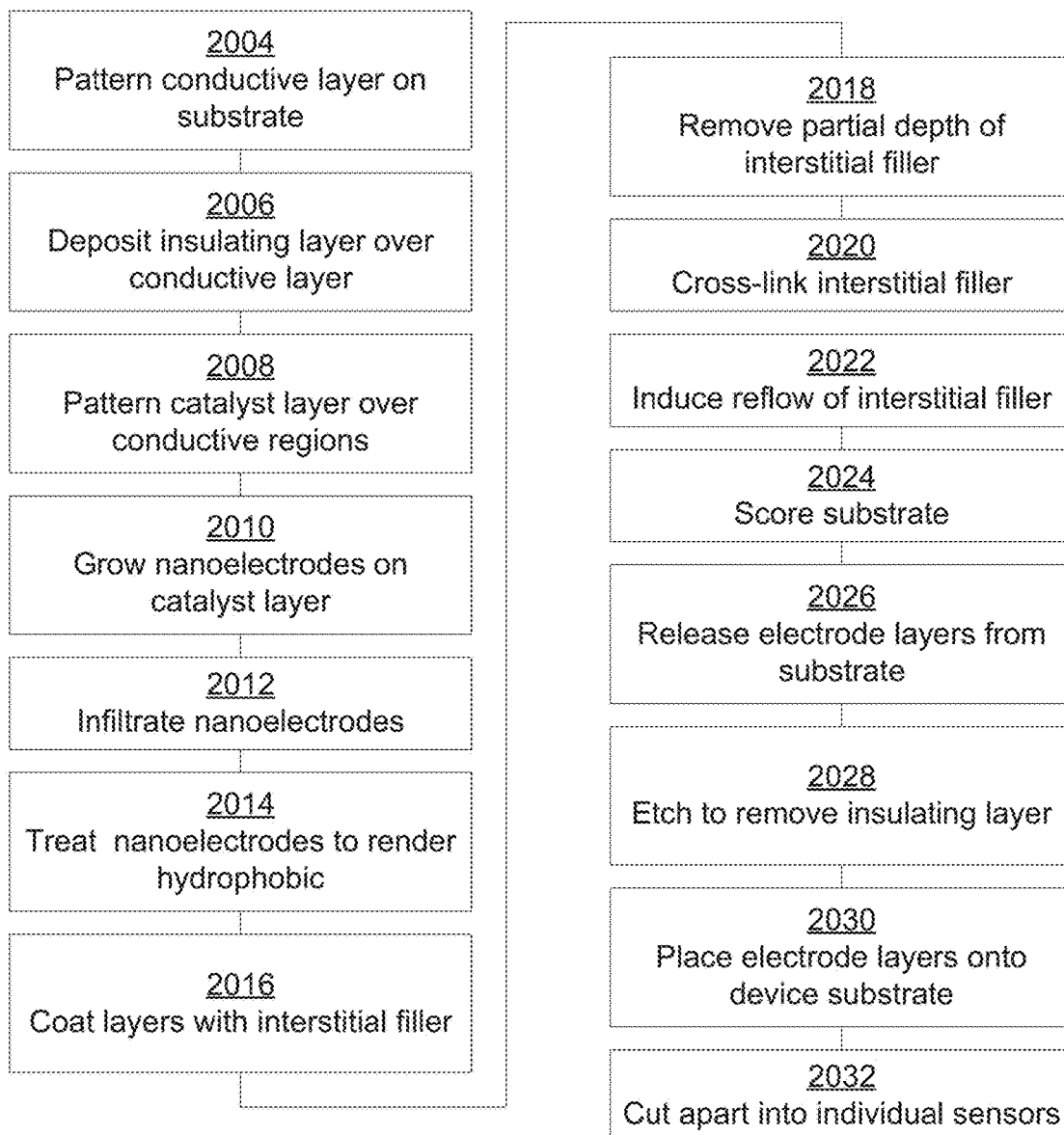
FIG. 20A illustrates a method of preparing the miniaturized impedance sensor, according to an embodiment.
Figure 20B:
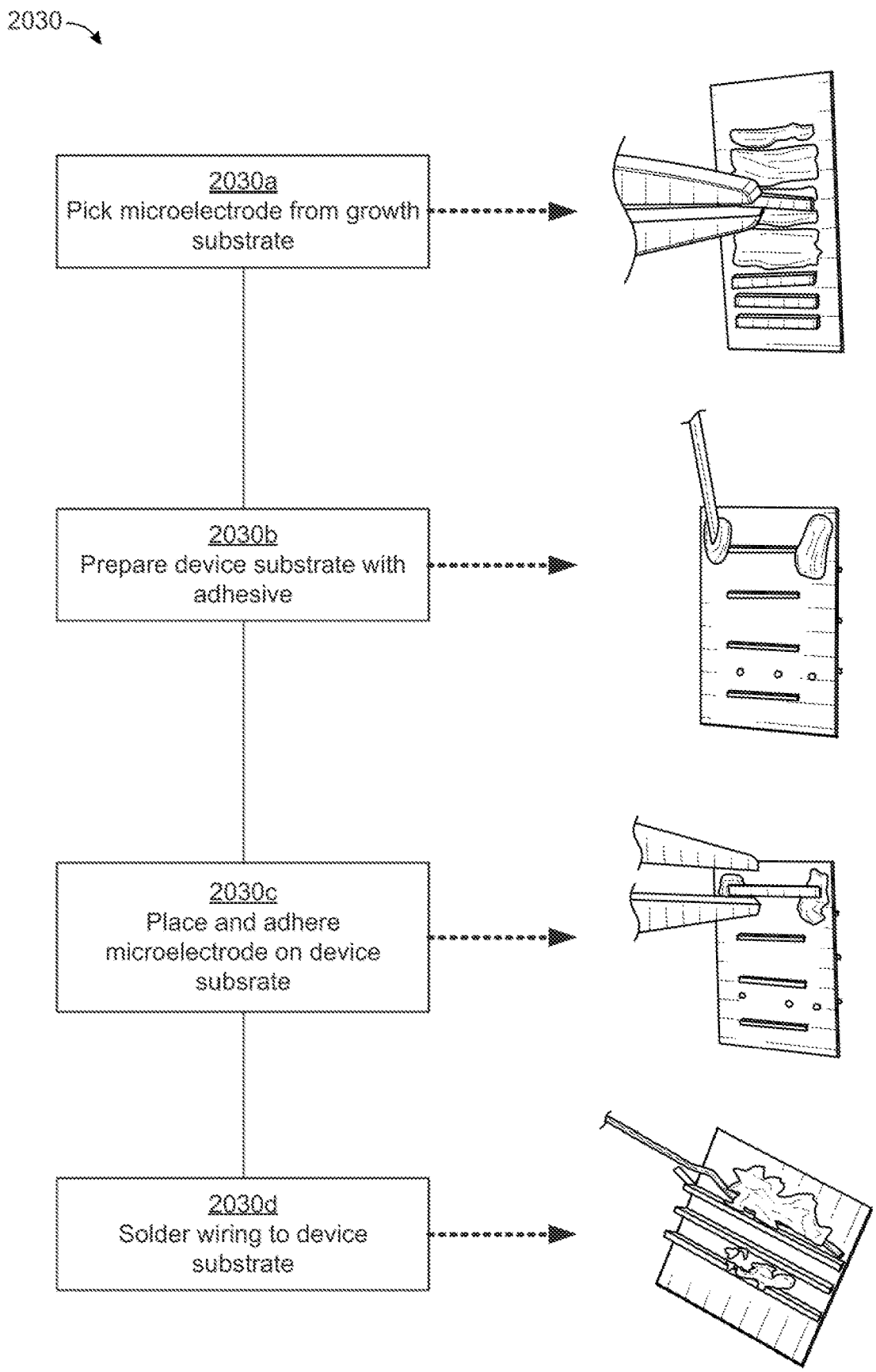
FIG. 20B illustrates a method of placing miniaturized electrodes on a device substrate, according to an embodiment.

FIG. 20B illustrates a sub-method of block 2030 in the method 2000 of preparing the nano impedance sensor, including placing miniaturized electrodes on a device substrate, according to an embodiment. Some of the blocks in FIG. 20B are the same as or similar to some of the blocks in FIGS. 1-20A as noted by same and/or similar reference characters, unless expressly described otherwise. The sub-method may include picking a miniaturized electrode from a substrate (block 2030*a*). The miniaturized electrode may have been grown on the substrate such that the substrate is a growth substrate. The miniaturized electrode may be picked from the substrate by tweezers. The sub-method may include preparing a device substrate with an adhesive (block 2030*b*). The device substrate may include a surface to which the miniaturized electrode is mounted. Adhesive may be applied to the surface. The surface may include one or more vias. The vias may include slots passing through the device substrate. The slots may enable electrical connection of a wire from an underside of the device substrate to the miniaturized electrode.

The sub-method may include placing the miniaturized electrode on the device substrate over one of the vias and on the adhesive (block 2030*c*). The adhesive may adhere the miniaturized electrode to the device substrate. In an embodiment, the adhesive may be placed to avoid seeping into the vias, leaving the vias clear for electrical connection. The sub-method may include placing a wire along a back side of the device substrate aligned with the via the miniaturized electrode is aligned over and soldering the wire to the device substrate and/or the miniaturized electrode (block 2030*d*). In various embodiments, the device substrate may include a loop over the via along the back side of the device substrate, the loop positioned to receive the wire and hold the wire in place as the wire is soldered to the device substrate and/or the miniaturized electrode.

Figure 21:
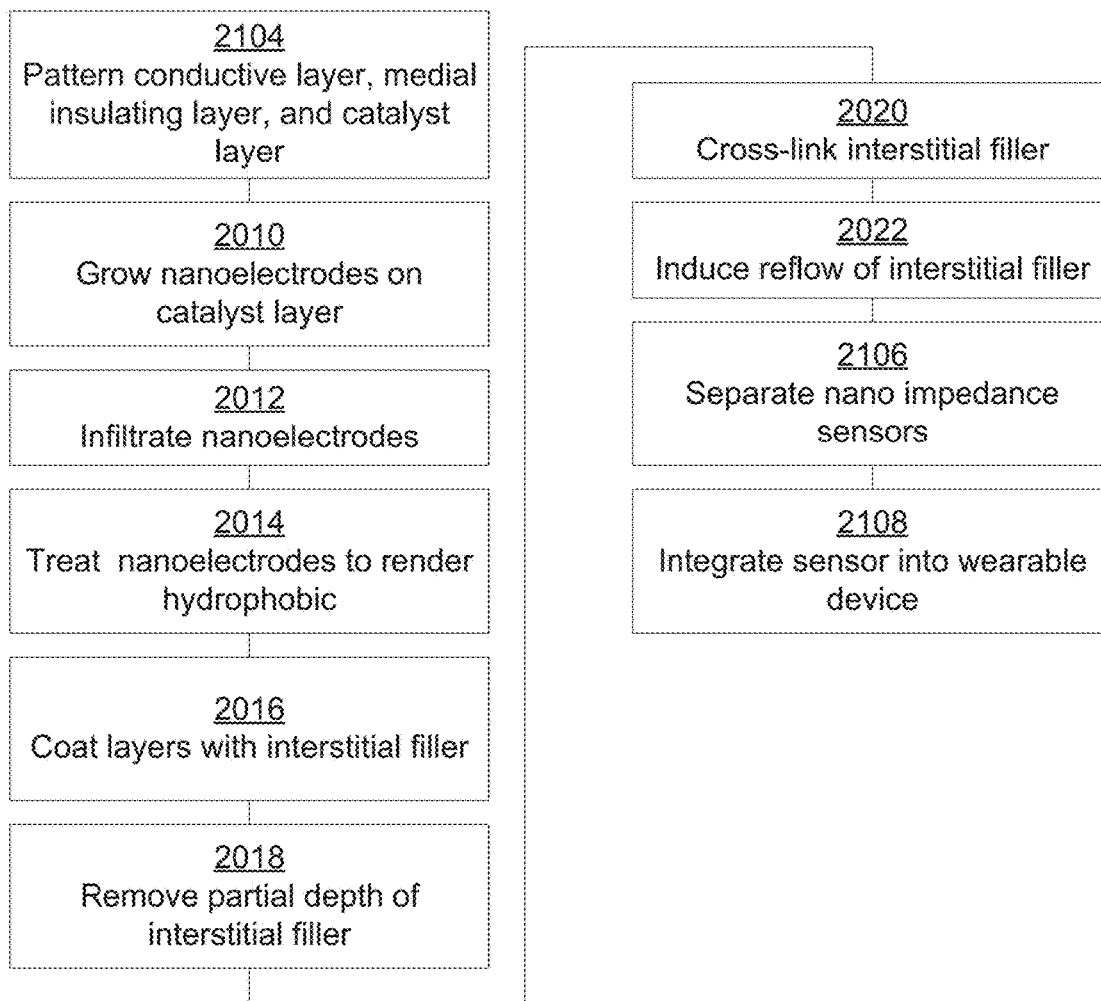
FIG. 21 illustrates a method of preparing the nano impedance similar to the method illustrated in FIG. 20, including a single step for depositing multiple layers, according to an embodiment.

FIG. 21 illustrates a method 2100 of preparing the nano impedance similar to the method illustrated in FIG. 20A, including a single step for depositing multiple layers, according to an embodiment. Some of the blocks in FIG. 21 are the same as or similar to some of the blocks in FIGS. 1-20B as noted by same and/or similar reference characters, unless expressly described otherwise. The method 2100 may include depositing a conductive layer, a medial insulating layer, and a catalyst layer on the sensor substrate via an all-in-one deposition step (block 2104). In an embodiment, the conductive layer, the medial insulating layer, and/or the catalyst layer may be patterned on the sensor by electron beam physical vapor deposition, sputtering deposition, and so forth. The method 2100 may include depositing a medial insulating layer, such as the second insulating layer 408, on the conductive layer (block 2006). The method 2100 may include patterning a catalyst layer, such as the catalyst layer 410, on the medial insulating layer (block 2008). The method 2100 may include growing miniaturized electrodes, such as the miniaturized electrodes 412, on the catalyst layer (block 2010). The method 2100 may include infiltrating the miniaturized electrodes with a bolstering material, such as the bolstering material described regarding FIGS. 4A-C (block 2012). The method 2100 may include applying a hydrophilic treatment to the miniaturized electrodes to render the miniaturized electrodes hydrophilic (block 2014). The method 2100 may include coating the growth substrate, the conductive layer, the medial insulating layer, the catalyst layer, and/or the miniaturized electrodes with an interstitial filler such as the interstitial filler 414 (block 2016). The method 2100 may include removing a portion of the interstitial filler to expose top portions of the miniaturized electrodes (block 2018). The method 2100 may include applying a treatment to the interstitial filler to render the interstitial filler insolvent and/or solvent resistant (block 2020). The method 2100 may include inducing reflow of the interstitial filler (block 2022).

In various embodiments, sensor substrate, the conductive layer, the medial insulating layer, the catalyst layer, the miniaturized electrode, and/or the interstitial filler may form a miniaturized impedance sensor such as the miniaturized impedance sensor 400. In an embodiment, a plurality of miniaturized impedance sensors may be formed together on the same sensor substrate. Accordingly, the method 2100 may include scoring and/or cutting through one or more layers of the plurality of miniaturized impedance sensors (block 2106). The scoring and/or cutting may be performed, in one embodiment, with a silicon wafer dicing saw. One or more individual miniaturized impedance sensors may be broken and/or cut away from the plurality of miniaturized impedance sensors. The method 2100 may include integrating the individual miniaturized impedance sensor into a wearable device such as the wearable device 100. In an embodiment, a conductive material may be added to the miniaturized impedance sensor electrically coupled to the conductive layer. The conductive material may be electrically coupled to various electronics of the wearable device, such as on a circuit board via an electrical trace. The electronics may be the same as or similar to the electronic components 1206. The electronics may be interconnected via the circuit board. The electrical trace may be the same as or similar to the electrical trace 820. In one embodiment, the circuit board may be a flexible band of the wearable device, such as the band 106. The electrical trace, the electronics, and/or the miniaturized impedance sensor may be embedded in the band.

In addition or alternative to the blocks show in FIG. 21, the method 2100 may include: patterning a thin film conductive layer on a sensor substrate, where the sensor substrate includes a base insulating layer that may prevent infiltration of a material into the sensor substrate and the thin film conductive layer may be deposited on the base insulating layer; depositing a thin film medial insulating layer on the thin film conductive layer; patterning a thin film catalyst layer on the thin film medial insulating layer to form a catalyst layer pattern, the catalyst layer pattern being aligned with a conductive layer pattern; growing a nanotube miniaturized electrode on the thin film catalyst layer, the nanotube miniaturized electrode being aligned with a section of the catalyst layer pattern; infiltrating the nanotube miniaturized electrode with a bolstering material to bolster nanotubes of the nanotube miniaturized electrode; applying a hydrophilic treatment to render the nanotube miniaturized electrode hydrophilic; coating the nanotube miniaturized electrode with an interstitial filler to electrically insulate the nanotube miniaturized electrode and bolster the nanotube miniaturized electrode; removing a top portion of the interstitial filler to expose a top surface of the nanotube miniaturized electrode; cross-linking the interstitial filler to render the interstitial filler solvent-resistant; inducing reflow of the interstitial filler by increasing a temperature of the interstitial filler from a first temperature at which the interstitial filler may be solid to a second temperature for melting point of the interstitial filler, the temperature increasing to the melting point in 1 minute to 2 minutes, 2 minutes to 5 minutes, or 5 minutes to 10 minutes; scoring or dicing the sensor substrate, the thin film medial insulating layer, or the interstitial filler; releasing the sensor substrate or the base insulating layer from one or more sensor layers, wherein the one or more sensor layers includes the thin film conductive layer, the thin film medial insulating layer, the thin film catalyst layer, the nanotube miniaturized electrode, or the interstitial filler; and/or integrating the one or more sensor layers into a band of a wearable device, wherein the one or more sensor layers form a miniaturized impedance sensor.

In another example, the catalyst layer pattern may include regions of catalyst material interspersed with catalyst layer voids between the regions of catalyst material. In another example, the conductive layer pattern may include regions of conductive material interspersed with conductive layer voids between the regions of conductive material. In another example, the catalyst layer pattern may be aligned with the conductive layer pattern such that the regions of catalyst layer material are stacked on the regions of conductive layer material. In another example, cross-linking the interstitial filler may include exposing the interstitial filler to high-energy light to render the interstitial filler insolvent. In another example, releasing the sensor substrate may include submersing the sensor substrate, the base insulating layer, or the sensor layers in a chemical bath and/or plasma-etching the base insulating layer.

In another example, the band may extend at least partially around a body part of a user; and the sensor layers are positioned in the band to be adjacent to a section of the body part adjacent to a blood vessel within the body part as the user wears the band.

In another example, the nanotube miniaturized electrode may include a forest of carbon nanotubes, wherein the forest of carbon nanotubes may include a bundle of carbon nanotubes aligned approximately parallel to each other. In another example, the bundle of carbon nanotubes may fill approximately 0.1 percent to 10 percent of a volume of the forest of carbon nanotubes. In another example, the bolstering material may include carbon molecules filling approximately percent to 95 percent of the volume of the forest of carbon nanotubes. In another example, the thin film conductive layer may include nickel, the base insulating layer or the thin film medial insulating layer may include alumina, the sensor substrate may include silicon, the thin film catalyst layer may include iron, the bolstering material may include carbon, and/or the interstitial filler may include polyimide. In another example, patterning the thin film conductive layer, depositing the thin film medial insulating layer, patterning the thin film catalyst layer, and/or growing the nanotube miniaturized electrode may include physical vapor deposition or chemical vapor deposition.

In addition or alternative to the blocks show in FIG. 21, the method 2100 may include: patterning a conductive material on a substrate; depositing a medial insulating material on the conductive material; patterning a nanotube growth catalyst material on the medial insulating material, where a catalyst pattern may be aligned with a conductor pattern formed of the conductive material; growing a miniaturized electrode on the nanotube growth catalyst material, where the miniaturized electrode may be aligned with a section of the catalyst pattern; applying a hydrophilic treatment, the hydrophilic treatment may render the miniaturized electrode hydrophilic; coating the miniaturized electrode with an interstitial filler, wherein a top surface of the miniaturized electrode remains exposed from the interstitial filler; cross-linking the interstitial filler to render the interstitial filler solvent-resistant; and/or scoring or dicing the substrate or the medial insulating material, where the substrate, the conductive material, the medial insulating material, the nanotube growth catalyst material, the miniaturized electrode, and/or the interstitial filler comprise a miniaturized impedance sensor.

In another example, the method 2100 may include integrating the miniaturized impedance sensor into a wearable device. The integrating may include attaching the miniaturized impedance sensor to a flexible circuit board; and/or overmolding the miniaturized impedance sensor and the flexible circuit board to form a flexible band, where a top surface of the miniaturized electrode may be flush with an inside surface of the flexible band, a top surface of the interstitial filler may be flush with the inside surface, and/or the miniaturized electrode protrudes from the inside surface. In another example, a condition of growing the nanotube miniaturized electrode on the nanotube growth catalyst layer renders the medial insulating material electrically conductive to allow for conduction of electricity between the miniaturized electrode and the conductive material. In another example, the scoring or dicing may be between a first region of the miniaturized impedance sensor and a second region of the miniaturized impedance sensor. The scoring or dicing may render the miniaturized sensor flexible. The interstitial filler may be flexible and interconnects the first region and the second region. The first region and the second region may remain locally non-flexible. In another example, the scoring or dicing may divide the substrate into a first miniaturized impedance sensor and/or a second miniaturized impedance sensor.

In addition or alternative to the blocks show in FIG. 21, the method 2100 may include: patterning a set of miniaturized electrode pillars on a substrate; and/or coating the set of miniaturized electrode pillars with an interstitial filler disposed between the set of miniaturized electrode pillars. The interstitial filler may insulate the set of miniaturized electrode pillars from each other; and/or bolster the set of miniaturized electrode pillars. In another example, patterning the set of miniaturized electrode pillars may include forming polymeric pillars via photolithography. In another example, the method 2100 may include depositing a thin film conductive layer on the polymeric pillars and/or etching the thin film conductive layer between the polymeric pillars to electrically isolate the polymeric pillars from each other. In another example, the set of miniaturized electrode pillars may include bundles of carbon nanotubes grown in forests on the substrate and infiltrated with carbon to bolster the carbon nanotubes within the set of miniaturized electrode pillars. In another example, patterning the set of miniaturized electrode pillars may include printing the miniaturized electrode pillars on the substrate. In another example, a resin for printing the set of miniaturized electrode pillars may include carbon nanotubes mixed into the resin to render the resin conductive.

FIG. 22 illustrates a method 2200 for preparing the miniaturized impedance sensor with polymeric nano structures, according to an embodiment. The method 2200 may include patterning one or more polymeric pillars onto a device substrate (block 2204). In one embodiment, the polymeric pillars may be patterned via photolithography using a thick negative photoresist such as bisphenol-A novolac epoxy (SU-8). The device substrate may include a growth substrate such as the growth substrate 402. The device substrate may include a base insulating layer such as the first insulating layer 404. The device substrate may include patterned leads, such as the conductive layer 406. The conductive layer may be patterned and/or deposited onto the device substrate in a manner similar to that described and/or illustrated regarding block 2004. The device substrate may include polyimide, and/or the conductive layer may be formed of nickel. The polymeric pillar may be patterned directly adjacent to the conductive layer on the same surface of the device substrate on which the conductive layer may be formed. For example, the polymeric pillar may touch the conductive layer. The polymeric pillar may include a photoresist, according to an embodiment. The photoresist may, in an embodiment, be a positive photoresist or a negative photoresist. In an embodiment, the photoresist may include polyimide and/or SU-8.

The method 2200 may include depositing a conductive film on the device substrate, the conductive layer, and/or the polymeric pillar (block 2206). In various embodiments, the film may be deposited via sputtering, evaporation, CVD, and so forth. The conductive film may coat the polymeric pillar and form electrical contact with the conductive layer. The conductive film may be a thin film. The thin film may include carbon, metal, and/or a polymer-CNT composite, according to an embodiment. In an embodiment, the thin film may include doped zinc oxide, tin oxide, and/or indium tin oxide. The thin film may include aluminum-doped zinc oxide, according to an embodiment. A plurality of positive regions of the conductive layer and/or corresponding polymeric pillars may be formed on the device substrate. In an embodiment, the conductive layer and/or polymeric pillars may be formed according to a pattern. Accordingly, the method 2200 may include isolating the thin film-coated polymeric pillar and/or the corresponding positive region of the conductive layer from neighboring polymeric pillars and/or neighboring positive regions of the conductive layer (block 2208). Isolating the polymeric pillars may include etching, laser-cutting, and/or otherwise cutting through the thin film along a region between two neighboring polymeric pillars and/or positive regions of the conductive layer. In an embodiment, the cutting may include a process that etches the thin film faster than the device substrate to prevent over etch and/or weakening of the device substrate.

The method 2200 may include coating the device substrate, the conductive layer, the polymeric pillar, and/or the thin film with an interstitial filler (block 2210). In various embodiments, the coating may be applied via spin casting and/or spraying. In an embodiment with a plurality of neighboring polymeric pillars and/or positive regions of the conductive layer, the interstitial filler may fill space between the neighboring polymeric pillars to provide structural support for the pillars. The interstitial filler may include SU-8, according to an embodiment. The SU-8 may be sprayed onto the device substrate to fill the space between the neighboring polymeric pillars and may be etched, such as via UV exposure, to form a trench between the neighboring polymeric pillars and sidewalls at edges of the device substrate. In an embodiment, the photo exposure may be a partial-depth exposure through the device substrate. The interstitial filler may be applied by spraying the interstitial filler to a height continuous with or above a height of the polymeric pillar then allowing a solvent in the interstitial filler to evaporate, according to an embodiment. As the solvent evaporates, the interstitial filler may shrink to a depth lower than a top portion of the polymeric pillar.

FIG. 23 illustrates a method 2300 of 3D-printing a miniaturized impedance sensor, according to an embodiment. The method 2300 may include mixing CNTs into a resin (block 2304). The resin may, in an embodiment, include a resin for a rapid prototyping and/or 3D printing machine. For example, the resin may include a molding resin, an ultrasonic embossing resin, a filament, stereolithography resin, and so forth. The CNTs may be obtained via a commercial supplier, and/or may be obtained in a powder form. The resin may be heated to a temperature above a melting point of the resin. The CNTs may be removed from the catalyst layer and mixed into the molten resin. In an embodiment, the resin may be cooled and/or formed into a filament. The filament may be spooled for printing by a 3D printing machine. The method 2300 may include printing the resin onto a device substrate (block 2306). The device substrate may include a growth substrate such as the growth substrate 402. The device substrate may include a base insulating layer such as the first insulating layer 404. The device substrate may include patterned leads, such as the conductive layer 406. The conductive layer may be patterned and/or deposited onto the device substrate in a manner similar to that described and/or illustrated regarding block 2004. The device substrate may include polyimide, and/or the conductive layer may be formed of nickel. The printed resin may be formed into a pillar and a plurality of pillars may be printed onto the device substrate, according to an embodiment. The pillar may form electrical contact with the conductive layer. The method 2300 may include coating the pillar with an interstitial filler (block 2308). In an embodiment with a plurality of neighboring pillars, the interstitial filler may fill space between the neighboring pillars to provide structural support for the pillars.

Figure 24:
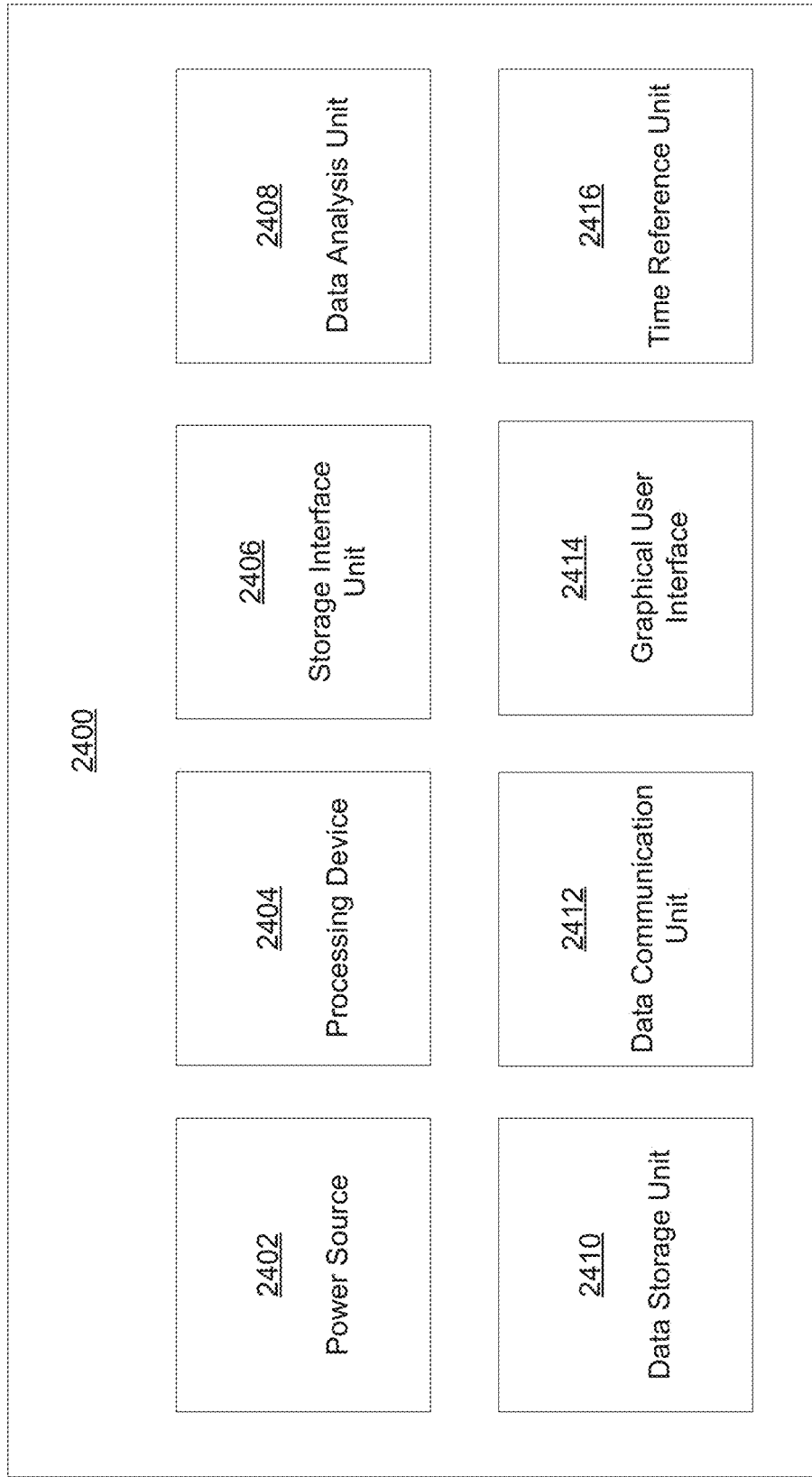
FIG. 24 illustrates a block diagram of electronic components of a wearable device, according to an embodiment.

FIG. 24 illustrates a block diagram of electronic components 2400 of a wearable device such as the wearable device 100, according to an embodiment. The electronic components 2400 may include a power source 2402, a processing device 2404, a sensor interface unit 2406, a data analysis unit 2408, a data storage unit 2410, a data communication unit 2412, a graphical user interface 2414, and a time reference unit 2416. The electronic components 2400 may be embedded in a band of the wearable device and may be electrically coupled to one or more sensors, such as an optical sensor, an impedance sensor, a humidity and/or a temperature sensor.

In one embodiment, the electronic components 2400 may include a power unit 2402 that supplies power to components of the electronic components 2400. The power unit 2402 may include a battery to supply power and a charging unit that may charge the battery. Alternatively, electronic components 2400 may be connectable to an energy source that powers the electronic components 2400. In one embodiment, a charger may be used to recharge a battery or other energy source of the power unit 2402. In one embodiment, an external battery (e.g., located in the band, and so forth) may be coupled to the power unit 2402.

In one embodiment, the electronic components 2400 may include a processing device 2404. The processing device 2404 may include a central processor to process the data and/or information of the other components that include the electronic components 2400 or other units, interfaces, and/or devices attached to or in communication with the electronic components 2400.

In another embodiment, the electronic components 2400 may include a sensor interface unit 2406. The sensor interface unit 2406 may be coupled to the sensors and/or may perform one or more measurements relating to a physiological condition of a body using one or more of the sensors. In one embodiment, the sensor interface 2406 and the processing device 2404 may be the same component. In another embodiment, the sensor interface 2406 may be communicatively coupled to the processing device 2404. The sensor interface 2406 may use the one or more sensors to take measurements relating to a physiological condition, physiological parameter, and/or physiological constituent of a body, an impedance measurement, a backscatter measurement, a temperature measurement of a body or of an environment, a humidity measurement of a body or of an environment, an airflow measurement (e.g., temperature measurements, pressure measurements, and so forth) of the environment, or another physiological state or environment condition measurement. In an embodiment, the sensor interface 2406 may be coupled to the processing device 2404 and the ambient humidity, airflow, skin temperature, and/or ambient temperature sensors. In this example, the sensor interface 2406 may receive data from the ambient humidity, airflow, skin temperature, and/or ambient temperature sensors relating to the ambient humidity, airflow, skin temperature, and ambient temperature at the location of the electronic components 2400. In an embodiment, the sensor interface 2406 may be communicatively coupled to the processing device 2404 and the optical sensor. In this example, the sensor interface unit 2406 may receive data from the optical sensor relating to a portion of light that was reflected off an artery or other muscular-walled tube. Alternatively, the sensor interface 2406 and the processing device 2404 may be the same component. The sensor interface unit 2406 may measure the backscatter of one or more wavelengths that have been reflected off a vein, artery, or other muscular-walled tube using the portion of light. In an embodiment, the sensor interface 2406 may be communicatively coupled to the processing device 2404 and the impedance sensor. In this example, the sensor interface 2406 may receive data from the impedance sensor relating to detecting a portion of an electric current. In an embodiment, the sensor interface 2406 may be communicatively coupled to the processing device 2404, a first humidity sensor, a second humidity sensor, a first temperature sensor, and/or a second temperature sensor. In this example, the sensor interface 2406 may receive data from the humidity and temperature sensors relating to the humidity and temperature of the user at the location of the electronic components 2400.

In another embodiment, the electronic components 2400 may include a time reference unit 2416 that generates time reference data usable to control the time at which data may be collected from the sensor interface unit 2406. The time reference unit 2416 may also be used to calculate spatial and/or temporal derivatives between information received from the sensor interface unit 2406. In one embodiment, the time reference unit 2416 may keep track of a calendar time, such as a clock. Alternatively, the time reference unit 2416 may act as a timer, keeping track of a lapsed time or decrementing from a defined time to zero. The timer of the time reference unit 2416 may be used to collect information or data from the sensor interface 2406 for a defined period of time or to record how long the sensor interface 2406 collects data.

In another embodiment, the electronic components 2400 may include a data analysis unit 2408. The data analysis unit 2408 may be communicatively coupled to the processing device 2404, sensor interface unit 2406, time reference unit 2416, and other components of the electronic components 2400. The data analysis unit 2408 may determine that a physiological condition, physiological parameter, and/or physiological constituent has changed for a user by comparing temporal data from the time reference unit 2416 to measurement data from the sensor interface unit 2406. The data analysis unit 2408 may communicate the physiological condition, physiological parameter, and/or physiological constituent to a user through the graphical user interface (GUI) 2414.

In another embodiment, the electronic components 2400 includes a GUI 2414. The graphical user interface may be a monitor screen, liquid crystal display (LCD), light emitting diode (LED) display, or the like. In one embodiment, the GUI may present information such as a hydration condition to the user. In another embodiment, the user may be able to interact with the electronic components 2400 though inputs or icons on the GUI.

Figure 25:
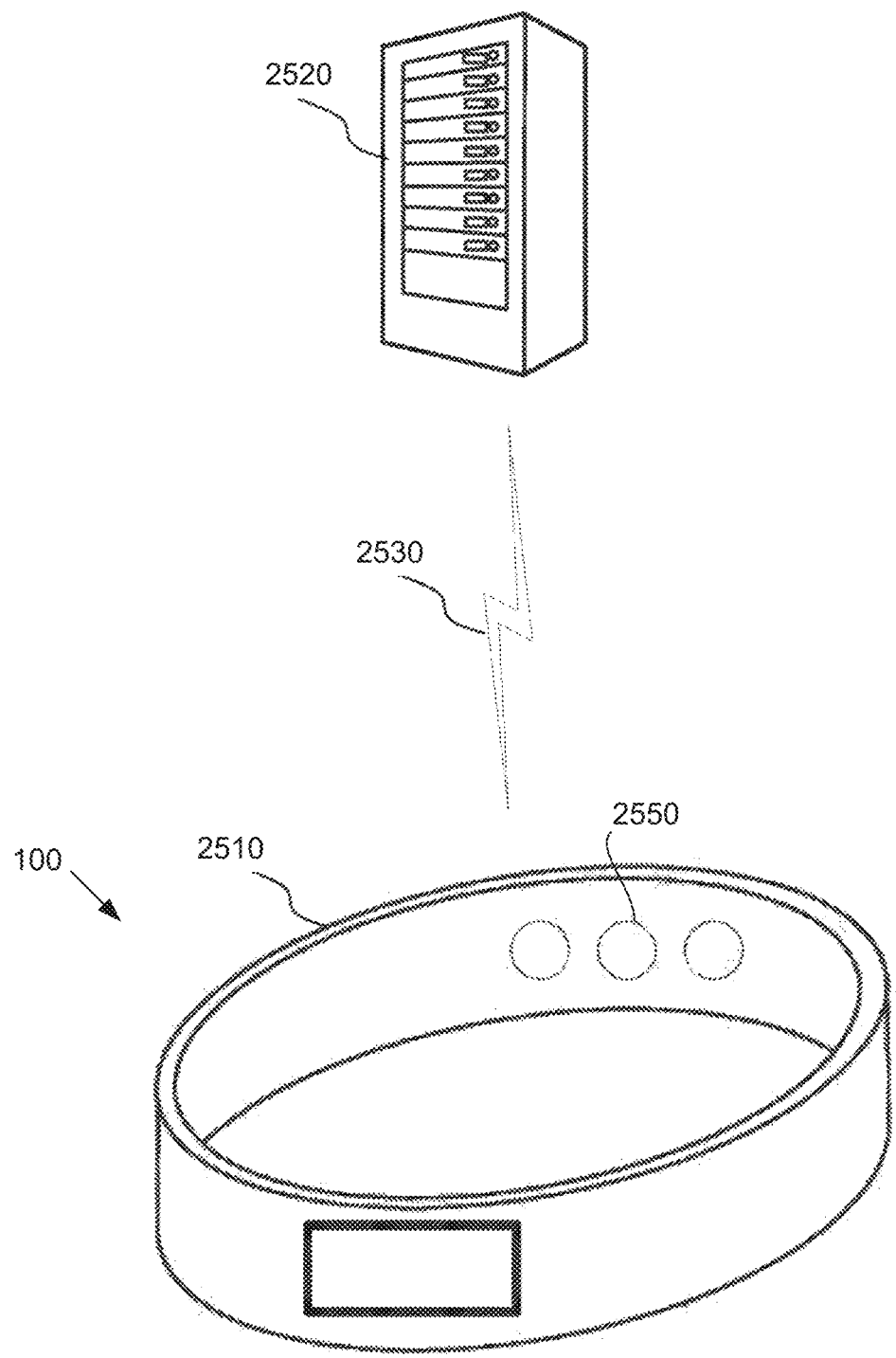
FIG. 25 illustrates a wearable device in communication with a computing device, according to one embodiment.

FIG. 25 illustrates the wearable device 100 in communication 2530 with a computing device 2520, according to one embodiment. In an embodiment, sensor measurements collected and/or stored by the wearable device 100 may be processed or analyzed by a processor or processing device of the wearable device 100 and/or by a computing device 2520 in communication with the wearable device 100. The wearable device 100 may be in direct and/or indirect communication with the computing device 2520. In one embodiment, the communication 2530 may be a communication link using BLUETOOTH® technology, a communication link using ZIGBEE® technology, radio signal, or other direct communication systems. In one embodiment, the other computing device 2520 may be a server that stores information, such as present sensor measurements or sensor measurements previously taken by the wearable device 100, or sensor measurements such as blood glucose measurements taken from a group of individuals, as discussed herein. In another embodiment, the computing device 2520 may be a mobile computer device, such as a laptop computer, tablet, or a smartphone. The wearable device 100 may communicate information, such as sensor measurements, to the computing device 2520. In an embodiment, the computing device 2520 may process and/or analyze the sensor measurements and/or information received from the wearable device 100. In another example, the computing device 2520 may send processed data, analyzed data, measurement results, and/or other information to the wearable device 100. In another example, the computing device 2520 may communicate calibration information to the wearable device 100.

In one embodiment, the wearable device 100 may be a standalone device with a processing device to analyze or process: information taken from one or more sensors 2550 of the wearable device 100; information received from other devices; and/or information stored in a memory of the wearable device 100.

In another embodiment, the wearable device 100 may communicate locally with the computing device 2520 using a wireless communication network or a cellular communication network. The local computing device 2520 may be a smartphone, tablet device, personal computer, laptop, a local server, and so forth. In yet another embodiment, the wearable device 100 communicates with a non-local or remote computing device 2520 using the wireless communication network or the cellular communication network. The non-local or remote computing device 2520 may be a remote server, a cloud-based server, a back-end server, or other remote electronic devices.

In an embodiment, the communication 2520 may occur over a wireless communication network. The wireless communication network may be a cellular network employing wireless networking standards such as a third generation partnership project (3GPP®) release 8, 9, 10, 11, 12, 13, 14, or 15 or Institute of Electronics and Electrical Engineers (IEEE®) 802.16.2, 802.16k, 802.16.1, 802.16p, 802.16.1b, 802.16n, 802.16.1a, and 802.16-2017. In another example, the wearable device 100 may communicate with the computing device 2520 over a secure wireless local area network (WLAN), a secure personal area network (PAN), and/or a personal wide area network (PWAN). The wearable device 100 in the WLAN may use the WI-FI® technology and IEEE® 802.11 standards defined by the WI-FI ALLIANCE® such as the IEEE® 802.11-2016, 802.11ay, 802.11ba, 802.11ax. 802.11az, 802.11bb, 802.11bc, 802.11bd, 802.11be, 802.11ah-2016, 802.11ai-2016, 802.11aj-2018, 802.11ak-2018, or 802.11aq-2018 standards. Alternatively, the wearable device 100 and the computing device 2520 in the WLAN may use other technologies and standards. Similarly, the wearable device 100 in the personal area network (PAN) or wireless personal area network (WPAN) may use a BLUETOOTH® technology and IEEE® 802.15 standards defined by the BLUETOOTH® Special Interest Group, such as BLUETOOTH® v1.0, BLUETOOTH® v2.0, BLUETOOTH® v3.0, BLUETOOTH® v4.0, or BLUETOOTH® v5.0 (including BLUETOOTH® low energy). Alternatively, the wearable device 100 in the PAN may use other technologies and standards. In another embodiment, the communications network may be a ZIGBEE® connection developed by the ZIGBEE® Alliance such as IEEE® 802.15.4-2003 (ZIGBEE® 2003), IEEE® 802.15.4-2006 (ZIGBEE® 2006), IEEE® 802.15.4-2007 (ZIGBEE® Pro). The WLAN or PWAN may be used to transmit data over long distances and between different local area networks (LANs), WLAN s, metropolitan area networks (MANs), wide area networks (WANs) or other localized computer networking architectures.

The wearable device 100 and the computing device 2520 may be in indirect communication using a communications network such as the wireless communication network (such as a network using WI-FI® technology) and/or using a cellular communication network (e.g., a network using 3rd Generation Partnership Project (3GPP®), and so forth) to communicate data or measurement information. In an embodiment, the wearable device 100 may take sensor measurements using sensors 2550 and communicate the sensor measurements to the computing device 2520 via the wireless communication network and/or the cellular communication network. In another example, the computing device 2520 may receive sensor measurements from the wearable device 100 via the wireless communication network and/or the cellular communication network and process the sensor measurements and/or analyze the sensor measurements. When the computing device 2520 has processed the sensor measurements and/or analyzed the sensor measurements, the computing device 2520 may communicate the processed sensor measurements, analyzed sensor measurements, sensor measurement results, or other information to the wearable device 100 via the wireless communication network and/or the cellular communication network.

Figure 26:
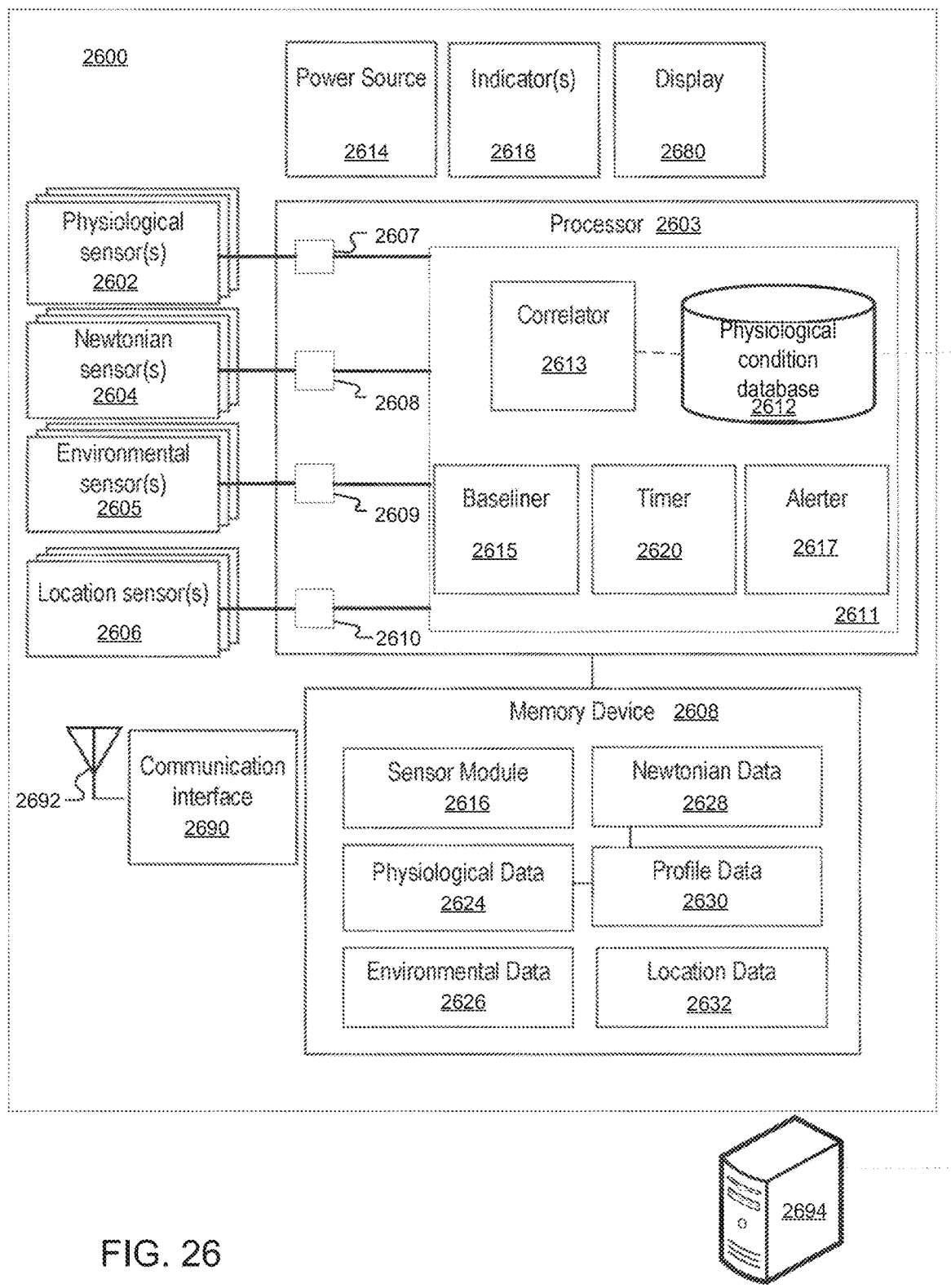
FIG. 26 illustrates a block diagram of an electronic device with a correlator, a baseliner, and an alerter, according to an embodiment.

FIG. 26 illustrates a block diagram of the wearable device 100 with a correlator 2613, a baseliner 2615, and an alerter 2617, according to one embodiment. The wearable device 100 may include, without limitation, one or more physiological sensor(s) 2602, one or more Newtonian sensor(s) 2604, one or more environmental sensor(s) 2605, one or more location sensor(s) 2604, a processing device 2603, a memory device 2608, a display 2680, a communication interface 2690 (such as a radio frequency (RF) circuit), and an antenna 2692 coupled to the communication interface 2690.

In one embodiment, the communication interface 2690 may communicate, via the antenna 2692, with an external electronic device such as a computing device, and with other wireless devices such as electronic device 2600 of other users. In an embodiment, the communication interface 2690 may communicate the information using a cellular network, a wireless network, or a combination thereof. In an embodiment, the communications network may be the same as or similar to the cellular network described regarding FIG. 25.

In another example, the wearable device 100 may communicate with a device over a secure WLAN, a secure PAN, and/or a PWAN. The wearable device 100 in the WLAN may use technology and/or standards the same as or similar to those described regarding FIG. 25. Alternatively, the devices in the WLAN may use other technologies and standards. Similarly, the wearable device 100 in the PWAN or WLAN may use technologies and standards similar to those described regarding FIG. 25. Alternatively, the wearable device 100 in the secure PAN may use other technologies and standards. In another embodiment, the communications network may be a ZIGBEE® connection the same as or similar to those described regarding FIG. 25. The WLAN or PWAN may be used to transmit data over long distances and between different LANs, WLANs, MANs, WANs or other localized computer networking architectures.

In one embodiment, the wearable device 100 may communicate data with the other devices via another device, such as a smartphone or tablet computing device. For example, the communication interface 2690 may pair with a smartphone via the wireless network. The smartphone may receive data using the wireless network and may communicate the data to the other device. In another embodiment, the wearable device 100 may communicate information with the other device via repeaters or a relay system. For example, a user of the wearable device 100 may be outside a coverage area for the cellular network or the wireless network, e.g., a farm worker out in the field. In this example, the wearable device 100 may determine that it is outside the coverage area and switch to communicating via the repeaters or the relay system.

In one embodiment, the wearable device 100 may determine it is outside a coverage area when it does not receive a signal from the cellular network or the wireless network. In another embodiment, the wearable device 100 may ping the cellular network or the wireless network (such as a tower within the cellular network or the wireless network) and determine that it is outside the coverage area when the wearable device 100 does not receive a reply to the ping. In another embodiment, multiple electronic devices 2600 may communicate with each other to form a piconet. In this embodiment, a first electronic device may determine it is outside the coverage area and may scan for a second electronic device, where the second electronic device is in the coverage area or in communication with another electronic device in the coverage area. When the first electronic device finds the second electronic device, the wearable device may communicate information to an end device or to the cellular network or the wireless network via the second electronic device.

The processor 2603 may include a first sensor interface 2607 for receiving sensor data from the physiological sensor(s) 2602, a second sensor interface 2608 for receiving sensor data from the Newtonian sensor(s) 2604, a third sensor interface 2609 for receiving sensor data from the environmental sensor(s) 2605, a fourth sensor interface 2610 for receiving sensor data from the location sensor(s) 2606, and a processing element 2611. The processing element 2611 in turn may include a correlator 2613, a baseliner 2615 and/or an alerter 2617. The memory device 2608 may also include, without limitation, a sensor module 2616, physiological data 2624, environmental data 2626, Newtonian data 2628, and profile data 2630, location data 2632.

The wearable device 100 may include a sensor array with two or more sensors. In the depicted embodiment, the wearable device 100 may include one or more physiological sensors 2602, one or more Newtonian sensors 2604, one or more environmental sensors 2605, one or more location sensors 2606, or a combination thereof. In some instances, the Newtonian sensors 2604 may be physiological sensors. That is, in some embodiment, the activity level may be determined from one or more physiological measurements.

A physiological measurement may be any measurement related to a living body, such as a human's body or an animal's body. Thy physiological measurement may correspond to a condition of the body, a parameter of the body, or a constituent of the body. A condition of the body may include a heart condition, diabetes, a psychological condition, fatigue, dehydration, and so forth. A parameter of the body may include a blood pressure, a heart rate, a temperature, pulse oximetry measurement, and so forth. A constituent of the body may include a blood glucose level, a glucose level, an insulin level, a hydration level, a urea content, a hematocrit measurement, and so forth. The physiological measurement may be a measurement made to assess body functions. Physiological measurements may be simple, such as the measurement of body or skin temperature, or they may be more complicated, for example measuring how well the heart is functioning by taking an ECG (electrocardiograph), determining a blood glucose level of the body, or determining a hydration condition of the body. Physiological measurements may also include motion and/or movement of the body. In some cases, these physiological measurements may be taken as an aggregate, e.g., as physiological data, with which to correlate to other physiological measurements, a physiological parameter, and/or an environmental parameter.

A parameter may be considered a measurable quantity (such as heart rate, temperature, altitude, and oxygen level, as just a few examples). When measurements of parameters are taken in the aggregate, the measurements may form data which may be analyzed and correlated to other data or parameters, to identify trends or to identify when meeting (or exceeding) certain thresholds that trigger alerts or other actions and the like.

The physiological sensors 2602 may include a pulse oximeter sensor, an electrocardiography (ECG) sensor, a fluid level sensor, an oxygen saturation sensor, a body core temperature sensor, a skin temperature sensor, a plethysmograph sensor, a respiration sensor, a breath rate sensor, a cardiac sensor (e.g., a blood pressure sensor, a heart rate sensor, a cardiac stress sensor, or the like), an impedance sensor (e.g., a miniaturized impedance sensor), an optical sensor, a spectrographic sensor, an oxygen saturation sensor, humidity and/or temperature sensors, and/or a microspectrometer. Alternatively, other types of sensors may be used to measure physiological measurements, including measurements to determine activity levels of a person wearing the wearable device.

The Newtonian sensors 2604 may be any of the physiological sensors described above, but in some cases, the Newtonian sensors 2604 are activity or motion sensors, such as, for example, a gyroscope sensor, a vibration sensor, an accelerometer sensor (e.g., a sensor that measures acceleration and de-acceleration), a three dimensional (3D) accelerometer sensor (e.g., sensors that measure the acceleration and de-acceleration and the direction of such acceleration and de-acceleration), a force sensor, a pedometer, a strain gauge, a magnetometer, and a geomagnetic field sensor that may be used for activity level measurements; whereas the physiological sensors 2602 may be used for specific physiological measurements.

In one embodiment, an environmental measurement may be any measurement of an area approximate or adjacent a user. The environmental sensors 2605 may be a humidity sensor, an ambient temperature sensor, an altitude sensor, a barometer, and so forth. A location measurement may be any measurement of a location of the user or a movement of the user. The location sensor 2606 may be a global positioning system (GPS), a triangulation system, or a location sensor. One or a combination of the physiological data 2624, the environmental data 2626, the Newtonian data 2628, the profile data 2630, and the location data 2632 may be obtained from other sources such as from sources reachable in the cloud or online, and or through a network such as the networks described and/or illustrated regarding FIG. 25.

In another embodiment, the environmental measurement may be any measurement of a local or central location measurement of where a user is located. For example, one or more environmental sensors 2605 may be located at a location within a threshold radius of the user, such as a threshold radius from the user location. In this example, the environmental sensors 2605 may take environmental measurements and relay the information to the wearable device 100 or to a communication hub that has a communication channel established with the wearable device 100. Alternatively, the environmental sensors 2605 may take environmental measurements and relay the information to a processing hub that may analyze the environmental measurements to determine selected environmental factors (such as a humidity level, a heat index, and so forth) and may communicate the environmental factors to the wearable device 100 or to another electronic device. In another embodiment, the processing hub may receive the environmental measurements from the environmental sensors 2605 and other measurements (such as physiological measurements) from the wearable device 100. The processing hub may analyze the environmental measurements and the other measurements to determine selected result data, such as a hydration level of a user or a health level of the user. In another embodiment, the wearable device 100 may take a first set of environmental measurements and the local environmental sensors 2605 may take a second set of environmental measurements. The first set of environmental measurements and the set of environmental measurements may be combined or aggregated and the processing hub and/or the wearable device 100 may analyze the aggregated environmental measurements.

In another embodiment, the environmental measurements may be from an environmental information outlet or provider. For example, the environmental information outlet or provider may be a weather station, a news station, a television station, an online website, and so forth. The wearable device 100 or the processing hub may receive the environmental information from the environmental information outlet or provider may use the environmental information to determine selected physiological and/or environmental data or factors.

The first sensor interface 2607 may be coupled with the one or more physiological sensors 2602, a second sensor interface 2609 may be coupled with the one or more Newtonian sensors 2604, a third sensor interface 2609 may be coupled with the one or more environmental sensors 2605, and a fourth sensor interface 2610 may be coupled with the one or more location sensors 2606. The processing element 2611 may be operable to execute one or more instructions stored in the memory device 2608, which may be coupled with the processor 2603. In some cases, the processing element 2611 and memory device 2608 may be located on a common substrate or on a same integrated circuit die. Alternatively, the components described herein may be integrated in one or more integrated circuits. The memory device 2608 may be any type of memory device, including non-volatile memory, volatile memory, or the like. Although not separately illustrated the memory device may be one or more types of memory configured in various types of memory hierarchies.

The memory device 2608 may store physiological data 2624, such as current and past physiological measurements, as well as profile data 2630, including user profile data, bibliographic data, demographic data, and the like. The physiological data 2624, and in some cases the profile data 2630, may also include processed data regarding the measurements, such as statistical information regarding the measurements, as well as data derived from the measurements, such as predictive indicators, results, and/or recommendations.

In an embodiment, the profile data 2630 may also include information connected to user profiles of the users that wear the wearable device 100, such as a gender of the user, an age of the user, a body weight or mass of the user, a health status of the user, a fitness level of the user, or a family health history of the user. In another example, the profile data 2630 may include occupational information of the users that wear the wearable device 100, such as a job type, a job title, whether the job is performed indoors or outdoors, a danger level of the job, and so forth. For example, the job types may include an elderly live-at-home job, an oil driller, a construction worker, a railroad worker, a coal mine worker, a job in confined spaces, a fireman, a construction worker, an outdoor worker, an office worker, a truck driver, a child, a stay-at-home parent, a disabled individual, or any other occupation which might provide an individual with income and/or otherwise occupy the individual's time.

In an embodiment, the wearable device 100 may receive the profile data 2630 via a touch screen device integrated into the wearable device 100 or coupled to the wearable device 100. In another example, the wearable device 100 may receive the profile data 2630 via a communication port of the wearable device 100. For example, the wearable device 100 may receive profile data 2630 from another device via a wired communication connection (e.g., a universal serial bus) or via a wireless communication connection (e.g., a BLUETOOTH® communication technology).

The profile data 2630 may also be linked to various physiological data 2624 and Newtonian data 2628 and be tracked over time for the users. The profile data 2630 may also include baselines of physiological parameters for respective users. In an embodiment, the baselines are of a heart rate, a blood pressure, bioimpedance, skin temperature, oxygen levels, hydration levels, electrolyte levels, blood glucose levels, and so forth. When the baselines are included with the user profiles, the user profiles may be referred to as baseline profiles for the respective users.

The memory device 2608 may also store the environmental data 2626, the Newtonian data 2628, the profile data 2630, and/or the location data 2632. The Newtonian data 2628, environmental data 2626, or location data 2632 may be current and past measurements, as well predictive data for predictive modeling of activity levels, environmental levels, or locations. The memory device 2608 may store instructions of the sensor module 2616 and instructions and data related to the correlator 2613, the base liner 2615 and the alerter 2617, which perform various operations described below.

In particular, the sensor module 2616 may perform operations to control the physiological sensors 2602, Newtonian sensors 2604, environmental sensors 2605, and location sensors 2606, such as when to turn them on and off, when to take a measurement, how many measurements to take, how often to perform measurements, and so forth. For example, the sensor module 2616 may be programmed to measure a set of physiological measurements according to a default pattern or other adaptive patterns to adjust when and how often to take certain types of measurements. The measurements may be stored as the physiological data 2624, the environment data 2626, and the Newtonian data 2628, location data 2632, and some of them may also be integrated as a part of the profile data 2630, as discussed.

In an embodiment, the processing element 2611 (e.g., one or more processor cores, a digital signal processor, or the like) may execute the instructions of the sensor module 2616 and those related to the correlator 2613, the baseliner 2615, the alerter 2617 and/or other modules or routines. Alternatively, the operations of the sensor module 2616 and the correlator 2613, the baseliner 2615, and the alerter 2617 may be integrated into an operating system that may be executed by the processor 2603. In one embodiment, the processing element 2611 measures a physiological measurement via the first sensor interface 2607. The processing element 2611 may measure an amount of activity of the wearable device 100 via the second sensor interface 2608. The amount of activity could be movement or motion of the wearable device 100 (e.g., by tracking location), as well as other measurements indicative of the activity level of a user, such as heart rate, body temperature, skin luminosity, or the like. The processing element 2611 may measure an environmental measurement via the third sensor interface 2609. The processing element 2611 may measure a location measurement via the fourth sensor interface 2610.

In one embodiment, the Newtonian sensors 2604 may include a hardware motion sensor to measure at least one of movement or motion of the wearable device 100. The processing element 2611 may determine the amount of activity based the movement or motion of the wearable device 100. The hardware motion sensor may be an accelerometer sensor, a gyroscope sensor, a magnetometer, a GPS sensor, a location sensor, a vibration sensor, a 3D accelerometer sensor, a force sensor, a pedometer, a strain gauge, a magnetometer, and a geomagnetic field sensor.

The processor 2603 may further execute instructions to facilitate operations of the wearable device 100 that receive, store and analyze measurement data, environmental data, location data, and profile data. The indicator(s) 2618 may include one or more of a light, a display, a speaker, a vibrator, and a touch display, useable to alert the user to take actions in response to trending levels of: physiological parameters during or after physical activity and/or prepare for undertaking anticipated physical activity; environmental parameters; activity parameters, or location parameters.

In some embodiments, for example, the correlator 2613 may analyze measurement data to correlate physiological data, environmental data, activity data, location data, or user experienced feedback with a physiological parameter, environmental parameter, activity parameter, a location parameter, or user experienced feedback to predict a change in a level of the physiological parameter, environmental parameter, activity parameter, or a location parameter. In one embodiment, the user experienced feedback may be physiological or psychological symptoms experienced by the user. For example, the physiological or psychological symptoms may include: headaches, dizziness, tiredness, mental fatigue, increased thirst, dry mouth, swollen tongue, physical weakness, confusion, sluggishness, and so forth.

Such prediction may enable timely and accurate recommendations to a user in terms of blood glucose levels (e.g. consuming food or taking an insulin shot, and so forth), adjusting effort levels or other specific actions to address a trend or a change in the physiological parameter, the environmental parameter, the activity parameter, or the location parameter. The recommendations may be displayed in the display 2680, sent via an alert through one of the indictor(s) 2618 or displayed in another device such as a smart phone or tablet or other computing device.

In another embodiment, the correlator 2613 may also track and analyze Newtonian data of the user related to physiological or determined parameters (such as heart rate, oxygenation, skin luminosity, hydration, and the like), related to location and type of activity (such as activity levels associated with being at the gym, riding a bike, attending class, working at a desk, sleeping, or driving in traffic, and the like) and/or related to scheduling information (such as appointments on a calendar, invites received from friends, or messages related to travel and/or activity plans, and the like). Through this analysis, the wearable device 100 may track activity data over time, intelligently and continuously (or periodically) analyze all of this information and alert the user through the indicator(s) 2618 to take a specific action at a proper time before a start of a dehydration condition. The specific action may include to hydrate extra for a time period before physical activity and to eat at least two hours before any physical activity, or other such timing that may be general to most users or customized to a training or nutrition routine of a specific user.

In another embodiment, the correlator 2613 may build an individualized profile for the user. The correlator 2613 may receive the individualized profile information from an input device of the wearable device 100. For example, the correlator 2613 may receive the individualized profile information from a touch screen of the wearable device 100. In another example, the correlator 2613 may receive the individualized profile information from a device in communication with the wearable device 100 (such as via a USB port or using a BLUETOOTH® technology). In another embodiment, the wearable device 100 may include a memory that stores the individualized profile information for the user.

In another embodiment, the correlator 2613 may utilize data from multiple physiological sensors 2602 integrated into the wearable device 100 to determine a physiological condition of the user. For example, the wearable device 100 may be configured to measure blood glucose. Blood glucose may be determined by illuminating a vein and/or artery and processing light reflected off the vein and/or artery. By processing the reflected light and comparing the reflected wavelengths to wavelengths known to be reflected by various blood and/or body constituents, a percentage of the blood constituting blood glucose may be determined. A person may be determined to be hyperglycemic or hypoglycemic based on the percentage of blood glucose. However, the blood glucose percentage may be affected by the percentage of other blood constituents. A primary constituent of blood is water. Thus, if the user is dehydrated, the percentage of blood glucose may be higher for the user than when the user is properly hydrated, and it may incorrectly be determined the user is hyperglycemic.

In an embodiment, the correlator 2613 may use a measurement taken by one physiological sensor 2602 to calibrate a measurement taken by another physiological sensor 2602 and thereby prevent false positives for the physiological condition. For example, the user may want to know the blood glucose level. The wearable device 100 may include a light source and microspectrometer, and a miniaturized impedance sensor. The processor 2603 may obtain a blood glucose measurement by the light source and microspectrometer, and may obtain a hydration level by the miniaturized impedance sensor. The blood glucose and hydration data may be received by the correlator 2613. The correlator 2613 may determine, based on the hydration condition, an expected percentage of water in blood of a user. For example, the memory device 2608 may have stored in the physiological data 2624 a table relating various impedance measurements to various hydration levels, which hydration levels may be related to a volume of water in the measured tissue and/or tissues. In turn, the hydration levels may be related to various percentages of water in blood. The correlator 2613 may compare the percentage of water in blood obtained from the impedance measurement to the percentage of glucose in the blood determined by the spectroscopy measurement. In a specific example, the correlator 2613 may determine the user has elevated blood glucose percentage, but the elevation is due to dehydration.

In an embodiment, the miniaturized impedance sensor may take consecutive impedance measurements at a discreet frequency. In another embodiment, the miniaturized impedance sensor may take consecutive impedance measurements at different frequencies, thereby functioning as an impedance spectrometer. For example, the miniaturized impedance sensor may take a first measurement at 5 kilohertz, a second measurement at 50 kilohertz, a third measurement at 500 kilohertz, a fourth measurement at 5 megahertz, a fifth measurement at 50 megahertz, and a sixth measurement at 500 megahertz. In general, a range of frequencies used to interrogate the body part of the user may range from 5 kilohertz to 500 kilohertz. In one embodiment, the discreet frequency may include 200 kilohertz and/or 200 megahertz. A frequency and/or range of frequencies may correspond to absorption harmonics of constituents of the body part, such as molecules that make up the body part, structures within the body part, fluids within the body part, and so forth.

The individualized profile may include physiological information associated with the user. For example, the physiological information may include a healthy blood glucose range for the user, an average heart rate of the user, an age of the user, a health level of the user, and so forth. The individualized profile may also include information associated with a location or environment that the user may be located. For example, the individualized profile may include: humidity level information, such as when the user is located in a dry climate or in a humid climate; altitude level information, such as when the user is located at a relatively high altitude or a relatively low altitude; seasonal information, such as if it is winter where the user may be located or summer. The correlator 2613 may also determine an environmental effect on the user for the location where the user may be located at. For example, if the user is located at their home that is at a high altitude with a dry climate and it is a winter season, the correlator 2613 may determine that the user may be acclimated to high altitudes, dry climates, and the winter season. The correlator 2613 may also update the user profile when the user changes location. For example, when the user leaves their home location and goes on a vacation to a location that is at a low altitude, a humid climate, and it is a summer season, the correlator 2613 may determine that the user may not be acclimated to the low altitude, humid climate, and summer season.

In one embodiment, the wearable device 100 may alert the user of the changes to the individualized profile. In another embodiment, the wearable device 100 may alert the user of to effects associated with the changes to the individualized profile. For example, the wearable device 100 may access a table of predetermined effects of the user changing their user profile. In an embodiment, the table may indicate that when the user switches from a low altitude to a high-altitude location, the user may experience altitude sickness. In another example, the table may indicate that when the user switches from a dry climate to a humid climate location, an ability of a body of the user to cool itself down may be decreased when an ambient temperature is relatively high. In another embodiment, the table may indicate when the current user profile indicates safety risks or physiological performance changes.

In another embodiment, the individualized profile may also include information associated with clothing or apparel worn by the user of the wearable device 100. For example, the individualized profile may indicate that a user may wear different types of apparel for different environments including: a thickness of fabric; a type of a fabric, such as wool or cotton; a number of clothes layers worn by the client; accessories worn by the client, such as hard hats, steel-toed shoes, safety googles, safety belts, and so forth; and gender types of apparel, such as women's and/or men's apparel. In an embodiment, the correlator may adjust measurement information or measurement results based on the different types of clothing or apparel. For example, the correlator 2613 may determine that the user is a firefighter and is wearing multiple layers of clothing to protect against fire. In this example, the correlator 2613 may determine that a cause of a hydration level of the user decreasing may be the multiple layers of clothing cause the firefighter to sweat more and lose more fluid than a typical number of layers of clothing worn by the user. In another example, the correlator 2613 may determine that the user is a marathon runner who is running. In this example, the correlator 2613 may determine that a cause of a blood glucose level of the user decreasing may be the extended period of running using all freely available blood glucose.

In one embodiment, the alerter 2617 may decide the most appropriate timing and mode of alert, whether through one of the indicator(s) 2618, the display 2680 or another device such as a smart phone, tablet or the like. The type of indicator used to alert the user may also be customized to or by the user. For example, the alerter 2617 may determine blood glucose of a user is in a moderately high range such that the user should take an insulin shot and/or may alert the user to take an insulin shot.

In one embodiment, the correlator 2613 may determine a correlation between different data points or data sets of the input data (such as data collected from different sensors, devices, or obtained from the cloud or online). The correlator 2613 may determine different types of correlations of the data points or data sets. In an embodiment, the correlator 2613 may execute a Pearson product moment correlation coefficient algorithm to measure the extent to which two variables of input data may be related. In another example, the correlator 2613 may determine relations between variables of input data based on a similarity of rankings of different data points. In another example, the correlator 2613 may use a multiple regression algorithm to determine a correlation between a data set or a data point that may be defined as a dependent variable and one or more other data sets or other data points defined as independent variables. In another example, the correlator 2613 may determine a correlation between different categories or information types in the input data.

In further examples, when the correlator 2613 determines a correlation between the different data points or data sets, the correlator 2613 may use the correlation information to predict when a first event or condition may occur based on a second event or condition occurring. In another example, when the correlator 2613 determines a correlation between the different data points or data sets, the correlator 2613 may use the correlation information to determine a blood glucose level. As discussed in the preceding paragraphs, a high blood glucose level may be an event that negatively impacts safety or health of the user. In another example, when the correlator 2613 determines a correlation between the different data points or data sets, the correlator 2613 may use the correlation information to determine a cause of a condition and/or event, such as a hydration condition.

Additionally, or alternatively, the correlator 2613 may determine a correlation between physiological data 2624, environmental data 2626, Newtonian data 2628, profile data 2630, and location data 2632. For example, the input data may include blood glucose level data (physiological data) and ambient temperature data (environmental data). In this example, the correlator 2613 may identify a correlation between an ambient temperature, an amount of sweating, a blood glucose level of a user, and a hyperosmolar hyperglycemic state (HHS). The correlator 2613 may identify the correlation between the ambient temperature, the amount of sweating, the blood glucose level, and the HHS by using a regression algorithm with the HHS as an independent variable and the ambient temperature, the amount of sweating, and the blood glucose level as dependent variables. When the correlator 2613 has identified the correlation between the HHS, the ambient temperature, the amount of sweating, and the blood glucose level, the correlator 2613 may predict altered consciousness, confusion, disorientation, and/or a coma based on a change in a the blood glucose level of a user or a rate of change of a blood glucose level of a user, a change in the amount of sweating of the user or a rate of change in the amount of sweating of the user, and a change in the ambient temperature or a rate of change in the ambient temperature.

Additionally, or alternatively, the correlator 2613 may determine a correlation between a fatigue event, an altitude level, and an oxygenation level of a user. For example, the correlator 2613 may determine a correlation between an increase in the altitude level, a decrease in the oxygenation level of the user, and an increase in a fatigue event. When the correlator 2613 determines the correlation between the altitude level, the oxygenation level, and the fatigue event, the correlator 2613 may predict an increase or decrease in a probability of a hydration condition change based on a change in the oxygenation level of user and the altitude level at which the user may be currently at. In an embodiment, the correlator 2613 may use the individualized profile information (as discussed in the preceding paragraphs) of the user to determine the predicted increase or decrease in the probability of a hydration condition change. For example, the correlator 2613 may determine a change in altitude level of the user from a relatively low altitude to a relatively high altitude. The correlator 2613 may use the individualized profile information to determine that the user may be acclimated to the relatively high altitude (such as if they live at a high altitude) and adjust the predicted increase or decrease in the probability of a hydration condition change for the change in altitude in view of the individualized profile information. For example, the correlator 2613 may predict that the change from the low altitude to the high altitude will not increase or decrease the probability of a user experiencing a dangerous change in hydration condition.

In a further example, the correlator 2613 may identify a correlation between location information and physiological data of a user. For example, the correlator 2613 may determine a location of a user for at a period of time, such as by using GPS sensor data or triangulation sensor data. In this example, the correlator 2613 may receive physiological measurement data (such as heart rate measurement data, optical spectroscopy data, blood glucose level measurement data, blood pressure measurement data, hydration condition data, and so forth). The correlator 2613 may correlate the location of the user with the physiological measurement data to increase an accuracy of data analysis, a diagnosis, or result data and/or provide additional details regarding a cause of a change in a blood glucose level.

In an embodiment, the correlator 2613 may determine that a user may be at work in an office location. When the correlator 2613 detects an increase in a heart rate or a blood pressure of a user, the correlator 2613 may correlate heart rate or blood pressure data and the location information to determine a cause of the cognitive ability reduction event. For example, when a heart rate or blood pressure of a user increases while at a work in an office, the correlator 2613 may determine that the heart rate or blood pressure increase may be due to psychological causes (such as stress) rather than physiological causes (such as exercising or working out) because the user may be at a location where the user may not be likely to physically exert himself or herself.

In another example, the correlator 2613 may determine an occupation of the user, such as by using the profile data 2630. In one embodiment, the correlator 2613 may determine that the occupation of the user may be a higher risk occupation (e.g., a statistically more dangerous occupation). For example, the correlator 2613 may access a database or list (stored at the memory device 2608 or externally) that includes information associated with an occupation, such as environmental exposure. When the correlator 2613 detects that the occupation of the user may be a higher risk occupation (e.g., an occupation with a risk level that exceeds a threshold value), the correlator 2613 may correlate data such as heart rate data, blood pressure data, hydration level data, with the occupational information to determine a cause of a hydration condition change. For example, when a heart rate and blood pressure of a user increases and a hydration level of the individual decreases while the individual is working at an oil refinery or on a farm, the correlator 2613 may determine that the heart rate or blood pressure increase may be due to physiological influences of the occupation (such as strenuous labor or no breaks) rather than psychological causes (such as stress) because the occupation where the individual is working at may be likely to include physical exertion.

In a further example, the correlator 2613 may use a multiple regression algorithm to determine a correlation between multiple data points or data sets and a physiological condition. For example, the correlator 2613 may receive heart rate data, skin temperature, bioimpedance data, skin luminosity, and hydration level data of a user. In this example, the correlator 2613 may determine a correlation between these types of physiological data and a physiological condition change event of the individual. For example, the physiological data could be from optical spectroscopy (skin luminosity) and/or bioimpedance data. The correlator 2613 may then determine that as the bioimpedance of a user increases and skin luminosity increases, a probability of a dehydration event occurring increases.

Additionally, or alternatively, the correlator 2613 may filter out a correlation determination (e.g., a determination that data points or data sets and a blood sugar condition may be correlated) when a correlation level is below a threshold level. For example, when the correlator 2613 determines that there may be a 30 percent correlation between a skin temperature or a bioimpedance level of a user and a fall event, the correlator 2613 may filter out or disregard the correlation information when determining a cause of the fall event. In another example, the correlator 2613 may use a learning algorithm or machine learning to determine when to filter out a correlation determination. For example, at a first instance of a fall, there may be a 30 percent correlation between a skin temperature or a bioimpedance level of a user and a fall event. The correlator 2613 may monitor multiple fall events and use machine learning to determine that the initial 30 percent correlation is actually a 60 percent correlation and adjust the filter to not filter out the correlation between the skin temperature or the bioimpedance level of a user and a fall event or assign the correlation of the skin temperature or the bioimpedance level of a user and a fall event a different weight.

Additionally, or alternatively, the correlator 2613 may filter out the correlation determination based on a schedule of a user. For example, when the correlator 2613 determines that a user may be taking a lunch break, off of work, or sleeping, the correlator 2613 may filter out environmental conditions that are associated with the occupation of the user, e.g., the correlator 2613 may filter out false positives.

Additionally, or alternatively, the correlator 2613 may discount or weight a correlation determination based on the correlation level of the correlation determination. For example, when the correlator 2613 determines that there may only be a 30 percent correlation between an occupation of a user and a blood glucose level of a user, the correlator 2613 may discount or assign a lower weight to the correlation determination (relative to a higher correlation percentage such as 90 percent) when determining a change in blood sugar condition.

Additionally, or alternatively, the correlator 2613 may assign weights to different factors, such as: physiological data 2624 (e.g., different types or qualities of physiological parameters), environmental data 2626 (e.g., different types or quality of environmental parameters), Newtonian data 2628 (e.g., different types or quality of Newtonian parameters), profile data 2630, location data 2632 (e.g., different types or quality of location parameters), a time of day, and so forth. In an embodiment, the correlator 2613 may assign a first weight to blood glucose level data of a user and a second weight to profile data of a user when determining a probability of a change in blood sugar condition for a user. In this example, when determining the probability of a change in a blood sugar condition, the correlator 2613 may assign a higher weight to the blood glucose level data relative to the profile data, for example.

The correlator 2613 may additionally, or alternatively, use predetermined weights for the physiological data 2624, environmental data 2626, Newtonian data 2628, profile data 2630, and location data 2632. In another example, the correlator 2613 may receive user defined or predefined weights from an input device indicating the weights for the different physiological and/or environmental data. In another example, the correlator 2613 may determine the weights to assign to the physiological data 2624, environmental data 2626, Newtonian data 2628, profile data 2630, and location data 2632 based on correlation levels of the physiological data 2624, environmental data 2626, Newtonian data 2628, profile data 2630, and location data 2632. For example, when a correlation level between a hydration condition and a heart rate of a user may be relatively low over a threshold period of time and/or under a threshold number of different conditions, the correlator 2613 may assign a low weight to heart rate data when determining a cause of a change in hydration condition.

In an embodiment, the correlator 2613 may assign different weights to one or more of the physiological data 2624, environmental data 2626, Newtonian data 2628, profile data 2630, and location data 2632 based on other physiological data 2624, environmental data 2626, Newtonian data 2628, profile data 2630, and location data 2632. For example, based on a location of a user, the correlator 2613 may assign a first weight to environmental data 2626 and a second weight to profile data 2630. In another example, the correlator 2613 may assign weights to different hydration and/or blood sugar conditions.

Additionally, or alternatively, the correlator 2613 may use environmental data 2626 or location data 2632 to determine a cause of a change in hydration condition. For example, when a user may be located at a fitness facility working out, the correlator 2613 may increase a weight for a physical exertion related a change in a hydration condition occurring because of in physical exertion of a user (such as an increase in a heart rate or decrease in a hydration level of a user). In another example, when a user may be located at home in bed resting or sleeping, the correlator 2613 may correlate a location of the user with the hydration condition of the user. In this example, the correlator 2613 may determine that a decrease in probability of a change in a hydration condition occurring due to a user being located in their bedroom for a threshold period of time (e.g., a safer environment).

In one embodiment, the correlator 2613 may determine a weighting of measurement information or physiological information using medical evaluation information. In an embodiment, the medical evaluation information includes medical evaluation information of the user, such as a medical physical. The medical evaluation information may include: medical history and health history information, such as whether the user may be a smoker or a non-smoker; blood pressure information of the user; hereditary diseases information of the user; sexual health information of a user; dietary information of a user; exercise routine information of the user, such as how often the user exercises; heart or lung examination information of the user; blood sugar test results of the user; and so forth. In an embodiment, the correlator 2613 may use the medical evaluation information to set initial weight for different data types. The correlator may update or adjust the weights for the different data types using machine learning. For example, the physiological data 2624, environmental data 2626, and Newtonian data 2628 may be assigned a first set of weights based on the medical evaluation information. As the wearable device 100 uses the sensors to collect the physiological data 2624, environmental data 2626, and the Newtonian data 2628, the correlator 2613 may use the physiological data 2624, the environmental data 2626, and the Newtonian data 2628 to customize the weighting of the measurement information or physiological information to the individual. For example, the correlator 2613 may receive medical evaluation information for the user input device of the wearable device 100 using an input device of the wearable device 100.

The correlator 2613 may track, sort and/or filter input data. The input data may include: user schedule information, such as a daily schedule of the user; survey information, such as information received from surveys of individuals;

research information, such as clinical research information or academic research information associated with one or more blood sugar conditions of the wearable device; and so forth.

The correlator 2613 may use location-based tracking and/or scheduling information of the user in determining an expected or probable change in a blood sugar condition. For example, the correlator 2613 may receive location data indicating the user may be at a restaurant, or the correlator 2613 may receive schedule data of the user indicating the user may be scheduled for a lunch meeting. In this example, the correlator 2613 may use the location and/or schedule information to anticipate that the user may be eating and increase a probability that a change a in diabetic condition may occur.

The correlator 2613 may use timer information determining an expected or probable occurrence of a change in a blood sugar condition. For example, the correlator may monitor how long it may have been since a user had an insulin shot. In this example, as the length of time increases since the last insulin shot, the probability that a change in blood sugar condition may occur increases. In another example, the correlator 2613 may use the timer information to periodically request a response from the user. For example, when a timer has expired for a maximum amount of time between insulin shots, the correlator 2613 may request a response from the user as to whether the user has taken an insulin shot.

In another example, the correlator 2613 may have a work mode (the user is at work) and a home mode (the user is at home), where a type of environmental condition that the wearable device monitors for and/or a probability of a change in a blood sugar condition occurring may increase or decrease when switching between the work mode and the home mode. For example, when the user has a high-activity-level occupation, the correlator 2613 may monitor for change in a hydration condition and/or blood sugar condition related to the occupation when the correlator may be in a work mode and switch to monitoring for changes in a hydration condition and/or blood sugar condition related to low-exertion activities when the correlator may be in a home mode.

In another example, the correlator 2613 may use the scheduling information in correlation with a location of the user to determine an expected or probable change in a hydration condition and/or blood sugar condition. For example, the scheduling information may indicate that the user may be scheduled to attend an awards banquet and dinner at a conference center and the correlator 2613 may adjust the types or probabilities of a change in a blood sugar condition occurring in view of the scheduling information. In this example, while the correlator 2613 may typically decrease a probability of a change in blood sugar condition occurring for the user based on the location information (e.g., the conference center), the correlator 2613 may adjust the types or probabilities of a change in a blood sugar condition occurring in view of the scheduling information that the user may be eating at the awards banquet.

Additionally, or alternatively, the correlator 2613 may track and update activity levels of users and correlate these levels with blood sugar conditions over time. For example, the GPS sensor of the wearable device 100 may indicate that the user usually goes to a restaurant around 12:00 pm on weekdays, and usually goes to a restaurant around 7:00 pm on Saturdays. Although these activities may not be available within the scheduling information or data of the wearable device 100 (or other tethered device), the correlator 2613 may execute machine learning to add to activity data of the user these events that normally occur.

The wearable device 100 may store historical or previous blood sugar condition information of the user. In an embodiment, the correlator 2613 may store the historical information on the memory device 2608 of the wearable device 100. In another example, the correlator 2613 may use a communication device and/or the communication interface 2690 to store the blood sugar condition information on a memory device coupled to or in communication with the wearable device, such as a cloud-based storage device or a memory device of another computing device. In another example, the correlator 2613 may be part of a cloud-based system or the other computing device.

The correlator 2613 may filter and/or sort hydration condition and/or blood sugar condition information. In an embodiment, the correlator 2613 may receive a filter or sort command from the wearable device or an input device to filter and/or sort the hydration condition and/or blood sugar information. In another example, the filter or sort command may include filter parameters and/or sort parameters.

In another example, the correlator 2613 may sort and/or filter the input data based on a trending of blood sugar conditions. For example, the correlator 2613 may sort blood sugar conditions that may be trending in an increasing direction or a decreasing direction and may sort the blood sugar conditions based on the trending. In this example, different blood sugar conditions for a user may be trending in different directions, such as a diabetic event of a user may be increasing in trending and eating events may be stable or stagnant.

In another embodiment, the baseliner 2615 may receive profile information from a new user to include any or a combination of gender, age, weight, health, fitness level, and family health histories. The health and fitness levels of the user may be based at least in part on physiological measurements received from the physiological sensor(s) 2602 and the activity data received from the Newtonian sensors 2604. The baseliner 2615 may then identify, from one or more baseline profiles of other users (e.g., a group of users), a baseline profile that may be most similar to the user profile based on a correlation between the user profile information and baseline profile information. The baseline profiles may include baseline information of a probability of a change in blood sugar conditions occurring for a user. The user profiles may include information of the types of blood sugar conditions that may be probable to occur for a user in the group of users.

The baseliner 2615 may then be able to set a baseline against which to judge a blood sugar condition. In an alternate embodiment, the baseline profile that may be most similar to the user profile is identified from an aggregated baseline profile for one or more individuals corresponding to the one or more baseline profiles. Alternatively, or additionally, the most similar profiles may look at a blood sugar condition that occurs for the individual as compared to individuals in the group. For example, the user may be most similar to another individual because they both react physiologically similarly to periods of fasting. In another example, the user may have a similar blood sugar profile to the most-similar profile, meaning, when the user fasts the user may reach a blood glucose level at a certain point in time that substantially matches the timing of the most-similar profile.

The wearable device 100 may further receive survey information and/or research information from an input device with which to build or add to the user and/or baseline profiles. For example, the wearable device 100 may receive survey information that includes: gender information, age information, physical weight information, general health information, family information, fitness level information, and so forth. In an embodiment, the correlator 2613 may determine a correlation between the survey information and user input data. For example, the correlator 2613 may correlate the age, weight, fitness level, and general health level of a user with survey information from other individuals to determine a correlation between the survey information for the individual and the other individuals. In this example, the baseliner 2615 may set a baseline for a measurement of the wearable device 100 for the individual based on baselines for the other individuals with the same or similar survey information.

In another example, the correlator 2613 may correlate the user information with research information (such as research papers, clinical studies, and so forth). For example, the wearable device may retrieve research information related to a physiological parameter, the correlator 2613 may correlate the research information with hydration conditions and/or blood sugar conditions for the user to generate a research correlation. The baseliner 2615 may then adjust the baseline set for the user related to the hydration conditions and/or blood sugar conditions in response to the research correlation.

The correlator 2613 may store physiological condition information in a physiological condition database 2612. In one embodiment, the correlator 2613 may determine parameters associated with physiological conditions. The parameters may include threshold values for measurements or data values, such as physiological sensor measurements, environmental sensor measurements, Newtonian sensor measurements, location sensor measurements, or profile data 2630. The correlator 2613 may store the physiological condition and the associated blood sugar parameters in the physiological condition database 2612. In an example, the correlator 2613 may determine these parameters may store the physiological condition with the associated parameters in the physiological condition database 2612. In another example, the physiological condition database 2612 may store predetermined physiological conditions with the associated parameters. In another example, the physiological condition database 2612 may receive the physiological conditions and the associated parameters from another device or server 2694.

The preceding examples are intended for purposes of illustration and are not intended to be limiting. The correlator 2613 may identify a correlation between various data points, data sets, data types, and/or physiological conditions such as hydration conditions and/or blood sugar conditions. After having a correlation that informs, for example, a diabetic event, the blood glucose level, a dehydration event, the hydration condition and/or other related physiological condition of the user, and further in consideration of a present activity of the user, the alerter 2617 may alert the user at the proper time how to moderate activities such as eating or exercising to avoid or minimize a diabetic event and/or dehydration event.

As used herein, one or more items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and examples of the present disclosure may be referred to herein along with alternatives for the various components thereof. It may be understood that such embodiments, examples, and alternatives are not to be construed as de facto equivalents of one another but are to be considered as separate and autonomous representations of the present disclosure.

Furthermore, the described features, structures, or characteristics may be combined in any suitable manner in one or more embodiments. In the foregoing description, numerous specific details are provided, such as examples of layouts, distances, network examples, and so forth, to provide a thorough understanding of embodiments of the disclosure. One skilled in the art will recognize, however, that the disclosure may be practiced without one or more of the specific details, or with other methods, components, layouts, and so forth. In other instances, well-known structures, materials, or operations are not shown or described in detail to avoid obscuring embodiments of the disclosure.

While the foregoing examples are illustrative of the principles of the present disclosure in one or more particular applications, numerous modifications in form, usage and details of implementation may be made without the exercise of inventive faculty, and without departing from the principles and concepts of this disclosure. Accordingly, it is not intended that this disclosure be limited, except as by the claims.

The words "example" or "embodiment" are used herein to mean serving as an example, instance or illustration. Use of the words "example" or "embodiment" may be intended to present concepts in a concrete fashion. As used in this application, the term "or" may be intended to mean an inclusive "or" rather than an exclusive "or." That is, unless specified otherwise, or clear from context, "X includes A or B" may be intended to mean any of the natural inclusive permutations. That is, if X includes A; X includes B; or X includes both A and B, then "X includes A or B" may be satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Also, the terms "first," "second," "third," "fourth," and so forth as used herein are meant as labels to distinguish among different elements and may not necessarily have an ordinal meaning according to their numerical designation.

The invention claimed is:

1. A device, comprising:
   a band configured to extend at least partially around a body part of a user, the body part comprising:
   a first subdermal feature at a first depth within the body part;
   a second subdermal feature at a second depth within the body part deeper than the first depth, wherein the first subdermal feature and the second subdermal feature are positioned in a same region of the body part; and
   a miniaturized impedance sensor embedded in the band and positioned in the band to be pressed against the same region of the body part having the first subdermal feature and the second subdermal feature as the user wears the band, the miniaturized impedance sensor comprising:

a first miniaturized electrode configured in the band to transmit an electronic signal through the body part as the user wears the band, wherein the first miniaturized electrode is configured to transmit the electronic signal at a first power level or a second power level;
a second miniaturized electrode spaced in the band from the first miniaturized electrode at a first distance, wherein the first distance is configured so that:
the second miniaturized electrode receives the electronic signal from the first miniaturized electrode through the first subdermal feature when the user wears the band; and
the electronic signal bypasses the second subdermal feature when it is received by the second miniaturized electrode;
wherein the first distance is less than a first threshold distance to prevent the electronic signal from penetrating into the body part to the second depth of the second subdermal feature; and
a third miniaturized electrode spaced from the first miniaturized electrode at a second distance, wherein:
the second distance is greater than the first distance; and
the third miniaturized electrode is configured to receive the electronic signal from the first miniaturized electrode through the second subdermal feature when the user wears the band;
wherein the miniaturized impedance sensor comprises at least one insulating layer, a conductive layer, a catalyst layer, and an interstitial filler, and wherein the first, second and third miniaturized electrodes are configured in parallel rows; and
wherein the interstitial filler includes a plurality of interstitial wells between the parallel rows of miniaturized electrodes configured to:
be flush with a surface of the miniaturized impedance sensor to form a continuous surface; and
allow a dermal feature to flex into the plurality of interstitial wells.

2. The device of claim 1, wherein when the first miniaturized electrode is configured to transmit the electronic signal at the first power level and at the first distance from the second miniaturized electrode, the first miniaturized electrode is configured to generate a circular electric field in the body part as the user wears the band.

3. The device of claim 2, wherein when the first miniaturized electrode is configured to transmit the electronic signal at the second power level and at the second distance from the second miniaturized electrode, the first miniaturized electrode is configured to generate an elliptical electric field in the body part as the user wears the band.

4. The device of claim 1, wherein:
the body part is a wrist of the user;
the first subdermal feature is a dermal layer of the wrist on an underside of the wrist; and
the second subdermal feature is a muscular-walled tube adjacent to the dermal layer of the wrist.

5. The device of claim 1, wherein the first miniaturized electrode and the second miniaturized electrode, or the first miniaturized electrode and the third miniaturized electrode, are positioned in the band such that, as the user wears the band:
a first electric field between the first miniaturized electrode and the second miniaturized electrode, or between the first miniaturized electrode and the third miniaturized electrode, is aligned parallel to a muscular-walled tube of the body part; or a second electric field between the first, miniaturized electrode and the second miniaturized electrode, or between the first miniaturized electrode and the third miniaturized electrode, is aligned perpendicular to the muscular-walled tube.

6. The device of claim 1, wherein:
the miniaturized impedance sensor further comprises an array of miniaturized electrodes comprising the first miniaturized electrode, the second miniaturized electrode, the third miniaturized electrode, or a fourth miniaturized electrode;
a processing device is integrated into the band and electronically coupled to the miniaturized impedance sensor; and
the processing device configured to automatically select a pair of miniaturized electrodes from the array of miniaturized electrodes based on an impedance signal generated by the pair of miniaturized electrodes.

7. The device of claim 1, wherein the first miniaturized electrode is configured in the miniaturized impedance sensor to transmit the electronic signal at a discreet frequency or at a spectrum of different frequencies.

8. The device of claim 7, further comprising a processing device integrated into the band, wherein the processing device is configured to measure an impedance of the first subdermal feature or the second subdermal feature for the spectrum of different frequencies by transmitting the electronic signal from the first miniaturized electrode at the first power level or the second power level and across the spectrum of different frequencies.

9. The device of claim 7, further comprising a processing device integrated into the band, wherein the processing device is configured to:
iteratively select transmitting the electronic signal between the first miniaturized electrode and the second miniaturized electrode and between the first miniaturized electrode and the third miniaturized electrode until the miniaturized impedance sensor detects the electronic signal indicative of a threshold impedance measurement; or
iteratively select a frequency from the spectrum of different frequencies, until the miniaturized impedance sensor detects the electronic signal indicative of the threshold impedance measurement, wherein the threshold impedance measurement corresponds to a measurement taken at the first subdermal feature or the second subdermal feature.

10. The device of claim 1, further comprising a user interface and a processing device electronically coupled to the miniaturized impedance sensor, wherein:
the processing device is configured to apply power via a power source to the first miniaturized electrode such that the first miniaturized electrode transmits the electronic signal when the user selects, via the user interface, a first measurement corresponding to the first subdermal feature; and
the processing device is configured to apply the power via the power source to the second miniaturized electrode such that the second miniaturized electrode transmits an additional electronic signal when the user selects, via the user interface, a second measurement corresponding to the second subdermal feature.

11. An apparatus, comprising:
a band configured to extend at least partially around a body part of a user, the body part comprising:
a first subdermal feature at a first depth within the body part;

a second subdermal feature at a second depth within the body part deeper than the first depth, wherein the first subdermal feature and the second subdermal feature are positioned in a same region of the body part;

a miniaturized impedance sensor embedded in the band and positioned in the band to be pressed against the same region of the body part having the first subdermal feature and the second subdermal feature as the user wears the band, the miniaturized impedance sensor comprising:

a first miniaturized electrode configured in the band to transmit an electronic signal through the body part as the user wears the band, wherein the first miniaturized electrode is configured to transmit the electronic signal at a first power level or a second power level;

a second miniaturized electrode spaced in the band from the first miniaturized electrode at a first distance, wherein the first distance is configured so that:

the second miniaturized electrode receives the electronic signal from the first miniaturized electrode through the first subdermal feature when the user wears the band; and the electronic signal bypasses the second subdermal feature when it is received by the second miniaturized electrode;

wherein the first distance is less than a first threshold distance to prevent the electronic signal from penetrating into the body part to the second depth of the second subdermal feature; and a third miniaturized electrode spaced from the first miniaturized electrode at a second distance, wherein:

the second distance is greater than the first distance; and the third miniaturized electrode is configured to receive the electronic signal from the first miniaturized electrode through the second subdermal feature when the user wears the band; and a processing device coupled to the band and configured to select the first depth of the first subdermal feature or the second depth of the second subdermal feature, wherein the first depth is selected to correspond to the first subdermal feature or the second depth is selected to correspond to the second subdermal feature within the body part based on the first distance or the second distance between the first miniaturized electrode and the second miniaturized electrode or the third miniaturized electrode, wherein the miniaturized impedance sensor comprises at least one insulating layer, a conductive layer, a catalyst layer, and an interstitial filler, and wherein the first, second and third miniaturized electrodes are configured in parallel rows; and wherein the interstitial filler includes a plurality of wells between the parallel rows of miniaturized electrodes configured to:

be flush with a surface of the miniaturized impedance sensor to form a continuous surface, and allow a dermal feature to flex into the plurality of wells.

12. The apparatus of claim 11, wherein the processing device is configured to measure impedance at the first depth and the second depth within the body part as the user wears the band.

13. The apparatus of claim 11, wherein the miniaturized impedance sensor further comprises:

a first row of miniaturized electrodes configured to transmit a corresponding electronic signal; and two or more other rows of miniaturized electrodes configured to receive the corresponding electronic signal.

14. The apparatus of claim 11, wherein the miniaturized impedance sensor is configured to transmit and/or receive the electronic signal based on a power source applying power to the miniaturized impedance sensor.

15. The apparatus of claim 11, wherein the miniaturized impedance sensor is configured to switch from the second miniaturized electrode receiving the electronic signal when the user wears the band to the third miniaturized electrode receiving the electronic signal when the user wears the band based on a difference between a first signal to noise ratio corresponding to the first subdermal feature of the body part and a second signal to noise ratio corresponding to the second subdermal feature of the body part.

16. An apparatus, comprising:

a band configured to extend at least partially around a body part of a user; and a miniaturized impedance sensor embedded in the band and positioned in the band to be pressed against a region of the body part having a first subdermal feature and a second subdermal feature as the user wears the band, the miniaturized impedance sensor comprising an array of miniaturized electrodes at corresponding locations on the band, wherein the array of miniaturized electrodes is configured to transmit an electrical signal through the body part as the user wears the band, each of the array of miniaturized electrodes positioned on the band at the locations to receive the electrical signal and correspond to the first and second subdermal features of the body part at corresponding depths within the body part, wherein the miniaturized impedance sensor comprises at least one insulating layer, a conductive layer, a catalyst layer and an interstitial filler; and wherein said miniaturized electrodes are configured in parallel rows; and wherein the interstitial filler includes a plurality of wells between the parallel rows of miniaturized electrodes configured to:

be flush with a surface of the miniaturized impedance sensor to form a continuous surface, and allow a dermal feature to flex into the plurality of wells.

17. The apparatus of claim 16, wherein the array of miniaturized electrodes comprises:

a first miniaturized electrode configured to transmit the electrical signal into the body part when the user wears the band; and a second miniaturized electrode configured to receive the electrical signal through the body part when the user wears the band.

18. The apparatus of claim 16, further comprising a processing device coupled to the miniaturized impedance sensor, wherein the processing device is configured to:

turn on a power source such that the power source applies power to the array of miniaturized electrodes;

select a miniaturized electrode of the array of miniaturized electrodes to receive the electrical signal through the body part as the user wears the band;

determine an impedance of the electrical signal; and compare the impedance of the electrical signal to defined impedance values, wherein the defined impedance values are associated with one or more of the first and second subdermal features of the body part.

19. The apparatus of claim 18, wherein:
the processing device is configured to adjust a signal to noise ratio of the electrical signal transmitted and received by the array of miniaturized electrodes; and
the electrical signal is indicative of an impedance of the body part as he electrical signal is transmitted through the body part.

20. The apparatus of claim 18, wherein the processing device is configured to correlate a change in the impedance with a change in the body part, wherein the body part comprises a muscular-walled tube within the body part, the muscular-walled tube having blood flowing through the muscular-walled tube, and wherein the change in the impedance comprises a change in an amount of glucose in the blood flowing through the muscular-walled tube.

* * * * *